(12) United States Patent
Oh et al.

(10) Patent No.: US 10,857,177 B2
(45) Date of Patent: Dec. 8, 2020

(54) LIPIDATED PSA COMPOSITIONS AND METHODS

(71) Applicant: President and Fellows of Harvard College, Cambridge, MA (US)

(72) Inventors: Sungwhan Oh, Brookline, MA (US); Deniz Erturk-Hasdemir, Framingham, MA (US); Dennis L. Kasper, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 107 days.

(21) Appl. No.: 15/753,129

(22) PCT Filed: Aug. 19, 2016

(86) PCT No.: PCT/US2016/047787
§ 371 (c)(1),
(2) Date: Feb. 15, 2018

(87) PCT Pub. No.: WO2017/031431
PCT Pub. Date: Feb. 23, 2017

(65) Prior Publication Data
US 2019/0046560 A1    Feb. 14, 2019

Related U.S. Application Data

(60) Provisional application No. 62/207,360, filed on Aug. 19, 2015.

(51) Int. Cl.
| | | |
|---|---|---|
| *A61K 45/00* | (2006.01) |
| *A61K 31/739* | (2006.01) |
| *C08B 37/00* | (2006.01) |
| *A61K 47/54* | (2017.01) |
| *A61P 37/06* | (2006.01) |
| *A61P 31/04* | (2006.01) |
| *A61P 29/00* | (2006.01) |
| *A61K 9/107* | (2006.01) |
| *A61K 9/127* | (2006.01) |

(52) U.S. Cl.
CPC .......... *A61K 31/739* (2013.01); *A61K 9/1075* (2013.01); *A61K 9/1271* (2013.01); *A61K 47/544* (2017.08); *A61P 29/00* (2018.01); *A61P 31/04* (2018.01); *A61P 37/06* (2018.01); *C08B 37/0003* (2013.01)

(58) Field of Classification Search
None
See application file for complete search history.

(56) References Cited

U.S. PATENT DOCUMENTS

| | | |
|---|---|---|
| 3,723,506 A | 3/1973 | Deslongchamps |
| 3,849,550 A | 11/1974 | Teitelbaum et al. |
| 4,316,982 A | 2/1982 | Holst |
| 4,356,170 A | 10/1982 | Jennings et al. |
| 4,619,995 A | 10/1986 | Hayes |
| 4,740,480 A | 4/1988 | Ooka |
| 4,775,626 A | 10/1988 | Armenta et al. |
| 4,782,067 A | 11/1988 | Blythin et al. |
| 4,819,617 A | 4/1989 | Goldberg |
| 4,835,252 A | 5/1989 | Kaiser et al. |
| 4,886,787 A | 12/1989 | de Belder et al. |
| 4,937,270 A | 6/1990 | Hamilton et al. |
| 4,952,524 A | 8/1990 | Lee et al. |
| 5,126,141 A | 6/1992 | Henry |
| 5,130,417 A | 7/1992 | Stanley et al. |
| 5,140,016 A | 8/1992 | Goldberg et al. |
| 5,158,939 A | 10/1992 | Takayama et al. |
| 5,196,510 A | 3/1993 | Rodwell et al. |
| 5,215,896 A | 6/1993 | Keck et al. |
| 5,229,315 A | 7/1993 | Jun et al. |
| 5,331,573 A | 7/1994 | Balaji et al. |
| 5,468,676 A | 11/1995 | Madan |
| 5,514,581 A | 5/1996 | Ferrari et al. |
| 5,532,221 A | 7/1996 | Huang et al. |
| 5,565,204 A | 10/1996 | Kuo et al. |
| 5,576,002 A | 11/1996 | Jennings et al. |
| 5,576,241 A | 11/1996 | Sakai |
| 5,605,938 A | 2/1997 | Roufa et al. |
| 5,679,654 A | 10/1997 | Tzianabos et al. |
| 5,679,658 A | 10/1997 | Elson |
| 5,700,787 A | 12/1997 | Tzianabos et al. |
| 5,700,906 A | 12/1997 | Arnot et al. |
| 5,705,178 A | 1/1998 | Roufa et al. |

(Continued)

FOREIGN PATENT DOCUMENTS

| | | |
|---|---|---|
| CN | 1818061 A | 8/2006 |
| DE | 3704389 A1 | 8/1988 |

(Continued)

OTHER PUBLICATIONS

Pato et al. Journal of Chromatography B, vol. 832, pp. 262-267,2006. (Year: 2006).*
Extended European Search Report for Application No. 16837913.9, dated Jun. 19, 2019.
International Preliminary Report on Patentability for Application No. PCT/US2016/047787, dated Mar. 1, 2018.
International Search Report and Written Opinion for Application No. PCT/US2016/047787, dated Jan. 6, 2017.
GenBank Accession No. AJ277832; Hutloff Jan. 19, 2001.
GenBank Accession No. CAC06612; Hutloff Jan. 19, 2001.
GenBank Accession No. NM_012092; Dec. 20, 2003.
GenBank Accession No. NP_036224 Dec. 20, 2003.
[No Author Listed] Excerpts from Immunobiology, 7th ed. 2008. Part IV: The Adaptive Immune Response. Chapter 9 T Cell-Mediated Immunity.

(Continued)

*Primary Examiner* — Jana A Hines
*Assistant Examiner* — Khatol S Shahnan Shah
(74) *Attorney, Agent, or Firm* — Wolf, Greenfield & Sacks, P.C.

(57) ABSTRACT

The invention provides various isolated and synthetic forms of lipidated PSA as well as isolated or synthetic forms of the glycolipid component of lipidated PSA, and compositions thereof, methods of making including methods of isolating such forms, and methods of use thereof.

12 Claims, 19 Drawing Sheets

(56) References Cited

U.S. PATENT DOCUMENTS

| | | |
|---|---|---|
| 5,760,200 A | 6/1998 | Miller et al. |
| 5,851,808 A | 12/1998 | Elledge et al. |
| 5,853,718 A | 12/1998 | Molin et al. |
| 5,868,870 A | 2/1999 | Fazan et al. |
| 5,888,741 A | 3/1999 | Hendry |
| 5,929,049 A | 7/1999 | Singh et al. |
| 5,936,076 A | 10/1999 | Higa et al. |
| 5,993,825 A | 11/1999 | Jennings et al. |
| 6,027,733 A | 2/2000 | Wang et al. |
| 6,110,672 A | 8/2000 | Mandel et al. |
| 6,150,459 A | 11/2000 | Mayes et al. |
| 6,274,144 B1 | 8/2001 | Wang et al. |
| 6,294,518 B1 | 9/2001 | Potter et al. |
| 6,358,939 B1 | 3/2002 | Hayes et al. |
| 6,447,765 B1 | 9/2002 | Horwitz |
| 6,670,146 B2 | 12/2003 | Barrat et al. |
| 6,749,831 B1 | 6/2004 | Bennett-Guerrero et al. |
| 6,995,237 B1 | 2/2006 | Zimmerman |
| 7,026,285 B2 | 4/2006 | Tzianabos et al. |
| 7,083,777 B1 | 8/2006 | Tzianabos et al. |
| 7,163,683 B2 | 1/2007 | Barstad et al. |
| 7,166,455 B2 | 1/2007 | Comstock et al. |
| 7,384,645 B2 | 6/2008 | Foster et al. |
| 7,629,330 B2 | 12/2009 | Wang et al. |
| 7,678,558 B2 | 3/2010 | Comstock et al. |
| 7,803,602 B2 | 9/2010 | Comstock et al. |
| 7,807,154 B2 | 10/2010 | Strasburger et al. |
| 8,008,276 B2 | 8/2011 | Wang et al. |
| 8,206,726 B2 | 6/2012 | Kasper et al. |
| 8,580,278 B2 | 11/2013 | Kasper et al. |
| 8,586,029 B2 | 11/2013 | Kasper et al. |
| 9,057,070 B2 | 6/2015 | Mazmanian et al. |
| 9,265,790 B2 | 2/2016 | Tzianabos et al. |
| 9,539,281 B2 | 1/2017 | Kasper et al. |
| 2001/0001788 A1 | 5/2001 | Satoh et al. |
| 2002/0022019 A1 | 2/2002 | Laulund |
| 2002/0090357 A1 | 7/2002 | Barrat et al. |
| 2002/0155436 A1 | 10/2002 | Classen |
| 2003/0044425 A1 | 3/2003 | Burt et al. |
| 2003/0059462 A1 | 3/2003 | Barenholz et al. |
| 2003/0147865 A1 | 8/2003 | Salomon et al. |
| 2003/0219413 A1 | 11/2003 | Comstock et al. |
| 2004/0185057 A1 | 1/2004 | Kirkby et al. |
| 2004/0039056 A1 | 2/2004 | Bollag et al. |
| 2004/0092433 A1 | 5/2004 | Wang et al. |
| 2004/0219160 A1 | 11/2004 | Tzianabos et al. |
| 2005/0020515 A1 | 1/2005 | Graff et al. |
| 2005/0063979 A1 | 3/2005 | Pickl et al. |
| 2005/0101012 A1 | 5/2005 | Schuler et al. |
| 2005/0119164 A1 | 6/2005 | Taylor et al. |
| 2005/0147624 A1 | 7/2005 | Jennings et al. |
| 2005/0181021 A1 | 8/2005 | Lamb |
| 2005/0271643 A1 | 12/2005 | Sorokulova et al. |
| 2006/0014717 A1 | 1/2006 | Angstrom et al. |
| 2006/0110412 A1 | 5/2006 | Desmons et al. |
| 2006/0116332 A1 | 6/2006 | Strober et al. |
| 2006/0153832 A1 | 7/2006 | Tzianabos et al. |
| 2006/0257852 A1 | 11/2006 | Rappuoli et al. |
| 2006/0275752 A1 | 12/2006 | Sindhi |
| 2007/0020730 A1 | 1/2007 | Comstock et al. |
| 2007/0154991 A1 | 7/2007 | Comstock et al. |
| 2007/0207526 A1 | 9/2007 | Coit et al. |
| 2007/0238747 A1 | 10/2007 | van Duzer et al. |
| 2008/0057565 A1 | 3/2008 | Comstock et al. |
| 2008/0131445 A1 | 6/2008 | Bluestone et al. |
| 2008/0286252 A1 | 11/2008 | Sinnott |
| 2009/0017472 A1 | 1/2009 | Stuhlmuller et al. |
| 2009/0124573 A1 | 5/2009 | Mazmanian et al. |
| 2009/0252708 A1 | 10/2009 | Fitzpatrick et al. |
| 2009/0317410 A1 | 12/2009 | Wang et al. |
| 2009/0317427 A1 | 12/2009 | Kasper et al. |
| 2010/0080760 A1 | 4/2010 | Hyde et al. |
| 2010/0112002 A1 | 5/2010 | Lien et al. |
| 2010/0221269 A1 | 9/2010 | Boons et al. |
| 2010/0221315 A1 | 9/2010 | Constantino et al. |
| 2010/0221755 A1 | 9/2010 | Lee et al. |
| 2010/0275282 A1 | 10/2010 | Round et al. |
| 2010/0311686 A1 | 12/2010 | Kasper et al. |
| 2010/0330166 A1 | 12/2010 | Ishida et al. |
| 2011/0002965 A1 | 1/2011 | Round et al. |
| 2011/0009360 A1 | 1/2011 | Kasper et al. |
| 2011/0059125 A1 | 3/2011 | Tzianabos et al. |
| 2011/0086011 A1 | 4/2011 | Kasper et al. |
| 2011/0150852 A1 | 6/2011 | Chambaud et al. |
| 2011/0229513 A1 | 9/2011 | Cox et al. |
| 2011/0251156 A1 | 10/2011 | Shen et al. |
| 2011/0287048 A1 | 11/2011 | Round et al. |
| 2012/0087895 A1 | 4/2012 | Mazmanian et al. |
| 2012/0094950 A1 | 4/2012 | Kasper et al. |
| 2012/0309955 A1 | 12/2012 | Kasper et al. |
| 2012/0315264 A1 | 12/2012 | Tzianabos et al. |
| 2013/0039949 A1 | 2/2013 | Mazmanian et al. |
| 2013/0058997 A1 | 3/2013 | Reed et al. |
| 2013/0064859 A1 | 3/2013 | Mazmanian et al. |
| 2013/0121966 A1 | 5/2013 | Mazmanian et al. |
| 2013/0195802 A1 | 8/2013 | Moore |
| 2014/0030807 A1 | 1/2014 | Kasper et al. |
| 2014/0072534 A1 | 3/2014 | Mazmanian et al. |
| 2014/0099331 A1 | 4/2014 | Tzianabos et al. |
| 2014/0243285 A1* | 8/2014 | Kasper ............... C08B 37/0003 514/54 |
| 2014/0335131 A1 | 11/2014 | Mazmanian et al. |
| 2016/0022727 A1 | 1/2016 | Round et al. |
| 2016/0030464 A1 | 2/2016 | Mazmanian et al. |
| 2019/0290680 A1 | 9/2019 | Oh et al. |

FOREIGN PATENT DOCUMENTS

| | | |
|---|---|---|
| EP | 0382576 A1 | 8/1990 |
| EP | 0497524 A2 | 8/1992 |
| EP | 1358885 A1 | 11/2003 |
| EP | 1459757 A1 | 9/2004 |
| EP | 0371414 A2 | 6/2006 |
| GB | 2286193 A | 8/1995 |
| JP | 56128721 | 10/1981 |
| JP | H10-507746 | 7/1998 |
| JP | 2002541113 | 12/2002 |
| JP | 2004536028 | 12/2004 |
| JP | 2006522135 | 9/2006 |
| JP | 2012-524910 A | 10/2012 |
| WO | WO 84/04526 A1 | 11/1984 |
| WO | WO 95/31990 A1 | 11/1995 |
| WO | WO 96/07427 A1 | 3/1996 |
| WO | WO 96/32119 A1 | 10/1996 |
| WO | WO 96/35433 A1 | 11/1996 |
| WO | WO 98/42718 A1 | 10/1998 |
| WO | WO 98/45335 A1 | 10/1998 |
| WO | WO 00/01733 A1 | 1/2000 |
| WO | WO 00/59515 A2 | 10/2000 |
| WO | WO 02/07741 A1 | 1/2002 |
| WO | WO 02/045708 A2 | 6/2002 |
| WO | WO 03/075953 A2 | 9/2003 |
| WO | WO 2003/077863 A2 | 9/2003 |
| WO | WO 03/095606 A2 | 11/2003 |
| WO | WO 04/050909 A2 | 6/2004 |
| WO | WO 2004/089407 | 10/2004 |
| WO | WO 2005/010215 | 2/2005 |
| WO | WO 2007/040446 | 4/2007 |
| WO | WO 2007/092451 | 8/2007 |
| WO | WO 2008/095141 | 8/2008 |
| WO | WO 2009/062132 | 5/2009 |
| WO | WO 2009/149149 | 12/2009 |
| WO | WO 2010/124256 | 10/2010 |
| WO | WO 2011/056703 | 5/2011 |
| WO | WO 2011/127302 | 10/2011 |
| WO | WO 2011/146910 | 11/2011 |
| WO | WO 2011/153226 | 12/2011 |
| WO | WO 2012/027032 | 3/2012 |
| WO | WO 2012/103532 | 8/2012 |
| WO | WO 2013/009945 | 1/2013 |
| WO | WO 2013/019896 | 2/2013 |
| WO | WO 2013/036290 | 3/2013 |
| WO | WO 2013/052099 | 4/2013 |

(56) References Cited

FOREIGN PATENT DOCUMENTS

| WO | WO 2014/182966 | 11/2014 |
|----|----------------|---------|
| WO | WO 2015/147899 | 10/2015 |
| WO | WO 2017/031431 | 2/2017  |

OTHER PUBLICATIONS

[No Author Listed] Acute Respiratory Disease Syndrome: What is acute respiratory disease syndrome? American Lung Association. 3 pages. http://www.lungusa.org/site/apps/nlnet/content3.aspz?c=dvLUK9O0E&b=2058817&content. Sep. 24, 2008.

[No Author Listed] Lupus study. Meet a Lupus Researcher. www.lupusstudy.org/updates.php. Nov. 2005;1-2.

[No Author Listed] Polyethylene Glycols (PEGs). Accessed Mar. 7, 2005. 1 page. http://www.mindfully.org/Plastic/Polymers/Polyethylene-Glycols-PEGs.htm.

[No Author Listed] The Merck Index . Eleventh Edition 1989:734-735.

[No Author Listed] VAXA, Systemic lupus erythematosus (SLE), damaging and unpredictable. http://www.vaxa.com/arthritis-systemic-lupus-erythematosus.cfm. 1 page. Accessed Apr. 3, 2008.

[No Author Listed] "Asthma" from the Centers for Disease Control and Prevention. Retrieved Nov. 13, 2012. www.cdc.gov/asthma/aag/2010/overview.html, pp. 1-2.

[No Author Listed] Drug Absorption, Bioavailability, and Routes of Administration. Goodman & Gilman's The Pharmacological Basis of Therapeutics, Tenth Edition, McGraw-Hill Medical Publishing Edition, New York, 2001, pp. 5-8.

[No Author Listed] MS the Disease. National Multiple Sclerosis Society. http://www.nationalmssociety.org/. 4 pages.

[No Author Listed] National Public Health Partnership, The Language of Prevention. Melbourne: NPHP. 2006. 9 pages.

[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.

[No Author Listed] NCBI Sequence View "Toxin" [*Salmonella typhimurium* LT2]. http://www.ncbi.nim.nih.gov/entrez/viewer.fcgi?db=protein&id=17233414, pp. 1-2.

Abreu et al., Measurement of vitamin D levels in inflammatory bowel disease patients reveals a subset of Crohn's disease patients with elevated 1,25-dihydroxyvitamin D and low bone mineral density. Gut. Aug. 2004;53(8):1129-36.

Abt et al., Commensal bacteria calibrate the activation threshold of innate antiviral immunity. Immunity. Jul. 27, 2012;37(1):158-70. doi: 10.1016/j.immuni.2012.04.011. Epub Jun. 14, 2012.

Adams et al., Extrarenal expression of the 25-hydroxyvitamin D-1-hydroxylase. Arch Biochem Biophys. Jul. 1, 2012;523(1):95-102. doi: 10.1016/j.abb.2012.02.016. Epub Mar 14, 2012.

Adams et al., Unexpected actions of vitamin D: new perspectives on the regulation of innate and adaptive immunity. Nat Clin Pract Endocrinol Metab. Feb. 2008;4(2):80-90. doi: 10.1038/ncpendmet0716.

Adkins, T-cell function in newborn mice and humans. Immunol Today. Jul. 1999;20(7):330-5.

Adkins, Development of neonatal Th1/Th2 function. Int Rev Immunol. 2000;19(2-3):157-71.

Adkins et al., Early block in maturation is associated with thymic involution in mammary tumor-bearing mice. J Immunol. Jun. 1, 2000;164(11):5635-40.

Adkins et al., Exclusive Th2 primary effector function in spleens but mixed Th1/Th2 function in lymph nodes of murine neonates. J Immunol. Mar. 1, 2000;164(5):2347-53.

Afzali, The role of T helper 17 (Th17) and regulatory T cells (Treg) in human organ transplantation and autoimmune disease. Clin Exp Immunol. Apr. 2007;148(1):32-46.

Aharoni et al., Copolymer 1 induces T cells of the T helper type 2 that crossreact with myelin basic protein and suppress experimental autoimmune encephalomyelitis. Proc Natl Acad Sci U S A. Sep. 30, 1997;94(20):10821-6.

Aharoni et al., Bystander suppression of experimental autoimmune encephalomyelitis by T cell lines and clones of the Th2 type induced by copolymer 1. J Neuroimmunol. Nov. 2, 1998;91(1-2):135-46.

Aharoni et al., Studies on the mechanism and specificity of the effect of the synthetic random copolymer GLAT on graft-versus-host disease. Immunol Lett. Jul. 1997;58(2):79-87.

Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.

Al-Bader et al., Activation of human dendritic cells is modulated by components of the outer membranes of Neisseria meningitidis. Infect Immun. Oct. 2003;71(10):5590-7.

Allen et al., A pilot study of the immunological effects of high-dose vitamin D in healthy volunteers. Mult Scler. Dec. 2012;18(12):1797-800. doi: 10.1177/1352458512442992. Epub Mar. 28, 2012.

Amsen et al., Instruction of distinct CD4 T helper cell fates by different notch ligands on antigen-presenting cells. Cell. May 14, 2004;117(4):515-26.

Anderson et al., A transgenic model of central nervous system autoimmunity mediated by CD4+ and CD8+ T and B cells. J Immunol. Mar. 1, 2012;188(5):2084-92. doi: 10.4049/jimmunol.1102186. Epub Jan. 25, 2012.

Arnon et al., New insights into the mechanism of action of copolymer 1 in experimental allergic encephalomyelitis and multiple sclerosis. J Neurol. Apr. 1996;243(4 Suppl 1):S8-13. Review.

Asadullah et al., Interleukin-10 therapy—review of a new approach. Pharmacol Rev. Jun. 2003;55(2):241-69.

Ascherio et al., Vitamin D and multiple sclerosis. Lancet Neurol. Jun. 2010;9(6):599-612. doi: 10.1016/S1474-4422(10)70086-7.

Asseman et al., An essential role for interleukin 10 in the function of regulatory T cells that inhibit intestinal inflammation. J Exp Med. Oct. 4, 1999;190(7):995-1004.

Atarashi et al., ATP drives lamina propria T(H)17 cell differentiation. Nature. Oct. 9, 2008;455(7214):808-12. doi: 10.1038/nature07240. Epub Aug. 20, 2008.

Awasthi et al., Interplay between effector Th17 and regulatory T cells. J Clin Immunol. Nov. 2008;28(6):660-70. doi: 10.1007/s10875-008-9239-7. Epub Sep. 23, 2008.

Azzawi et al., Identification of activated T lymphocytes and eosinophils in bronchial biopsies in stable atopic asthma. Am Rev Respir Dis. Dec. 1990;142(6 Pt 1):1407-13.

Bach, The effect of infections on susceptibility to autoimmune and allergic diseases. N Engl J Med. Sep. 19, 2002;347(12):911-20.

Baecher-Allan et al., CD2 costimulation reveals defective activity by human CD4+CD25(hi) regulatory cells in patients with multiple sclerosis. J Immunol. Mar. 15, 2011;186(6):3317-26. doi: 10.4049/jimmunol.1002502. Epub Feb. 7, 2011.

Banerjee et al., Expansion of FOXP3high regulatory T cells by human dendritic cells (DCs) in vitro and after injection of cytokine-matured DCs in myeloma patients. Blood. Oct. 15, 2006;108(8):2655-61. Epub Jun. 8, 2006.

Bar-On et al., Defining in vivo dendritic cell functions using CD11c-DTR transgenic mice. Methods Mol Biol. 2010;595:429-42. doi: 10.1007/978-1-60761-421-0_28.

Baranzini et al., Genome, epigenome and RNA sequences of monozygotic twins discordant for multiple sclerosis. Nature. Apr. 29, 2010;464(7293):1351-6. doi: 10.1038/nature08990.

Barnes et al., How do Corticosteroids Work in Asthma? Ann. Intern. Med. 2003;139:359-70.

Barnes et al., Regulatory T cells reinforce intestinal homeostasis. Immunity. Sep. 18, 2009;31(3):401-11. doi: 10.1016/j.immuni.2009.08.011.

Barrat et al., In vitro generation of interleukin 10-producing regulatory CD4(+) T cells is induced by immunosuppressive drugs and inhibited by T helper type 1 (Th1)- and Th2-inducing cytokines. J Exp Med. Mar. 4, 2002;195(5):603-16.

Barutca et al., Prevention of interleukin-2-induced severe bronchospasm with salbutamol. J Aerosol Med. 2003 Summer;16(2):183-4.

Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.

(56) References Cited

OTHER PUBLICATIONS

Batta et al., Conformational stabilization of the altruronic acid residue in the O-specific polysaccharide of Shigella sonnei/Plesiomonas shigelloides. Carbohydr Res. Dec. 1997;305(1):93-9.
Baumann et al., Structural elucidation of two capsular polysaccharides from one strain of Bacteroides fragilis using high-resolution NMR spectroscopy. Biochemistry. Apr. 28, 1992;31(16):4081-9.
Bayley et al. Analysis of cepA and other *Bacteroides fragilis* genes reveals a unique promoter structure. (2000) FEMS Microbiol Lett 193:149-54.
Bazan et al., Unraveling the structure of IL-2. Science. Jul. 17, 1992;257(5068):410-3.
Becker et al., Clustering of non-major histocompatibility complex susceptibility candidate loci in human autoimmune diseases. Proc Natl Acad Sci U S A. Aug. 18, 1998;95(17):9979-84.
Becker et al., TGF-beta suppresses tumor progression in colon cancer by inhibition of IL-6 trans-signaling. Immunity. Oct. 2004;21(4):491-501.
Belkaid et al., Regulatory T cells in the control of host-microorganism interactions (*). Annu Rev Immunol. 2009;27:551-89. doi: 10.1146/annurev.immunol.021908.132723.
Bell, Function of CD4 T cell subsets in vivo: expression of CD45R isoforms. Semin Immunol. Feb. 1992;4(1):43-50.
Berer et al., Commensal gut flora and brain autoimmunity: a love or hate affair? Acta Neuropathol. May 2012;123(5):639-51. doi: 10.1007/s00401-012-0949-9. Epub Feb. 10, 2012.
Berer et al., Commensal microbiota and myelin autoantigen cooperate to trigger autoimmune demyelination. Nature. Oct. 26, 2011;479(7374):538-41. doi: 10.1038/nature10554.
Berggren et al., Decreasing serum concentrations of all-trans, 13-cis retinoic acids and retinol during fasting and caloric restriction. J Intern Med. Mar. 2003;253(3):375-80.
Bernatowska-Matuszkiewicz et al., IgG subclasses and antibody response to pneumococcal capsular polysaccharides in children with severe sinopulmonary infections and sathma. Immunol Invest. 1991;20(2):173-185.
Bettelli et al., Myelin oligodendrocyte glycoprotein-specific T cell receptor transgenic mice develop spontaneous autoimmune optic neuritis. J Exp Med. May 5, 2003;197(9):1073-81.
Bettelli et al., Reciprocal developmental pathways for the generation of pathogenic effector TH17 and regulatory T cells. Nature. May 11, 2006;441(7090):235-8. Epub Apr. 30, 2006.
Bhaduri et al., Simple and rapid method for disruption of bacteria for protein studies. Appl Environ Microbiol. Oct. 1983;46(4):941-3.
Bhat et al., Innate and adaptive autoimmunity directed to the central nervous system. Neuron. Oct. 15, 2009;64(1):123-32. doi: 10.1016/j.neuron.2009.09.015.
Bilo et al., Diagnosis of Hymenoptera venom allergy; Allergy 2005; 60:1339-1349.
Blander et al., Toll-dependent selection of microbial antigens for presentation by dendritic cells. Nature. Apr. 6, 2006;440(7085):808-12. Epub Feb. 19, 2006.
Blomfield et al. Lrp stimulates phase variation of type 1 fimbriation in *E. coli* K12. J. Bacteriology 175, 27-36, 1993.
Blumberg et al., Microbiota, disease, and back to health: a metastable journey. Sci Transl Med. Jun. 6, 2012;4(137):137rv7. doi: 10.1126/scitranslmed.3004184.
Boes et al., Accelerated development of IgG autoantibodies and autoimmune disease in the absence of secreted IgM. Proc Natl Acad Sci U S A. Feb. 1, 2000;97(3):1184-9.
Boguniewicz, M.; The autoimmune nature of chronic urticaria; Allergy Asthma Proc 2008; 29:433-438.
Bollrath et al., gp130-mediated Stat3 activation in enterocytes regulates cell survival and cell-cycle progression during colitis-associated tumorigenesis. Cancer Cell. Feb. 3, 2009;15(2):91-102. doi: 10.1016/j.ccr.2009.01.002.
Borsellino et al., Expression of ectonucleotidase CD39 by Foxp3+ Treg cells: hydrolysis of extracellular ATP and immune suppression. Blood. Aug. 15, 2007;110(4):1225-32. Epub Apr. 20, 2007.
Bouma et al., The immunological and genetic basis of inflammatory bowel disease. Nat Rev Immunol. Jul. 2003;3(7):521-33.
Bouskra et al., Lymphoid tissue genesis induced by commensals through NOD1 regulates intestinal homeostasis. Nature. Nov. 27, 2008;456(7221):507-10. doi: 10.1038/nature07450. Epub Nov. 5, 2008.
Braun et al., Body traffic: ecology, genetics, and immunity in inflammatory bowel disease. Annu Rev Pathol. 2007;2:401-29.
Bregenholt, Cells and Cytokines in the Pathogenesis of Inflammatory Bowel Disease: New Insights from Mouse T Cell Transfer Models. Exp Clin Immunogenet. Jun. 2000;17(3):115-129.
Brichford, Can You Prevent Multiple Sclerosis? Understanding factors that increase your risk of multiple sclerosis and what—if anything—you can do about them. EverydayHealth.com. Dec. 2008; 2 pages.
Brubaker et al., Mitogenic activity of purified capsular polysaccharide A from Bacteroides fragilis: differential stimulatory effect on mouse and rat lymphocytes in vitro. J Immunol. Feb. 15, 1999;162(4):2235-42.
Bruce et al., Converging pathways lead to overproduction of IL-17 in the absence of vitamin D signaling. Int Immunol. Aug. 2011;23(8):519-28. doi: 10.1093/intimm/dxr045. Epub Jun. 22, 2011.
Brunkow et al., Disruption of a new forkhead/winged-helix protein, scurfin, results in the fatal lymphoproliferative disorder of the scurfy mouse. Nat Genet. Jan. 2001;27(1):68-73.
Budinger et al., Immunologic mechanisms in hypersensitivity reactions to metal ions: an overview. Allergy. Feb. 2000;55(2):108-15. Review.
Burgers et al., The challenges of HIV vaccine development and testing. Best Pract Res Clin Obstet Gynaecol. Apr. 2005;19(2):277-91.
Cabrera et al., Influence of serum and soluble CD25 (sCD25) on regulatory and effector T-cell function in hepatocellular carcinoma. Scand J Immunol. Oct. 2010;72(4):293-301. doi: 10.1111/j.1365-3083.2010.02427.x.
Cahill et al., Inflammatory bowel disease: an immunity-mediated condition triggered by bacterial infection with Helicobacter hepaticus. Infect Immun. Aug. 1997;65(8):3126-31.
Campbell et al., The vitamin D receptor as a therapeutic target. Expert Opin Ther Targets. Oct. 2006;10(5):735-48.
Cantorna et al., 1,25-Dihydroxycholecalciferol prevents and ameliorates symptoms of experimental murine inflammatory bowel disease. J Nutr. Nov. 2000;130(11):2648-52.
Cantorna et al., Vitamin D status, 1,25-dihydroxyvitamin D3, and the immune system. Am J Clin Nutr. Dec. 2004;80(6 Suppl):1717S-20S.
Cantorna et al., 1,25-Dihydroxyvitamin D3 reversibly blocks the progression of relapsing encephalomyelitis, a model of multiple sclerosis. Proc Natl Acad Sci U S A. Jul. 23, 1996;93(15):7861-4.
Cash et al., Symbiotic bacteria direct expression of an intestinal bactericidal lectin. Science. Aug. 25, 2006;313(5790):1126-30.
Chambers et al., The impact of vitamin D on regulatory T cells. Curr Allergy Asthma Rep. Feb. 2011;11(1):29-36. doi: 10.1007/s11882-010-0161-8.
Chang et al., 1,25-Dihydroxyvitamin D3 inhibits the differentiation and migration of T(H)17 cells to protect against experimental autoimmune encephalomyelitis. PLoS One. Sep. 23, 2010;5(9):e12925. doi: 10.1371/journal.pone.0012925.
Chatila et al., Role of regulatory T cells in human diseases. J Allergy Clin Immunol. Nov. 2005;116(5):949-59; quiz 960.
Chen et al., Pertussis toxin by inducing IL-6 promotes the generation of IL-17-producing CD4 cells. J Immunol. May 15, 2007;178(10):6123-9.
Chen et al., Delivery of foreign antigens by engineered outer membrane vesicle vaccines. Proc Natl Acad Sci U S A. Feb. 16, 2010;107(7):3099-104. doi: 10.1073/pnas.0805532107. Epub Jan. 27, 2010.
Chen et al., DNA inversion on conjugative plasmid pVT745. J Bacteriol. Nov. 2002;184(21):5926-34.
Cho et al., Recent insights into the genetics of inflammatory bowel disease. Gastroenterology. May 2011;140(6):1704-12. doi: 10.1053/j.gastro.2011.02.046.

(56) References Cited

OTHER PUBLICATIONS

Chow et al., Getting the bugs out of the immune system: do bacterial microbiota "fix" intestinal T cell responses? Cell Host Microbe. Jan. 22, 2009;5(1):8-12. doi: 10.1016/j.chom.2008.12.006.

Clemente et al., Infliximab modifies mesenteric adipose tissue alterations and intestinal inflammation in rats with TNBS-induced colitis. Scand J Gastroenterol. Sep. 2012;47(8-9):943-50. doi: 10.3109/00365521.2012.688213. Epub May 28, 2012.

Cobb et al., Zwitterionic capsular polysaccharides: the new MHCII-dependent antigens. Cell Microbiol. Oct. 2005;7(10):1398-403. Review.

Collison et al., The inhibitory cytokine IL-35 contributes to regulatory T-cell function. Nature. Nov. 22, 2007;450(7169):566-9.

Comstock et al., Bacterial glycans: key mediators of diverse host immune responses. Cell. Sep. 8, 2006;126(5):847-50.

Comstock et al., Interstrain variation of the polysaccharide B biosynthesis locus of Bacteroides fragilis: characterization of the region from strain 638R. J Bacteriol. Oct. 1999;181(19):6192-6.

Comstock et al. Analysis of a capsular polysaccharide biosynthesis locus of Bacteroides fragilis. (1999) Infect Immun 67:3525-32.

Conesa et al., Interleukin-2 induces peroxide production by primed normodense eosinophils of patients with asthma. Allergy Asthma Proc. Jan.-Feb. 2003;24(1):27-33.

Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.

Coombes et al., Control of intestinal homeostasis by regulatory T cells and dendritic cells. Semin Immunol. Apr. 2007;19(2):116-26. Epub Feb. 21, 2007.

Coombes et al., Regulatory T cells and intestinal homeostasis. Immunol Rev. Apr. 2005;204:184-94.

Correale et al., Vitamin D-mediated immune regulation in multiple sclerosis. J Neurol Sci. Dec. 15, 2011;311(1-2):23-31. doi: 10.1016/j.jns.2011.06.027. Epub Jul. 2, 2011.

Couper et al., IL-10: the master regulator of immunity to infection. J Immunol. May 1, 2008;180(9):5771-7.

Coussens et al., Inflammation and cancer. Nature. Dec. 19-26, 2002;420(6917):860-7.

Coyne et al., Bacteroides fragilis NCTC9343 produces at least three distinct capsular polysaccharides: cloning, characterization, and reassignment of polysaccharide B and C biosynthesis loci. Infect Immun. Nov. 2000;68(11):6176-81.

Coyne et al. Polysaccharide biosynthesis locus required for virulence of Bacteroides fragilis. (2001) Infect Immun 69:4342-50.

Coyne et al., Mpi recombinase globally modulates the surface archtiecture of a human commensal bacterium. Proc Natl Acad Sci U S A. Sep. 2, 2003;100(18):10446-51. Epub Aug. 12, 2003.

Crabb et al., T cell regulation of Bacteroides fragilis-induced intraabdominal abscesses. Rev Infect Dis. Jan.-Feb. 1990;12 Suppl 2:S178-84. Review.

Craig, Autologous hematopoietic stem cell transplantation for Crohn's disease. Autoimmun Rev. Aug. 2002;1(4):244-9. Review.

Dadley-Moore, The sweet side of maturation. Nature Rev Immunol. Sep. 2005;5:674.

Dahiyat et al., De novo protein design: fully automated sequence selection .Science (1997) 278:82-87.

Daniel et al., Immune modulatory treatment of trinitrobenzene sulfonic acid colitis with calcitriol is associated with a change of a T helper (Th) 1/Th17 to a Th2 and regulatory T cell profile. J Pharmacol Exp Ther. Jan. 2008;324(1):23-33. Epub Oct. 2, 2007

Deib, Treating multiple sclerosis with monoclonal antibodies: a 2013 update. Expert Rev Neurother. Mar. 2013;13(3):313-35. doi: 10.1586/ern.13.17.

Denning et al., Lamina propria macrophages and dendritic cells differentially induce regulatory and interleukin 17-producing T cell responses. Nat Immunol. Oct. 2007;8(10):1086-94. Epub Sep. 16, 2007.

Deslongchamps et al., Ozonolysis of Acetals. (1) Ester Synthesis, (2) THP Ether Cleavage, (3) Selective Oxidation of β-Glycoside, (4) Oxidative Removal of Benzylidene and Ethylidene Protecting Groups. Canadian J of Chem. 1971;49:2465-2467.

Deslongchamps et al., The Importance of Conformation in the Ozonolysis of Acetals. Canadian J Chem. 1972;50:3402-3404.

Deslongchamps et al., The Oxidation of Acetals by Ozone. Canadian J Chem. 1974;52:3651-3664.

Dethlefsen et al., An ecological and evolutionary perspective on human-microbe mutualism and disease. Nature. Oct. 18, 2007;449(7164):811-8.

Dias et al., Antisense oligonucleotides: Basic concepts and mechanisms. Mol. Cancer Therap., 2002, vol. 1: 347-355.

Difabio et al., Structure of the Capsular Polysaccharide Antigen of Type IV Group B *Streptococcus*; Can. J. Chem. 67:877 (1989).

Doig et al., The efficacy of the heat killing of *Mycobacterium tuberculosis*. J Clin Pathol. Oct. 2002;55(10):778-9.

Dong, Diversification of T-helper-cell lineages: finding the family root of IL-17-producing cells. Nat Rev Immunol. Apr. 2006;6(4):329-33.

Dooms et al., Revisiting the role of IL-2 in autoimmunity. Eur J Immunol. Jun. 2010;40(6):1538-40. doi: 10.1002/eji.201040617.

Duerr et al., A genome-wide association study identifies IL23R as an inflammatory bowel disease gene. Science. Dec. 1, 2006;314(5804):1461-3. Epub Oct. 26, 2006.

Eisenstein et al. Integration host factor is required for the DNA inversion that controls phase variation in *E. coli*. Proc Natl. Acad. Sci. 84, 6506-6510, 1987.

Elson, Commensal bacteria as targets in Crohn's disease. Gastroenterology. Jul. 2000;119(1):254-7.

Elson et al., Monoclonal anti-interleukin 23 reverses active colitis in a T cell-mediated model in mice. Gastroenterology. Jun. 2007;132(7):2359-70. Epub Apr. 13, 2007.

Falk et al., Creating and maintaining the gastrointestinal ecosystem: what we know and need to know from gnotobiology. Microbiol Mol Biol Rev. Dec. 1998;62(4):1157-70.

Feuerer et al., Foxp3+ regulatory T cells: differentiation, specification, subphenotypes. Nat Immunol. Jul. 2009;10(7):689-95. doi: 10.1038/ni.1760.

Finberg et al., Decay-accelerating factor expression on either effector or target cells inhibits cytotoxicity by human natural killer cells. J Immunol. Sep. 15, 1992;149(6):2055-60.

Fink et al., Human antigen-presenting cells respond differently to gut-derived probiotic bacteria but mediate similar strain-dependent NK and T cell activation. FEMS Immunol Med Microbiol. Dec. 2007;51(3):535-46. Epub Sep. 27, 2007.

Fontenot et al., Regulatory T cell lineage specification by the forkhead transcription factor foxp3. Immunity. Mar. 2005;22(3):329-41.

Fontenot et al., Foxp3 programs the development and function of CD4+CD25+ regulatory T cells. Nat Immunol. Apr. 2003;4(4):330-6. Epub Mar. 3, 2003.

Fournier et al., Isolation of type 5 capsular polysaccharide from *Staphylococcus aureus*. Ann Inst Pasteur Microbiol. Sep.-Oct. 1987;138(5):561-7.

Frank et al., Molecular-phylogenetic characterization of microbial community imbalances in human inflammatory bowel diseases. Proc Natl Acad Sci U S A. Aug. 21, 2007;104(34):13780-5. Epub Aug. 15, 2007.

Fridkis-Hareli et al., Binding motifs of copolymer 1 to multiple sclerosis- and rheumatoid arthritis-associated HLA-DR molecules. J Immunol. Apr. 15, 1999;162(8):4697-704.

Fridkis-Hareli et al., Binding of random copolymers of three amino acids to class II MHC molecules. Int Immunol. May 1999;11(5):635-41.

Fridkis-Hareli et al., Direct binding of myelin basic protein and synthetic copolymer 1 to class II major histocompatibility complex molecules on living antigen-presenting cells—specificity and promiscuity. Proc Natl Acad Sci U S A. May 24, 1999;91(11):4872-6.

Fridkis-Hareli et al., Synthetic copolymer 1 and myelin basic protein do not require processing prior to binding to class II major histocompatibility complex molecules on living antigen-presenting cells. Cell Immunol. Jul. 1995;163(2):229-36.

(56) References Cited

OTHER PUBLICATIONS

Froicu et al., A crucial role for the vitamin D receptor in experimental inflammatory bowel diseases. Mol Endocrinol. Dec. 2003;17(12):2386-92. Epub Sep. 18, 2003.
Froicu et al., Vitamin D receptor is required to control gastrointestinal immunity in IL-10 knockout mice. Immunology. Mar. 2006;117(3):310-8.
Fukuoka et al., Physico-chemical analysis of lipid A fractions of lipopolysaccharide from Erwinia carotovora in relation to bioactivity. Biochimica et Biophysica Acta. 2001;1510(1):185-97.
Gaboriau-Routhiau et al., The key role of segmented filamentous bacteria in the coordinated maturation of gut helper T cell responses. Immunity. Oct. 16, 2009;31(4):677-89. doi: 10.1016/j.immuni.2009.08.020.
Gally et al. Environmental regulation of the fim switch controlling type 1 fimbrial phase variation in *Escherichia coli* K-12: effects of temperature and media. (1993) J Bacteriol 175:6186-93.
Garrett et al., Colitis-associated colorectal cancer driven by T-bet deficiency in dendritic cells. Cancer Cell. Sep. 8, 2009;16(3):208-19. doi: 10.1016/j.ccr.2009.07.015.
Garrett et al., Enterobacteriaceae act in concert with the gut microbiota to induce spontaneous and maternally transmitted colitis. Cell Host Microbe. Sep. 16, 2010;8(3):292-300. doi: 10.1016/j.chom.2010.08.004.
Gelu-Simeon, et al., Evaluation and predictive factors of thyroid disorder due to interferon alpha in the treatment of hepatitis C. World J Gastroenterol 2009; 15(3):328-333.
Gerard et al., Interleukin 10 reduces the release of tumor necrosis factor and prevents lethality in experimental endotoxemia. J Exp Med. Feb. 1, 1993;177(2):547-50.
Gibson et al., Cellular mechanism of intraabdominal abscess formation by Bacteroides fragilis. J Immunol. May 15, 1998;160(10):5000-6.
Gibson et al., Chapter 5: trans-Galactooligosaccharides as Prebiotics. Handbook of Functional Dairy Products. Edited by Colette Shortt and John O'Brien. Published by CRC Press. 2004. pp. 91-108.
Gibson et al., The capsular polysaccharide complex of Bacteroides fragilis induces cytokine production from human and murine phagocytic cells. Infect Immun. 1996 Mar.;64(3):1065-9.
Gill et al., Metagenomic analysis of the human distal gut microbiome. Science. Jun. 2, 2006;312(5778):1355-9.
Glazebrook et al., A novel exopolysaccharide can function in place of the calcofluor-binding exopolysaccharide in nodulation of alfalfa by Rhizobium meliloti. Cell. Feb. 24, 1989;56(4):661-72.
Golgher et al., Galactofuranose-containing glycoconjugates of epimastigote and trypomastigote forms of Trypanosoma cruzi. Mol Biochem Parasitol. Aug. 1993;60(2):249-64.
Gondek et al., Cutting edge: contact-mediated suppression by CD4+CD25+ regulatory cells involves a granzyme B-dependent, perforin-independent mechanism. J Immunol. Feb. 15, 2005;174(4):1783-6.
Gonzalez-Hernandez et al., Peripheral blood CD161+ T cells from asthmatic patients are activated during asthma attack and predominantly produce IFN-gamma. Scand J Immunol. Apr. 2007;65(4):368-75.
Goverman Autoimmune T cell responses in the central nervous system. Nat Rev Immunol. Jun. 2009;9(6):393-407. doi: 10.1038/nri2550.
Goverman et al., Transgenic mice that express a myelin basic protein-specific T cell receptor develop spontaneous autoimmunity. Cell. Feb. 26, 1993;72(4):551-60.
Grabow, Bacteriophages: Update on application as models for viruses in water. Water SA 2001;27(2):251-268.
Greenberger, P.A.; Drug allergy. J Allergy Clin Immunol 2006; 117(2):S464-S470.
Groux et al., A CD4+ T-cell subset inhibits antigen-specific T-cell responses and prevents colitis. Nature. Oct. 16, 1997;389(6652):737-42.
Groux et al., Type I T-regulatory cells: their role in the control of immune responses. Transplantation. May 15, 2003;75(9 Suppl):8S-12S.
Grivennikov et al., IL-6 and Stat3 are required for survival of intestinal epithelial cells and development of colitis-associated cancer. Cancer Cell. Feb. 3, 2009;15(2):103-13. doi: 10.1016/j.ccr.2009.01.001.
Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.
Hall et al., Commensal DNA limits regulatory T cell conversion and is a natural adjuvant of intestinal immune responses. Immunity. Oct. 17, 2008;29(4):637-49. doi: 10.1016/j.immuni.2008.08.009. Epub Oct. 2, 2008
Hamelmann et al., Noninvasive measurement of airway responsiveness in allergic mice using barometric plethysmography. Am J Respir Crit Care Med. Sep. 1997;156(3 Pt 1):766-75.
Hampe et al., A genome-wide association scan of nonsynonymous SNPs identifies a susceptibility variant for Crohn disease in ATG16L1. Nat Genet. Feb. 2007;39(2):207-11. Epub Dec. 31, 2006.
Hampe et al., Association between insertion mutation in NOD2 gene and Crohn's disease in German and British populations. Lancet. Jun. 16, 2001;357(9272):1925-8.
Haregewoin et al., Human gamma delta+ T cells respond to mycobacterial heat-shock protein.Nature. Jul. 27, 1989;340(6231):309-12.
Harth et al. Treatment of *Mycobacterium tuberculosis* with antisense oligonucleotides to glutamine synthetase mRNA inhibits glutamine synthetase activity, formation of poly-L-glutamate/glutamine cell wall structure, and bacterial replication. Proc Natl. Acad. Sci. 97: 418-423, 2000.
He et al., Intestinal bacteria trigger T cell-independent immunoglobulin A(2) class switching by inducing epithelial-cell secretion of the cytokine APRIL. Immunity. Jun. 2007;26(6):812-26.
Hertl et al., T cell control in autoimmune bullous skin disorders. J Clin Invest. May 2006;116(5):1159-66. Review.
Hewison et al., Differential regulation of vitamin D receptor and its ligand in human monocyte-derived dendritic cells. J Immunol. Jun. 1, 2003;170(11):5382-90.
Hirata et al., Cytokine synthesis of human monocytes stimulated by triple or single helical conformer of an antitumour $(1\rightarrow3)$-beta-D-glucan preparation, sonifilan. Zentralbl Bakteriol. Nov. 1998;288(3):403-13.
Hodge et al., *Allium sativum* (garlic) suppresses leukocyte inflammatory cytokine production in vitro: potential therapeutic use in the treatment of inflammatory bowel disease. Cytometry. Aug. 1, 2002;48(4):209-15.
Hofstetter et al., Th17 Cells in MS and Experimental Autoimmune Encephalomyelitis. Int MS J. Apr. 2009;16(1):12-8.
Hooper, Do symbiotic bacteria subvert host immunity? Nat Rev Microbiol. May 2009;7(5):367-74. doi: 10.1038/nrmicro2114.
Hooper et al., Commensal host-bacterial relationships in the gut. Science. May 11, 2001;292(5519):1115-8.
Hori et al., Control of regulatory T cell development by the transcription factor Foxp3. Science. Feb. 14, 2003;299(5609):1057-61. Epub Jan. 9, 2003.
Horstman et al., Enterotoxigenic *Escherichia coli* secretes active heat-labile enterotoxin via outer membrane vesicles. J Biol Chem. Apr. 28, 2000;275(17):12489-96.
Hu et al., Inflammation-induced tumorigenesis in the colon is regulated by caspase-1 and NLRC4. Proc Natl Acad Sci U S A. Dec. 14, 2010;107(50):21635-40. doi: 10.1073/pnas.1016814108. Epub Nov. 30, 2010.
Hue et al., Interleukin-23 drives innate and T cell-mediated intestinal inflammation. J Exp Med. Oct. 30, 2006;203(11):2473-83. Epub Oct. 9, 2006.
Huibregtse et al.., Immunopathogenesis of IBD: insufficient suppressor function in the gut? Gut. Apr. 2007;56(4):584-92. Epub Oct. 17, 2006.
Hutloff et al., ICOS is an inducible T-cell co-stimulator structurally and functionally related to CD28. Nature. Jan. 21, 1999;397(6716):263-6.

(56) References Cited

OTHER PUBLICATIONS

Isaksson et al., Conditional DC depletion does not affect priming of encephalitogenic Th cells in EAE. Eur J Immunol. Oct. 2012;42(10):2555-63. doi: 10.1002/eji.201142239. Epub Aug. 8, 2012.
Ishikawa et al., Effect of intestinal microbiota on the induction of regulatory CD25+ CD4+ T cells. Clin Exp Immunol. Jul. 2008;153(1):127-35. doi: 10.1111/j.1365-2249.2008.03668.x. Epub May 5, 2008.
Itokazu et al., Abscess formation as a complication caused by postoperative osteomyelitis of the femur. Arch Orthop Trauma Surg. 1998;118(1-2):99-102. Review.
Itzkowitz et al., Diagnosis and management of dysplasia in patients with inflammatory bowel diseases. Gastroenterology. May 2004;126(6):1634-48.
Ivanov et al., Transcriptional regulation of Th17 cell differentiation. Semin Immunol. Dec. 2007;19(6):409-17. Epub Nov. 28, 2007.
Ivanov et al., The orphan nuclear receptor RORgammat directs the differentiation program of proinflammatory IL-17+ T helper cells. Cell. Sep. 22, 2006;126(6):1121-33.
Ivanov et al., Induction of intestinal Th17 cells by segmented filamentous bacteria. Cell. Oct. 30, 2009;139(3):485-98. doi: 10.1016/j.cell.2009.09.033.
Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom.2008.09.009.
Izcue et al., Regulatory T cells suppress systemic and mucosal immune activation to control intestinal inflammation. Immunol Rev. Aug. 2006;212:256-71.
Jawad et al., Inflammatory bowel disease and colon cancer. Recent Results Cancer Res. 2011;185:99-115. doi: 10.1007/978-3-642-03503-6_6.
Jeffery et al., 1,25-Dihydroxyvitamin D3 and IL-2 combine to inhibit T cell production of inflammatory cytokines and promote development of regulatory T cells expressing CTLA-4 and FoxP3. J Immunol. Nov. 1, 2009;183(9):5458-67. doi: 10.4049/jimmunol.0803217.
Jennings et al., Immunochemistry of groups A, B, and C meningococcal polysaccharide-tetanus toxoid conjugates. J Immunol. Sep. 1981;127(3):1011-8.
Jennings et al., Induction of meningococcal group B polysaccharide-specific IgG antibodies in mice by using an N-propionylated B polysaccharide-tetanus toxoid conjugate vaccine. J Immunol. Sep. 1, 1086;137(5):1708-13.
Jennings et al., Structure of the Complex Polysaccharide C-Substance from *Streptococcus pneumoniae* Type 1; Biochem. 19:4712-4719 (1980).
Jia et al., Gut microbiota: a potential new territory for drug targeting. Nat Rev Drug Discov. Feb. 2008;7(2):123-9. doi: 10.1038/nrd2505.
Johnson et al., Bacterial capsular polysaccharide prevents the onset of asthma through T-cell activation. Glycobiology. Apr. 2015;25(4):368-75. doi: 10.1093/glycob/cwu117. Epub Oct. 27, 2014.
Jonuleit et al., Identification and functional characterization of human CD4(+)CD25(+) T cells with regulatory properties isolated from peripheral blood. J Exp Med. Jun. 4, 2001;193(11):1285-94.
Jonuleit et al., The regulatory T cell family: distinct subsets and their interrelations. J Immunol. Dec. 15, 2003;171(12):6323-7.
Joshi et al., 1,25-dihydroxyvitamin D(3) ameliorates Th17 autoimmunity via transcriptional modulation of interleukin-17A. Mol Cell Biol. Sep. 2011;31(17):3653-69. doi: 10.1128/MCB.05020-11. Epub Jul. 11, 2011.
Jotwani et al., Pathogenicity of Bacteroides fragilis group in rat intra-abdominal abscesses. Microbiol Immunol. 1992;36(10):1041-9.
Jyonouchi, H.; Non-IgE Mediated Food Allergy; Inflammation & Allergy—Drug Targets 2008; 7(3):1-8.

Kakalacheva et al., Viral triggers of multiple sclerosis. Biochim Biophys Acta. Feb. 2011;1812(2):132-40. doi: 10.1016/j.bbadis.2010.06.012. Epub Jun. 25, 2010.
Kakalacheva et al., Environmental triggers of multiple sclerosis. FEBS Lett. Dec. 1, 2011;585(23):3724-9. doi: 10.1016/j.febslet.2011.04.006. Epub Apr. 7, 2011.
Kalka-Moll et al., Bacteriodes Fragilis NCTC 9343 Capsular Polysaccharide PS A and the Effect of Chain Length of T cell Proliferation. Abstracts of the 98th Gen Mtg of the American Soc for Microbiol. 1998;98:123. Abstract B-405.
Kalka-Moll et al., Immunochemical and biological characterization of three capsular polysaccharides from a single Bacteroides fragilis strain. Infect Immun. Apr. 2001;69(4):2339-44.
Kalka-Moll et al., Effect of molecular size on the ability of zwitterionic polysaccharides to stimulate cellular immunity. J Immunol. Jan. 15, 2000;164(2):719-24.
Kalka-Moll, et al., Zwitterionic Polysaccharides Stimulate T Cells by MHC Class II-Dependent Interactions; J. Immunol.; 2002;169:6149-6153.
Kasper et al., Capsular polysaccharides and lipopolysaccharides from two Bacteroides fragilis reference strains: chemical and immunochemical characterization. J Bacteriol. Feb. 1983;153(2):991-7.
Kasper et al., Protective efficacy of immunization with capsular antigen against experimental infection with Bacteroides fragilis. J Infect Dis. Nov. 1979;140(5):724-31.
Kasper et al., Surface antigens as virulence factors in infection with Bacteroides fragilis. Rev Infect Dis. Mar.-Apr. 1979;1(2):278-90.
Kasper et al., The polysaccharide capsule of *Bacteroides fragilis* subspecies *fragilis*: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kenne et al., Structural studies of the O-specific side-chains of the Shigella sonnei phase I lipopolysaccharide. Carbohydrate Res. 1980;78:119-126.
Kennedy et al., Prevention of experimental postoperative peritoneal adhesions by N,O-carboxymethyl chitosan. Surgery. Nov. 1996;120(5):866-70.
Kernodle et al. Expression of an antisense hla fragment in *Staphylococcus aureus* reduces alpha-toxin production in vitro and attenuates lethal activity in a murine model. Infection and Immunity 179-184. 1997.
Kesty et al., Incorporation of heterologous outer membrane and periplasmic proteins into *Escherichia coli* outer membrane vesicles. J Biol Chem. Jan. 16, 2004;279(3):2069-76. Epub Oct. 24, 2003.
Kidd, Th1/Th2 balance: the hypothesis, its limitations, and implications for health and disease. Altern Med Rev. Aug. 2003;8(3):223-46.
Kim et al., Regulatory T cells prevent catastrophic autoimmunity throughout the lifespan of mice. Nat Immunol. Feb. 2007;8(2):191-7. Epub Nov. 30, 2006.
Kinoshita et al., Retinoic acid reduces autoimmune renal injury and increases survival in NZB/W F1 mice. J Immunol. Jun. 1, 2003;170(11):5793-8.
Kirjavainen et al., Healthy gut microflora and allergy: factors influencing development of the microbiota. Ann Med. Aug. 1999;31(4):288-92.
Knetsch et al., Polymers with tunable toxicity: a reference scale for cytotoxicity testing of biomaterial surfaces. J Biomed Mater Res A. Sep. 15, 2007;82(4):947-57.
Knirel et al., Somatic antigens of Pseudomonas aeruginosa. The structure of O-specific polysaccharide chains of lipopolysaccharides of P. aeruginosa O3 (Lanyi), O25 (Wokatsch) and Fisher immunotypes 3 and 7. Eur J Biochem. Sep. 15, 1987;167(3):549-61.
Knirel et al., The structure of O-specific polysaccharides and serological classification of Pseudomonas aeruginosa (a review). Acta Microbiol Hung. 1988;35(1):3-24. Review.
Koch et al., The transcription factor T-bet controls regulatory T cell homeostasis and function during type 1 inflammation. Nat Immunol. Jun. 2009;10(6):595-602. doi: 10.1038/ni.1731. Epub May 3, 2009.

(56) References Cited

OTHER PUBLICATIONS

Kong et al., Novel role of the vitamin D receptor in maintaining the integrity of the intestinal mucosal barrier. Am J Physiol Gastrointest Liver Physiol. Jan. 2008;294(1):G208-16. Epub Oct. 25, 2007.
Kormelink et al.; Atopic and non-atopic allergic disorders: current insights into the possible involvement of free immunoglobulin light chains; Clinical and Experimental Allergy 2008; 39:33-42.
Krause et al., An Inhibitor of Cell Proliferation Associated with Adhesion Formation Is Suppressed by N,O-Carboxymethyl Chitosan. J Invest Surg. 1988;11:105-113.
Krinos et al., Extensive surface diversity of a commensal microorganism by multiple DNA inversions. (2001) Nature 414:555-8.
Krutzik et al., IL-15 links TLR2/1-induced macrophage differentiation to the vitamin D-dependent antimicrobial pathway. J Immunol. Nov. 15, 2008;181(10):7115-20.
Kuehn et al., Bacterial outer membrane vesicles and the host-pathogen interaction. Genes Dev. Nov. 15, 2005;19(22):2645-55.
Kuhn et al., Interleukin-10-deficient mice develop chronic enterocolitis. Cell. Oct. 22, 1993;75(2):263-74.
Kulberg et al., Bacteria-triggered CD4(+) T regulatory cells suppress Helicobacter hepaticus-induced colitis. J Exp Med. Aug. 19, 2002;196(4):505-15.
Kulberg et al., IL-23 plays a key role in Helicobacter hepaticus-induced T cell-dependent colitis. J Exp Med. Oct. 30, 2006;203(11):2485-94. Epub Oct. 9, 2006.
Kulberg et al., Induction of colitis by a CD4+ T cell clone specific for a bacterial epitope. Proc Natl Acad Sci U S A. Dec. 23, 2003;100(26):15830-5. Epub Dec. 12, 2003.
Kulberg et al., Helicobacter hepaticus triggers colitis in specific-pathogen-free interleukin-10 (IL-10)-deficient mice through an IL-12- and gamma interferon-dependent mechanism. Infect Immun. Nov. 1998;66(11):5157-66.
Kulicke et al., Correlation between immunological activity, molar mass, and molecular structure of different (1→3)-beta-D-glucans. Carbohydr Res. Jan. 2, 1997;297(2):135-43.
Kuper et al., Infections as a major preventable cause of human cancer. J Intern Med. Sep. 2000;248(3):171-83.
Kurup et al., Antibody response to low-molecular-weight antigens of Aspergillus fumigatus in allergic bronchopulmonary aspergillosis. J Clin Microbiol. Jun. 1989;27(6):1312-6.
Lagishetty et al., Vitamin D deficiency in mice impairs colonic antibacterial activity and predisposes to colitis. Endocrinology. Jun. 2010;151(6):2423-32. doi: 10.1210/en.2010-0089. Epub Apr. 14, 2010.
Lee et al., Bacterial colonization factors control specificity and stability of the gut microbiota. Nature. Sep. 19, 2013;501(7467):426-9. doi: 10.1038/nature12447. Epub Aug. 18, 2013.
Lee et al., Proinflammatory T-cell responses to gut microbiota promote experimental autoimmune encephalomyelitis. Proc Natl Acad Sci U S A. Mar. 15, 2011;108 Suppl 1:4615-22. doi: 10.1073/pnas.1000082107. Epub Jul. 16, 2010.
Lee et al., Has the microbiota played a critical role in the evolution of the adaptive immune system? Science. Dec. 24, 2010;330(6012):1768-73. doi: 10.1126/science.1195568.
Lee et al., Effects of In Vitro and In Vivo and Growth Conditions on Expression of Type 8 Capsular Polysaccharide by *Staphylococcus aureus*, Infection and Immunity, 61:1853-1858, 1993.
Ley et al., Ecological and evolutionary forces shaping microbial diversity in the human intestine. Cell. Feb. 24, 2006;124(4):837-48.
Ley et al., Evolution of mammals and their gut microbes. Science. Jun. 20, 2008;320(5883):1647-51. doi: 10.1126/science.1155725. Epub May 22, 2008.
Lin et al., Regulatory T cell development in the absence of functional Foxp3. Nat Immunol. Apr. 2007;8(4):359-68. Epub Feb. 2, 2007.
Lindberg et al., Structural Studies of the Capsular Polysaccharide from *Streptococcus pneumoniae* Type 1; Carbohydrate Res 78:111-117 (1980).
Lindberg et al., Virulence factors in infections with bacteroides fragilis: isolation and characterization of capsular polysaccharide and lipopolysaccharide. Scand J Infect Dis Suppl. 1982;35:45-52.
Liu et al., Altered endocrine and autocrine metabolism of vitamin D in a mouse model of gastrointestinal inflammation. Endocrinology. Oct. 2008;149(10):4799-808. doi: 10.1210/en.2008-0060. Epub Jun. 5, 2008.
Liu et al., Toll-like receptor 2 signaling modulates the functions of CD4+ CD25+ regulatory T cells. Proc Natl Acad Sci U S A. May 2, 2006;103(18):7048-53. Epub Apr. 21, 2006.
Liu et al., Regulation of surface architecture by symbiotic bacteria mediates host colonization. Proc Natl Acad Sci U S A. Mar. 11, 2008;105(10):3951-6. doi: 10.1073/pnas.0709266105. Epub Mar. 4, 2008.
Liu et al., Toll-like receptor triggering of a vitamin D-mediated human antimicrobial response. Science. Mar. 24, 2006;311(5768):1770-3. Epub Feb. 23, 2006.
Lysnyansky et al. Juxtaposition of an active promoter to vsp genes via site-specific DNA inversions generates antigenic variation in Mycoplasma bovis. (2001) J Bacteriol 183:5698-5708.
Maconi et al., Contrast radiology, computed tomography, and ultrasonography in detecting internal fistulas and intra-abdominal abscesses in Chrohn's disease: a prospective comparative study. Amer J Gast. 2003;98(7):1545-1555.
Macpherson et al., Interactions between commensal intestinal bacteria and the immune system. Nat Rev Immunol. Jun. 2004;4(6):478-85.
Macpherson et al., IgA responses in the intestinal mucosa against pathogenic and nonpathogenic microorganisms. Microbes Infect. Oct. 2001;3(12):1021-35.
Macpherson et al., Mucosal antibodies in inflammatory bowel disease are directed against intestinal bacteria. Gut. Mar. 1996;38(3):365-75.
Macpherson et al., Induction of protective IgA by intestinal dendritic cells carrying commensal bacteria. Science. Mar. 12, 2004;303(5664):1662-5.
Maier et al., Experimental Shigella infections in laboratory animals. I. Antagonism by human normal flora components in gnotobiotic mice. Infect Immun. Aug. 1972;6(2):168-73.
Makela et al., IL-10 is necessary for the expression of airway hyperresponsiveness but not pulmonary inflammation after allergic sensitization. Proc Natl Acad Sci U S A. May 23, 2000;97(11):6007-12.
Maloy et al., CD4+CD25+ T(R) cells suppress innate immune pathology through cytokine-dependent mechanisms. J Exp Med. Jan. 6, 2003;197(1):111-9.
Mamessier et al., Cytokines in atopic diseases: revisiting the Th2 dogma. Eur J Dermatol. Mar.-Apr. 2006;16(2):103-13. Review.
Mancuso et al., Bacteroides fragilis-derived lipopolysaccharide produces cell activation and lethal toxicity via toll-like receptor 4. Infect Immun. Sep. 2005;73(9):5620-7.
Mantovani et al., Cancer-related inflammation. Nature. Jul. 24, 2008;454(7203):436-44. doi: 10.1038/nature07205.
Maynard et al., Diversity in the contribution of interleukin-10 to T-cell-mediated immune regulation. Immunol Rev. Dec. 2008;226:219-33. doi: 10.1111/j.1600-065X.2008.00711.x.
Maynard et al., Contrasting roles for all-trans retinoic acid in TGF-beta-mediated induction of Foxp3 and Il10 genes in developing regulatory T cells. J Exp Med. Feb. 16, 2009;206(2):343-57. doi: 10.1084/jem.20080950. Epub Feb. 9, 2009.
Maynard et al., Regulatory T cells expressing interleukin 10 develop from Foxp3+ and Foxp3− precursor cells in the absence of interleukin 10. Nat Immunol. Sep. 2007;8(9):931-41. Epub Aug. 12, 2007.
Mayne et al., 1,25-Dihydroxyvitamin D3 acts directly on the T lymphocyte vitamin D receptor to inhibit experimental autoimmune encephalomyelitis. Eur J Immunol. Mar. 2011;41(3):822-32. doi: 10.1002/eji.201040632. Epub Feb. 1, 2011.
Mazmanian et al., An immunomodulatory molecule of symbiotic bacteria directs maturation of the host immune system. Cell. Jul. 15, 2005;122(1):107-18.
Mazmanian et al., Bacterial immunomodulatory regulation during mammalian health and disease. Harvard Medical School and Brigham and Women's Hospital. Presentation. Oct. 11, 2005. 51 pages.

(56) References Cited

OTHER PUBLICATIONS

Mazmanian et al., Host-bacterial symbiosis prevents intestinal inflammatory disease. California Institute of Technology. Presentation. Amgen. Jul. 2008. 47 pages.
Mazmanian et al., The evolution of symbiosis: from bacteria to commensal to beneficial microbe. Harvard Medical School and California Institute of Technology. Presentation. Oct. 4, 2006. 24 pages.
Mazmanian et al., The love-hate relationship between bacterial polysaccharides and the host immune system. Nature Reviews Immunology. 2006;6: 849-858.
Mazmanian et al., Capsular polysaccharides of symbiotic bacteria modulate immune responses during experimental colitis. J Pediatr Gastroenterol Nutr. Apr. 2008;46 Suppl 1:E11-2. doi: 10.1097/01.mpg.0000313824.70971.a7.
Mazmanian et al., A microbial symbiosis factor prevents intestinal inflammatory disease. Nature. May 29, 2008;453(7195):620-5. doi: 10.1038/nature07008.
Mcclain et al. Inversion-independent phase variation of type 1 fimbriae in *Escherichia coli*. (1993) J Bacteriol 175(14):4335-44.
Mcmurchy et al., Suppression assays with human T regulatory cells: a technical guide. Eur J Immunol. Jan. 2012;42(1):27-34. doi: 10.1002/eji.201141651. Epub Dec. 12, 2011.
Meisel-Mikolajczyk et al., Human T cell adhesion to endothelium stimulated by membrane components extracted from strains of Bacteroides vulgatus (member of B. fragilis group). Arch Immunol Ther Exp (Warsz). 1993;41(2):129-31.
Mertens et al., *Streptococcus pneumoniae* serotype 1 capsular polysaccharide induces CD8 CD28 regulatory T lymphocytes by TCR crosslinking. PLoS Pathog. Sep. 2009;5(9):e1000596. doi: 10.1371/journal.ppat.1000596. Epub Sep. 25, 2009.
Miller et al., Severe asthma and the omalizumab option. Clinical and Molecular Allergy 2008, 6:4.
Min et al., Gut flora antigens are not important in the maintenance of regulatory T cell heterogeneity and homeostasis. Eur J Immunol. Jul. 2007;37(7):1916-23.
Mojtabavi et al., Long-lived Th2 memory in experimental allergic asthma. J Immunol. Nov. 1, 2002;169(9):4788-96.
Montz et al., Interleukin 10: ability to minimize postoperative intraperitoneal adhesion formation in a murine model. Fertil Steril. Jun. 1994;61(6):1136-40.
Moore, The List Goes on, New Additions to the Autoimmune Disease Roster. http://autoimmunedisease.suite101.com/blog.cfm/the_list_goes_on. pp. 1-3.
Moorman et al., National Surveillance of Asthma: United States, 2001-2010. National Center for Health Statistics. Vital Health Stat. 2012;3(35) 67 pages.
Mor et al., Identification of aldolase as a target antigen in Alzheimer's disease. J Immunol. Sep. 1, 2005;175(5):3439-45.
Mora et al., Generation of gut-homing IgA-secreting B cells by intestinal dendritic cells. Science. Nov. 17, 2006;314(5802):1157-60.
Mora et al., Selective imprinting of gut-homing T cells by Peyer's patch dendritic cells. Nature. Jul. 3, 2003;424(6944):88-93.
Morales-Tirado et al., 1α,25-dihydroxyvitamin D3 (vitamin D3) catalyzes suppressive activity on human natural regulatory T cells, uniquely modulates cell cycle progression, and augments FOXP3. Clin Immunol. Feb. 2011;138(2):212-21. doi: 10.1016/j.clim.2010.11.003. Epub Dec. 16, 2010.
Motta et al., T cells in asthma: Lessons from mouse models. Drug Discovery Today; Disease Models. 2006;3(3):199-204.
Mulholland et al., Strategies for the control of pneumococcal diseases. Vaccine. Jul. 30, 1999;17 Suppl 1:S79-84. Review.
Nakayama-Imaohji et al., Identification of the site-specific DNA invertase responsible for the phase variation of SusC/SusD family outer membrane proteins in Bacteroides fragilis. J Bacteriol. Oct. 2009;191(19):6003-11. doi: 10.1128/JB.00687-09. Epub Jul. 31 2009.

Natori et al., Agelasphins, novel antitumor and immunostimulatory cerebrosides from the marine sponge *Agelas mauritianus*. Tetrahedron. 1994;50(9):2771-2784.
Neurath et al., TNBS-colitis. Int Rev Immunol. 2000;19(1):51-62.
Nielsen et al., Applications of peptide nucleic acids. Curr Opin Biotechnol. Feb. 1999;10(1):71-5. Review.
Niess et al., Commensal gut flora drives the expansion of proinflammatory CD4 T cells in the colonic lamina propria under normal and inflammatory conditions. J Immunol. Jan. 1, 2008;180(1):559-68.
Norman; "Thyroiditis—Inflammation of the thyroid gland"; Endocrineweb 2009; www.endocrineweb.com/throiditis.html, 1-4. Downloaded Jul. 28, 2009.
Noverr et al., Does the microbiota regulate immune responses outside the gut? Trends Microbiol. Dec. 2004;12(12):562-8.
Nylander et al., Multiple sclerosis. J Clin Invest. Apr. 2012;122(4):1180-8. doi: 10.1172/JCI58649. Epub Apr. 2, 2012.
O'Connor et al., Translational mini-review series on Th17 cells: CD4 T helper cells: functional plasticity and differential sensitivity to regulatory T cell-mediated regulation. Clin Exp Immunol. Feb. 2010;159(2):137-47. doi: 10.1111/j.1365-2249.2009.04040.x. Epub Nov. 11, 2009.
O'Garra et al., IL-10-producing and naturally occurring CD4+ Tregs: limiting collateral damage. J Clin Invest. Nov. 2004;114(10):1372-8.
O'Hara et al., The gut flora as a forgotten organ. EMBO Rep. Jul. 2006;7(7):688-93.
Ochoa-Reparaz et al., Central nervous system demyelinating disease protection by the human commensal Bacteroides fragilis depends on polysaccharide A expression. J Immunol. Oct. 1, 2010;185(7):4101-8. doi: 10.4049/jimmunol.1001443. Epub Sep. 3, 2010.
Ochoa-Reparaz, J. et al., The role of subcellular fractions of commensal Bacteroides fragilis in the control of experimental autoimmune encephalomyelitis. Multiple Sclerosis. 2009;15:S61. Poster P236.
Ochoa-Reparaz et al., Role of gut commensal microflora in the development of experimental autoimmune encephalomyelitis. J Immunol. Nov. 15, 2009;183(10):6041-50. doi: 10.4049/jimmunol.0900747. Epub Oct. 19, 2009.
Ochoa-Reparaz et al., A polysaccharide from the human commensal Bacteroides fragilis protects against CNS demyelinating disease. Mucosal Immunol. Sep. 2010;3(5):487-95. doi: 10.1038/mi.2010.29. Epub Jun. 9, 2010.
Oda et al., A comprehensive map of the toll-like receptor signaling network. Mol Syst Biol. 2006;2:2006.0015. Epub Apr. 18, 2006.
Oh et al., CD4 T-helper cells engineered to produce IL-10 prevent allergen-induced airway hyperreactivity and inflammation. J Allergy Clin Immunol. Sep. 2002;110(3):460-8.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1→3)-beta-D-glucans in mice. Biol Pharm Bull. Jan. 1995;18(1):126-33.
Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk et al., Evidence for T Cell-dependent Immunity to Bacteroides fragilis in an Intraabdominal Abscess Model; J. Clin Invest. 69:9-16 (1982).
Ostman et al., Impaired regulatory T cell function in germ-free mice. Eur J Immunol. Sep. 2006;36(9):2336-46.
Ozenci et al., Multiple sclerosis: levels of interleukin-10-secreting blood mononuclear cells are low in untreated patients but augmented during interferon-beta-1b treatment. Scand J Immunol. May 1999;49(5):554-61.
Palmer et al., Lineage-specific effects of 1,25-dihydroxyvitamin D(3) on the development of effector CD4 T cells. J Biol Chem. Jan. 14, 2011;286(2):997-1004. doi: 10.1074/jbc.M110.163790. Epub Nov. 3, 2010.
Palmer et al., Development of the human infant intestinal microbiota. PLoS Biol. Jul. 2007;5(7):e177. Epub Jun. 26, 2007.

(56) References Cited

OTHER PUBLICATIONS

Pamer, Immune responses to commensal and environmental microbes. Nat Immunol. Nov. 2007;8(11):1173-8.
Pantosti et al., Bacteroides fragilis strains express multiple capsular polysaccharides. J Clin Microbiol. Jul. 1993;31(7):1850-5.
Pantosti et al., Immunochemical characterization of two surface polysaccharides of Bacteroides fragilis. Infect Immun. Jun. 1991;59(6):2075-82.
Paoletti et al., Neonatal Mouse Protection against Infection with Multiple Group B *Streptococcal* (GBS) Serotypes by Maternal Immunization with a Tetravalent GBS Polysaccharide-Tetanus Toxoid Conjugate Vaccine, Infection and Immunity, 62:3236-3243, 1994.
Paoletti et al., Effects of chain length on the immunogenicity in rabbits of group B *Streptococcus* type III oligosaccharide-tetanus toxoid conjugates. J Clin Invest. Jan. 1992;89(1):203-9.
Park et al., Interleukin-2 and soluble interleukin-2 receptor in bronchoalveolar lavage fluid from patients with bronchial asthma. Chest. Aug. 1994;106(2):400-6.
Pato et al., Purification of capsular polysaccharide from Neisseria meningitidis serogroup C by liquid chromatography. J Chromatogr B Analyt Technol Biomed Life Sci. Mar. 7, 2006;832(2):262-7. Epub Feb. 15, 2006.
Patrick et al., Separation of capsulate and non-capsulate Bacteroides fragilis on a discontinuous density gradient. J Med Microbiol. May 1983;16(2):239-41.
Patrick et al., A comparison of the haemagglutinating and enzymic activities of Bacteroides fragilis whole cells and outer membrane vesicles. Microb Pathog. Apr. 1996;20(4):191-202.
Patrick et al., Mutational analysis of genes implicated in LPS and capsular polysaccharide biosynthesis in the opportunistic pathogen Bacteroides fragilis. Microbiology. Apr. 2009;155(Pt 4):1039-49. doi: 10.1099/mic.0.025361-0.
Pavliak et al., Structural elucidation of the capsular polysaccharide of Bacteroides fragilis strain 23745M1. Carbohydr Res. Oct. 2, 1995;275(2):333-41.
Pedersen et al., 1,25-dihydroxyvitamin D3 reverses experimental autoimmune encephalomyelitis by inhibiting chemokine synthesis and monocyte trafficking. J Neurosci Res. Aug. 15, 2007;85(11):2480-90.
Perumal et al., Protective effect of interleukin-2 on experimental intra-abdominal abscess development due to Bacteriodes Fragilis. Clinical Research. 1990;38(2):550A.
Pierrot-Deseilligny et al., Is hypovitaminosis D one of the environmental risk factors for multiple sclerosis? Brain. Jul. 2010;133(Pt 7):1869-88. doi: 10.1093/brain/awq147.
Poonawalla et al.; Urticaria a Review; Am J Clin Dermotol 2009; 10(1):9-21.
Popivanova et al., Blocking TNF-alpha in mice reduces colorectal carcinogenesis associated with chronic colitis. J Clin Invest. Feb. 2008;118(2):560-70. doi: 10.1172/JCI32453.
Popovic et al., Inhibition of autoimmune encephalomyelitis by a tetracycline. Ann Neurol. Feb. 2002;51(2):215-23.
Power et al., The human microbiome in multiple sclerosis: pathogenic or protective constituents? Can J Neurol Sci. Sep. 2010;37 Suppl 2:S24-33.
Powrie et al., Immunology. Regulating the regulators. Science. Feb. 14, 2003;299(5609):1030-1.
Poxton et al., Mucosa-associated bacterial flora of the human colon. J Med Microbiol. Jan. 1997;46(1):85-91.
Prieto et al., A New Ganglioside in Human Meconium Detected by Antiserum against the Human Milk Sialyloligosaccharide, LS-Tetrasacharide b.sup.1, Archives of Biochemistry and Biophysics, 241:281-289, 1985.
Rabe et al., Pharmacological treatment of asthma today. Eur Respir J Suppl. 2001;34:34s-40s.
Raetz et al., Lipopolysaccharide endotoxins. Annu Rev Biochem. 2002;71:635-700. Epub Nov. 9, 2001.
Raghuwanshi et al., Vitamin D and multiple sclerosis. J Cell Biochem. Oct. 1, 2008;105(2):338-43. doi: 10.1002/jcb.21858.
Rakoff-Nahoum et al., Recognition of commensal microflora by toll-like receptors is required for intestinal homeostasis. Cell. Jul. 23, 2004;118(2):229-41.
Raman et al., Vitamin D and gastrointestinal diseases: inflammatory bowel disease and colorectal cancer. Therap Adv Gastroenterol. Jan. 2011;4(1):49-62. doi: 10.1177/1756283X10377820.
Ranua et al., Serum IgA, IgG, and IgM concentrations in patients with epilepsy and matched controls: a cohort-based cross-sectional study. Epilepsy Behav. Mar. 2005;6(2):191-5.
Reed et al., A simple method of estimating fifty percent endpoints. Am J Hyg. 1938;27:493-497.
Rescigno et al., Dendritic cells express tight junction proteins and penetrate gut epithelial monolayers to sample bacteria. Nat Immunol. Apr. 2001;2(4):361-7.
Riesenfeld et al., Biosynthesis of heparin. Assay and properties of the microsomal N-acetyl-D-glucosaminyl N-deacetylase.J Biol Chem. Feb. 10, 1980;255(3):922-8.
Roncarolo et al., Type I T regulatory cells. Immunol Rev. Aug. 2001;182:68-79. Review.
Rose et al., Multifunctional role of dextran sulfate sodium for in vivo modeling of intestinal diseases. BMC Immunol. Aug. 1, 2012;13:41. doi: 10.1186/1471-2172-13-41.
Round et al., Coordination of tolerogenic immune responses by the commensal microbiota. J Autoimmun. May 2010;34(3):J220-5. doi: 10.1016/j.jaut.2009.11.007. Epub Dec. 6, 2009.
Round et al., The Toll-like receptor 2 pathway establishes colonization by a commensal of the human microbiota. Science. May 20, 2011;332(6032):974-7. doi: 10.1126/science.1206095. Epub Apr. 21, 2011.
Round et al., The gut microbiota shapes intestinal immune responses during health and disease. Nat Rev Immunol. May 2009;9(5):313-23. doi: 10.1038/nri2515.
Round et al., Inducible Foxp3+ regulatory T-cell development by a commensal bacterium of the intestinal microbiota. Proc Natl Acad Sci U S A. Jul. 6, 2010;107(27):12204-9. doi: 10.1073/pnas.0909122107. Epub Jun. 21, 2010.
Rubtsov et al., Regulatory T cell-derived interleukin-10 limits inflammation at environmental interfaces. Immunity. Apr. 2008;28(4):546-58. doi: 10.1016/j.immuni.2008.02.017.
Runia et al., Lower serum vitamin D levels are associated with a higher relapse risk in multiple sclerosis. Neurology. Jul. 17, 2012;79(3):261-6. doi: 10.1212/WNL.0b013e31825fdec7. Epub Jun. 13, 2012.
Ruiz-Perez et al., Modulation of surgical fibrosis by microbial zwitterionic polysaccharides. Proc Natl Acad Sci U S A. Nov. 15, 2005;102(46):16753-8. Epub Nov. 7, 2005.
Russell, Lethal effects of heat on bacterial physiology and structure. Sci Prog. 2003;86(Pt 1-2):115-37.
Rutgeerts et al., Infliximab for induction and maintenance therapy for ulcerative colitis. N Engl J Med. Dec. 8, 2005;353(23):2462-76.
Rypens et al., Percutaneous drainage of abdominal abscesses in pediatric Crohn's disease. AJR Am J Roentgenol. Feb. 2007;188(2):579-85.
Sakaguchi et al., Regulatory T cells and immune tolerance. Cell. May 30, 2008;133(5):775-87. doi: 10.1016/j.cell.2008.05.009.
Sakaguchi et al., Foxp3+ CD25+ CD4+ natural regulatory T cells in dominant self-tolerance and autoimmune disease. Immunol Rev. Aug. 2006;212:8-27.
Salyers et al., Conjugative transposons: an unusual and diverse set of integrated gene transfer elements. Microbiol Rev. Dec. 1995;59(4):579-90. Review.
Sartor, Mechanisms of disease: pathogenesis of Crohn's disease and ulcerative colitis. Nat Clin Pract Gastroenterol Hepatol. Jul. 2006;3(7):390-407.
Sawada et al., Leukocytapheresis in ulcerative colitis: results of a multicenter double-blind prospective case-control study with sham apheresis as placebo treatment. Am J Gastroenterol. Jun. 2005;100(6):1362-9.
Scheiffele et al., Induction of TNBS colitis in mice. Curr Protoc Immunol. Aug. 2002;Chapter 15:Unit 15.19. doi: 10.1002/0471142735.im1519s49.

(56) References Cited

OTHER PUBLICATIONS

Scheinin et al., Validation of the interleukin-10 knockout mouse model of colitis: antitumour necrosis factor-antibodies suppress the progression of colitis. Clin Exp Immunol. Jul. 2003;133(1):38-43.
Schembri Ma et al. Orientation-dependent enhancement by H—NS of the activity of the type 1 fimbrial phase switch promoter in *Escherichia coli*. (1998) Mol Gen Genet 259:336-44.
Schlegel et al., A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo. Proc Natl Acad Sci U S A. May 14, 1996;93(10):5061-6. Erratum in: Proc Natl Acad Sci U S A Aug. 6, 1996;93(16):8796.
Schneider et al., De novo design of molecular architectures by evolutionary assembly of drug-derived building blocks. J Comput Aided Mol Des. Jul. 2000;14(5):487-94.
Segal et al., Severe insulin resistance secondary to insulin antibodies: successful treatment with the immunosuppressant MMF. Pediatr Diabetes. Jun. 2008;9(3 Pt 1):250-4.
Sellin et al., Conformational analysis of a toxic peptide from Trimeresurus wagleri which blocks the nicotinic acetylcholine receptor. Biophys J. Jan. 1996;70(1):3-13.
Sellon et al., Resident enteric bacteria are necessary for development of spontaneous colitis and immune system activation in interleukin-10-deficient mice. Infect Immun. Nov. 1998;66(11):5224-31.
Shaklee et al., Hydrazinolysis of heparin and other glycosaminoglycans. Biochem. J. (1984); 217: 187-197.
Shapiro et al., Cellular control of abscess formation: role of T cells in the regulation of abscesses formed in response to Bacteroides fragilis. J Immunol. Jul. 1, 1986;137(1):341-6.
Shapiro et al., Cellular immunity to Bacteroides fragilis capsular polysaccharide. J Exp Med. Apr. 1, 1982;155(4):1188-97.
Sharpe et al., The B7-CD28 superfamily. Nat Rev Immunol. Feb. 2002;2(2):116-26. Review.
Shevach, CD4+ CD25+ suppressor T cells: more questions than answers. Nat Rev Immunol. Jun. 2002;2(6):389-400. Review.
Sigmundsdottir et al., DCs metabolize sunlight-induced vitamin D3 to 'program' T cell attraction to the epidermal chemokine CCL27. Nat Immunol. Mar. 2007;8(3):285-93. Epub Jan. 28, 2007.
Silvestro et al., Effects of subinhibitory concentrations of clindamycin on the morphological, biochemical and genetic characteristics of Bacteroides fragilis. FEMS Microbiol Lett. Apr. 2006;257(2):189-94.
Simmons et al., Synthesis and membrane permeability of PNA-peptide conjugates. Bioorg Med Chem Lett. 1997;7(23):3001-6.
Slack et al., Innate and adaptive immunity cooperate flexibly to maintain host-microbiota mutualism. Science. Jul. 31, 2009;325(5940):617-20. doi: 10.1126/science.1172747.
Smith et al. Functional analysis of the FimE integrase of *Escherichia coli* K-12: isolation of mutant derivatives with altered DNA inversion preferences. (1999) Mol Microbiol 34:965-79.
Smith et al., Use of axenic animals in studying the adaptation of mammals to their commensal intestinal microbiota. Semin Immunol. Apr. 2007;19(2):59-69. Epub Nov. 21, 2006.
Smits et al., Selective probiotic bacteria induce IL-10-producing regulatory T cells in vitro by modulating dendritic cell function through dendritic cell-specific intercellular adhesion molecule 3-grabbing nonintegrin. J Allergy Clin Immunol. Jun. 2005;115(6):1260-7.
Solomon et al., Multiple sclerosis and vitamin D: a review and recommendations. Curr Neurol Neurosci Rep. Sep. 2010;10(5):389-96. doi: 10.1007/s11910-010-0131-5.
Spach et al., Vitamin D3 confers protection from autoimmune encephalomyelitis only in female mice. J Immunol. Sep. 15, 2005;175(6):4119-26.
Spach et al., Gene expression analysis suggests that 1,25-dihydroxyvitamin D3 reverses experimental autoimmune encephalomyelitis by stimulating inflammatory cell apoptosis. Physiol Genomics. Jul. 8, 2004;18(2):141-51.

Sprinz et al., The response of the germfree guinea pig to oral bacterial challenge with *Escherichia coli* and Shigella flexneri. Am J Pathol. Dec. 1961;39:681-95.
Stein et al., Thymus-independent and thymus-dependent responses to polysaccharide antigens. J Infect Dis. Jun. 1992;165 Suppl 1:S49-52. Review.
Stewart et al., Interferon-β and serum 25-hydroxyvitamin D interact to modulate relapse risk in MS. Neurology. Jul. 17, 2012;79(3):254-60. doi: 10.1212/WNL.0b013e31825fded9. Epub Jun. 13, 2012.
Stingele et al., Zwitterionic polysaccharides stimulate T cells with no preferential V beta usage and promote anergy, resulting in protection against experimental abscess formation. J Immunol. Feb. 1, 2004;172(3):1483-90.
Stockinger et al., Differentiation and function of Th17 T cells. Curr Opin Immunol. Jun. 2007;19(3):281-6. Epub Apr. 12, 2007.
Strachan, Hay fever, hygiene, and household size. BMJ. Nov. 18, 1989;299(6710):1259-60.
Strauch et al., Influence of intestinal bacteria on induction of regulatory T cells: lessons from a transfer model of colitis. Gut. Nov. 2005;54(11):1546-52. Epub Jun. 29, 2005.
Strober, The multifaceted influence of the mucosal microflora on mucosal dendritic cell responses. Immunity. Sep. 18, 2009;31(3):377-88. doi: 10.1016/j.immuni.2009.09.001.
Stromnes et al., Active induction of experimental allergic encephalomyelitis. Nat Protoc. 2006;1(4):1810-9.
Stromnes et al., Passive induction of experimental allergic encephalomyelitis. Nat Protoc. 2006;1(4):1952-60.
Stumhofer et al., Interleukins 27 and 6 induce STAT3-mediated T cell production of interleukin 10. Nat Immunol. Dec. 2007;8(12):1363-71. Epub Nov. 11, 2007.
Suri-Payer et al., CD4+CD25+ T cells inhibit both the induction and effector function of autoreactive T cells and represent a unique lineage of immunoregulatory cells. J Immunol. Feb. 1, 1998;160(3):1212-8.
Sutmuller et al., Toll-like receptor 2 controls expansion and function of regulatory T cells. J Clin Invest. Feb. 2006;116(2):485-94. Epub Jan. 19, 2006.
Szu et al., Relation between structure and immunologic properties of the Vi capsular polysaccharide. Infect Immun. Dec. 1991;59(12):4555-61.
Tanaka et al., Human monocyte-derived dendritic cells induce naive T cell differentiation into T helper cell type 2 (Th2) or Th1/Th2 effectors. Role of stimulator/responder ratio. J Exp Med. Aug. 7, 2000;192(3):405-12.
Tang et al., Th type 1-stimulating activity of lung macrophages inhibits Th2-mediated allergic airway inflammation by an IFN-gamma-dependent mechanism. J Immunol. Feb. 1, 2001;166(3):1471-81.
Taurog et al., The germfree state prevents development of gut and joint inflammatory disease in HLA-B27 transgenic rats. J Exp Med. Dec. 1, 1994;180(6):2359-64.
Taylor et al., Stoichiometric depolymerization of polyuronides and glycosaminoglycuronans to monosaccharides following reduction of their carbodiimide-activated carboxyl groups. Biochemistry. Apr. 11, 1972;11(8):1383-8.
Teitelbaum et al., Immunomodulation of experimental autoimmune encephalomyelitis by oral administration of copolymer 1. Proc Natl Acad Sci U S A. Mar. 30, 1999;96(7):3842-7.
Teitelbaum et al., Specific inhibition of the T-cell response to myelin basic protein by the synthetic copolymer Cop 1. Proc Natl Acad Sci U S A. Dec. 1988;85(24):9724-8.
Teitelbaum et al., Synthetic copolymer 1 inhibits human T-cell lines specific for myelin basic protein. Proc Natl Acad Sci U S A. Jan. 1, 1992;89(1):137-41.
Teitelbaum et al., Unprimed spleen cell populations recognize macrophage-bound antigen with opposite net electric charge. Proc Natl Acad Sci U S A. Apr. 1977;74(4):1693-6.
Thomas et al., Randomized controlled trial of short bursts of a potent topical corticosteroid versus prolonged use of a mild preparation for children with mild or moderate atopic eczema. BMJ. 2002;324:1-7.
Tong et al., Mouse models of colorectal cancer. Chin J Cancer. Jul. 2011;30(7):450-62. doi: 10.5732/cjc.011.10041.

(56) References Cited

OTHER PUBLICATIONS

Tournoy et al., Endogenous interleukin-10 suppresses allergen-induced airway inflammation and nonspecific airway responsiveness. Clin Exp Allergy. Jun. 2000;30(6):775-83.
Toussirot et al., Bacterial extract (OM-89) specific and non specific immunomodulation in rheumatoid arthritis patients. Autoimmunity. Jun. 2006;39(4):299-306.
Triantafillidis et al., Colorectal cancer and inflammatory bowel disease: epidemiology, risk factors, mechanisms of carcinogenesis and prevention strategies. Anticancer Res. Jul. 2009;29(7):2727-37.
Troy et al., Beneficial effects of Bacteroides fragilis polysaccharides on the immune system. Front Biosci (Landmark Ed). Jan. 1, 2010;15:25-34.
Troy et al., Orientations of the Bacteroides fragilis capsular polysaccharide biosynthesis locus promoters during symbiosis and infection. J Bacteriol. Nov. 2010;192(21):5832-6. doi: 10.1128/JB.00555-10. Epub Aug. 20, 2010.
Turnbaugh et al., The human microbiome project. Nature. Oct. 18, 2007;449(7164):804-10.
Turnbaugh et al., An obesity-associated gut microbiome with increased capacity for energy harvest. Nature. Dec. 21, 2006;444(7122):1027-31.
Tzeng et al., Translocation and surface expression of lipidated serogroup B capsular. Polysaccharide in Neisseria meningitidis. Infect Immun. Mar. 2005;73(3):1491-505.
Tzianabos, Polysaccharide Immunomodulators as Therapeutic Agents: Structural Aspects and Biologic Function, Clin. Microbiol. Rev. 13(4):523-533 (2000).
Tzianabos, et al., Polysaccharide-mediated protection against abscess formation in experimental intra-abdominal sepsis. J Clin. Invest. (1995) 96:2727-31.
Tzianabos, et al., Structural characteristics of polysaccharides that induce protection against intra-abdominal abscess formation. Infect Immun (1994) 62:4881-86.
Tzianabos et al., Bacterial structure and functional relation to abscess formation. Infect Agents Dis. Oct. 1994;3(5):256-65. Review.
Tzianabos et al., Characteristics of bacterial polysaccharides that activate T cells. The International Carbohydrate Symposium XVII. Jul. 21, 1994.
Tzianabos et al., Effect of surgical adhesion reduction devices on the propagation of experimental intra-abdominal infection. Arch Surg. Nov. 1999;134(11):1254-9.
Tzianabos et al., IL-2 mediates protection against abscess formation in an experimental model of sepsis. J Immunol. Jul. 15, 1999;163(2):893-7.
Tzianabos et al., Protection against experimental intraabdominal sepsis by two polysaccharide immunomodulators. J Infect Dis. Jul. 1998;178(1):200-6.
Tzianabos et al., Structural basis for polysaccharide-mediated protection against intraabdominal abscess formation. 94$^{th}$ ASM General Meeting. May 23-27, 1994. Las Vegas, Nevada. Abstract B-206:65.
Tzianabos, et al., Structural rationale for the modulation of abscess formation by Staphylococcus aureus capsular polysaccharides. Proc Natl Acad Sci U S A. Jul. 31, 2001;98(16):9365-70. Epub Jul. 24, 2001.
Tzianabos et al., Structure and function of Bacteroides fragilis capsular polysaccharides: relationship to induction and prevention of abscesses. Clin Infect Dis. Jun. 1995;20 Suppl 2:S132-40. Review.
Tzianabos et al., Structure-function relationships for polysaccharide-induced intra-abdominal abscesses. Infect Immun. Aug. 1994;62(8):3590-3.
Tzianabos et al., T Cell Activation by Zwitterionic polysaccharides and peptide mimetics prevents antrabdominal abscess formation. Abstracts of the 99$^{th}$ General Meeting of the American Society for Microbiology. Chicago, US: May 30-Jun. 3, 1999. Jun. 28, 1999;99:37-38.
Tzianabos et al., The capsular polysaccharide of Bacteroides fragilis comprises two ionically linked polysaccharides. J Biol Chem. Sep. 5, 1992;267(25):18230-5.
Tzianabos et al., T cells activated by zwitterionic molecules prevent abscesses induced by pathogenic bacteria. J Biol Chem. Mar. 10, 2000;275(10):6733-40.
Tzianabos et al., Structural features of polysaccharides that induce intra-abdominal abscesses. Science. Oct. 15, 1993;262(5132):416-9.
Uronis et al., Modulation of the intestinal microbiota alters colitis-associated colorectal cancer susceptibility. PLoS One. Jun. 24, 2009;4(6):e6026. doi: 10.1371/journal.pone.0006026.
Van Maren, Toll-like receptor signalling on Tregs: to suppress or not to suppress? Immunology. Aug. 2008;124(4):445-52. doi: 10.1111/j.1365-2567.2008.02871.x. Epub Jun. 28, 2008.
Van Scott et al., IL-10 reduces Th2 cytokine production and eosinophilia but augments airway reactivity in allergic mice. Am J Physiol Lung Cell Mol Physiol. Apr. 2000;278(4):L667-74.
Vann et al., The structure of the capsular polysaccharide (K5 antigen) of urinary-tract-infective Escherichia coli 010:K5:H4. A polymer similar to desulfo-heparin. Eur J Biochem. May 15, 1981;116(2):359-64.
Veldhoen et al., TGFbeta in the context of an inflammatory cytokine milieu supports de novo differentiation of IL-17-producing T cells. Immunity. Feb. 2006;24(2):179-89.
Velez et al., Type I Streptococcus pneumoniae carbohydrate utilizes a nitric oxide and MGC II-dependent pathway for antigen presentation. Immunol. 2008;127:73-82.
Verdu et al., Oral administration of antigens from intestinal flora anaerobic bacteria reduces the severity of experimental acute colitis in BALB/c mice. Clin Exp Immunol. Apr. 2000;120(1):46-50.
Videla et al., Role of intestinal microflora in chronic inflammation and ulceration of the rat colon. Gut. Aug. 1994;35(8):1090-7.
Vignali et al., How regulatory T cells work. Nat Rev Immunol. Jul. 2008;8(7):523-32. doi: 10.1038/nri2343.
Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.
Viret et al., Molecular cloning and characterization of the genetic determinants that express the complete Shigella serotype D (Shigella sonnei) lipopolysaccharide in heterologous live attenuated vaccine strains. Mol Microbiol. Jan. 1993;7(2):239-52.
Wagner et al., Use of reporter cells to study endogenous retinoid sources in embryonic tissues. Methods Enzymol. 1997;282:98-107.
Wang et al., A bacterial carbohydrate links innate and adaptive responses through Toll-like receptor 2. J Exp Med. Dec. 25, 2006;203(13):2853-63. Epub Dec. 18, 2006.
Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.
Wang et al., Ozonolysis for selectively depolymerizing polysaccharides containing β-d-aldosidic linkages. Proc Natl Acad Sci U S A. Jun. 9, 1998; 95(12): 6584-6589.
Wang et al., Structural basis of the abscess-modulating polysaccharide A2 from Bacteroides fragilis. Proc Natl Acad Sci U S A. Dec. 5, 2000;97(25):13478-83.
Wang et al., Structure characterization of an abscessogenic capsular polysaccharide from Bacteriodes fragilis by NMR spectroscopy. XIX International Conference of NMR in Biological Systems. Florence, Italy. Aug. 20-25, 2000. Abstract.
Ward et al., The nucleotide sequence of the tnpA gene of Tn21, Nucleic Acids Research, vol. 15(4), 1987, 1799-1806.
Wehr et al., Anti-low-density lipoprotein antibodies in alcoholics without and with liver disease and in social drinkers. Alcohol Alcohol. Jan.-Feb. 1997;32(1):43-9.
Weinacht et al. Phase variation of the capsular polysaccharides of Bacteroides fragilis is dictated by site-specific recombinases. 2002 General Meeting of the American Society for Microbiology, May 19-23, 2002. Abstract.
Weintraub et al., Structural characterization of the lipid A component of Bacteroides fragilis strain NCTC 9343 lipopolysaccharide. Eur J Biochem. Aug. 1, 1989;183(2):425-31.

(56) References Cited

OTHER PUBLICATIONS

Wen et al., Innate immunity and intestinal microbiota in the development of Type 1 diabetes. Nature. Oct. 23, 2008;455(7216):1109-13. doi: 10.1038/nature07336. Epub Sep. 21, 2008.
Wessels et al., Structural Determination and Immunochemical Characterization of the Type V Group B *Streptococcus* Capsular Polysaccharide, The Journal of Biological Chemistry, 266:6714-6719, 1991.
Wessels et al., Structure and immunochemistry of an oligosaccharide repeating unit of the capsular polysaccharide of type III group B *Streptococcus*. A revised structure for the type III group B *streptococcal* polysaccharide antigen. J Biol Chem. Jun. 15, 1987;262(17):8262-7.
Wexler, Bacteroides: the good, the bad, and the nitty-gritty. Clin Microbiol Rev. Oct. 2007;20(4):593-621.
Whitfield, Biosynthesis and assembly of capsular polysaccharides in *Escherichia coli*. Annu Rev Biochem. 2006;75:39-68.
Wiegandt et al., Carbohydrate Components of Extraneuronal Gangliosides from Bovine and Human Spleen, and Bovine Kidney, European Journal of Biochemistry, 15:287-292, 1970.
Willer et al., Twin concordance and sibling recurrence rates in multiple sclerosis. Proc Natl Acad Sci U S A. Oct. 28, 2003;100(22):12877-82. Epub Oct. 20, 2003.
Wirtz et al., Mouse models of inflammatory bowel disease. Adv Drug Deliv Rev. Sep. 30, 2007;59(11):1073-83. Epub Aug. 16, 2007.
Woessner et al., Long-term antibiotic treatment with roxithromycin in patients with multiple sclerosis. Infection. Dec. 2006;34(6):342-4.
Wong et al., Activation of peripheral Th17 lymphocytes in patients with asthma. Immunol Invest. 2009;38(7):652-64.
Woodruff et al., Sudden-onset severe acute asthma: clinical features and response to therapy. Acad Emerg Med. Jul. 1998;5(7):695-701.
Wu et al., Gut-residing segmented filamentous bacteria drive autoimmune arthritis via T helper 17 cells. Immunity. Jun. 25, 2010;32(6):815-27. doi: 10.1016/j.immuni.2010.06.001.
Wujek et al., A carbohydrate polymer that effectively prevents epidural fibrosis at laminectomy sites in the rat. Exp Neurol. Nov. 1991;114(2):237-45.
Xavier et al., Commensal flora: wolf in sheep's clothing. Gastroenterology. Apr. 2005;128(4):1122-6.
Xavier et al., Unravelling the pathogenesis of inflammatory bowel disease. Nature. Jul. 26, 2007;448(7152):427-34.
Xie et al., Cancer in inflammatory bowel disease. World J Gastroenterol. Jan. 21, 2008;14(3):378-89.
Xu J et al., A genomic view of the human-Bacteroides thetaiotaomicron symbiosis. Science. Mar. 28, 2003;299(5615):2074-6.
Yamazaki et al., CCR6 regulates the migration of inflammatory and regulatory T cells. J Immunol. Dec. 15, 2008;181(12):8391-401.
Yamazaki et al., Dendritic cells are specialized accessory cells along with TGF—for the differentiation of Foxp3+ CD4+ regulatory T cells from peripheral Foxp3 precursors. Blood. Dec. 15, 2007;110(13):4293-302. Epub Aug. 15, 2007.
Yokoyama et al., Adhesion behavior of rat lymphocytes to poly(ether)-poly(amino acid) block and graft copolymers. J Biomed Mater Res. Sep. 1986;20(7):867-78.
Yoshii, Cytotoxic effects of acrylates and methacrylates: relationships of monomer structures and cytotoxicity. J Biomed Mater Res. Dec. 15, 1997;37(4):517-24.

Young et al., In vitro and in vivo characterization of Helicobacter hepaticus cytolethal distending toxin mutants. Infect Immun. May 2004;72(5):2521-7.
Zabad et al., The clinical response to minocycline in multiple sclerosis is accompanied by beneficial immune changes: a pilot study. Mult Scler. May 2007;13(4):517-26. Epub Feb. 9, 2007.
Zaleznik et al., A soluble suppressor T cell factor protects against experimental intraabdominal abscesses. J Clin Invest. Mar. 1985;75(3):1023-7.
Zaph et al., Commensal-dependent expression of IL-25 regulates the IL-23-IL-17 axis in the intestine. J Exp Med. Sep. 29, 2008;205(10):2191-8. doi: 10.1084/jem.20080720. Epub Sep. 1, 2008.
Zehnder et al., Extrarenal expression of 25-hydroxyvitamin d(3)-1 alpha-hydroxylase. J Clin Endocrinol Metab. Feb. 2001;86(2):888-94.
Zehnder et al., Expression of 25-hydroxyvitamin D3-1alpha-hydroxylase in the human kidney. J Am Soc Nephrol. Dec. 1999;10(12):2465-73.
Zhang et al., Degradation of Wood Polysaccharide Model Compounds During Ozone Treatment. Journal of Pulp and Paper Science. Jan. 1997;23(1):J23-J27.
Zhang et al., IL-10 is involved in the suppression of experimental autoimmune encephalomyelitis by CD25+CD4+ regulatory T cells. Int Immunol. Feb. 2004;16(2):249-56.
Zhao H et al. In vivo phase variation of MR/P fimbrial gene expression in Proteus mirabilis infecting the urinary tract. (1997) Mol Microbiol 23:1009-19.
Zhou et al., TGF-beta-induced Foxp3 inhibits T(H)17 cell differentiation by antagonizing RORgammat function. Nature. May 9, 2008;453(7192):236-40. doi: 10.1038/nature06878. Epub Mar. 26, 2008.
Zhu et al., Oral administration of type-II collagen peptide 250-270 suppresses specific cellular and humoral immune response in collagen-induced arthritis. Clin Immunol. Jan. 2007;122(1):75-84. Epub Oct. 11, 2006.
U.S. Appl. No. 10/432,406, filed Nov. 20, 2003, Granted, U.S. Pat. No. 7,629,330.
U.S. Appl. No. 12/470,985, filed May 22, 2009, Granted, U.S. Pat. No. 8,008,276.
U.S. Appl. No. 10/814,620, filed Mar. 31, 2004, Abandoned, 2004-0219160.
U.S. Appl. No. 12/754,948, filed Apr. 6, 2010, Abandoned, 2011-0059125.
U.S. Appl. No. 13/316,744, filed Dec. 12, 2011, Abandoned, 2012-0315264.
U.S. Appl. No. 14/043,876, filed Oct. 2, 2013, Granted, U.S. Pat. No. 9,265,790.
U.S. Appl. No. 12/223,563, filed Apr. 3, 2009, Granted, U.S. Pat. No. 8,206,726.
U.S. Appl. No. 13/493,512, filed Jun. 11, 2012, Abandoned, 2012-0309955.
U.S. Appl. No. 14/131,812, filed Apr. 7, 2014, Granted, 2014-0243285.
U.S. Appl. No. 16/317,794, filed Jan. 14, 2019, Published, 2019-0290680.
EP16837913.9, Jun. 19, 2019, Extended European Search Report.
PCT/US2016/047787, Mar. 1, 2018, International Preliminary Report on Patentability.
PCT/US2016/047787, Jan. 6, 2017, International Search Report and Written Opinion.

\* cited by examiner

Molecular species of PSA glycolipids and proposed acyl chain composition

| # of acyl group | M/Z of [M+Na+]+ | Proposed acyl chain composition | | | | |
|---|---|---|---|---|---|---|
| Penta | 1646 | c16:0-OH | c17:0-OH | c17:0-OH | c17:0-OH | c15:0 |
| | 1632 | c16:0-OH | c16:0-OH | c17:0-OH | c17:0-OH | c15:0 |
| | 1618 | c16:0-OH | c16:0-OH | c16:0-OH | c17:0-OH | c15:0 |
| | 1604 | c16:0-OH | c16:0-OH | c16:0-OH | c16:0-OH | c15:0 |
| | 1590 | c16:0-OH | c16:0-OH | c16:0-OH | c16:0-OH | c14:0 |
| Tetra | 1392 | | c17:0-OH | c17:0-OH | c17:0-OH | c15:0 |
| | 1378 | | c16:0-OH | c17:0-OH | c17:0-OH | c15:0 |
| | 1364 | | c16:0-OH | c16:0-OH | c17:0-OH | c15:0 |
| | 1350 | | c16:0-OH | c16:0-OH | c16:0-OH | c15:0 |
| | 1336 | | c16:0-OH | c16:0-OH | c16:0-OH | c14:0 |
| Tri | 1123 | | | c17:0-OH | c17:0-OH | c15:0 |
| | 1109 | | | c16:0-OH | c17:0-OH | c15:0 |
| | 1095 | | | c16:0-OH | c16:0-OH | c15:0 |
| | 1081 | | | c16:0-OH | c16:0-OH | c14:0 |
| Di | 899 | | | | c17:0-OH | c17:0-OH |
| | 885 | | | | c16:0-OH | c17:0-OH |

FIG. 5

Representative structures of PSA lipid anchors, a tetraacylated (left) and pentaacylated (right) diGluNs.

FIG. 14

| pentaacylated | | | | | | |
|---|---|---|---|---|---|---|
| | 5xOH | | 4xOH | | 3xOH | |
| total Acyl Carbon | exact mass | CPS | exact mass | CPS | exact mass | CPS |
| 74 | 1542.3 | ND | 1526.3 | 999290 | 1510.3 | 2187535 |
| 75 | 1556.3 | 786504 | 1540.3 | 1261489 | 1524.3 | 3431369 |
| 76 | 1570.3 | 2673445 | 1554.3 | 1220670 | 1538.3 | 1691385 |
| 77 | 1584.3 | 8338616 | 1568.3 | 5992380 | 1552.3 | 4055057 |
| 78 | 1598.3 | 13803256 | 1582.3 | 16539240 | 1566.3 | 10375662 |
| 79 | 1612.3 | 11357658 | 1596.3 | 25412060 | 1580.3 | 19631384 |
| 80 | 1626.3 | 2033195 | 1610.3 | 18401147 | 1594.3 | 12449433 |
| 81 | 1640.3 | ND | 1624.3 | 3358855 | 1608.3 | 2835742 |
| 82 | | | 1638.3 | nd | 1622.3 | 1517435 |
| 83 | | | | | 1636.3 | 1162429 |
| 84 | | | | | | |
| 85 | | | | | | |

| tetraacylated | | | | | | |
|---|---|---|---|---|---|---|
| | 4xOH | | 3xOH | | 2xOH | |
| total Acyl Carbon | exact mass | CPS | exact mass | CPS | exact mass | CPS |
| 60 | 1300.0 | ND | 1284.0 | ND | 1268.0 | ND |
| 61 | 1314.0 | 561145 | 1298.0 | ND | 1282.0 | ND |
| 62 | 1328.0 | 3001367 | 1312.0 | 979210 | 1296.0 | 177876 |
| 63 | 1342.0 | 7747490 | 1326.0 | 2814859 | 1310.0 | 2931125 |
| 64 | 1356.0 | 6193798 | 1340.0 | 2509823 | 1324.0 | 7130550 |
| 65 | 1370.0 | 462989 | 1354.0 | 353662 | 1338.0 | 6665907 |
| 66 | 1384.0 | ND | 1368.0 | ND | 1352.0 | 1447857 |
| 67 | 1398.0 | | 1382.0 | | 1366.0 | 2428419 |
| 68 | 1412.0 | | 1396.0 | | 1380.0 | 2469079 |
| 69 | | | | | 1394 | 335522 |

LIPIDATED PSA COMPOSITIONS AND METHODS

RELATED APPLICATIONS

This application is a national stage filing under 35 U.S.C. 371 of International Patent Application Serial No. PCT/US2016/047787, filed Aug. 19, 2016, which was published under PCT Article 21(2) in English and which claims the benefit under 35 U.S.C. § 119(e) of U.S. Provisional Application Ser. No. 62/207,360, filed Aug. 19, 2015, entitled "LIPIDATED PSA COMPOSITIONS AND METHODS", the entire contents of each of which are incorporated herein by reference.

FIELD OF THE INVENTION

The invention relates to lipidated capsular polysaccharide A (PSA), glycolipids, compositions, methods of synthesis, isolation and/or purification, and methods of use thereof.

BACKGROUND OF THE INVENTION

Polysaccharide A (PSA) of *Bacteroides fragilis* (*B. fragilis*) has been reported to be an immunomodulator with therapeutic and prophylactic activities. U.S. Pat. Nos. 5,679,654 and 5,700,787; Tzianabos A O et al. (2000) J Biol Chem 275:6733-40. PSA was recently discovered to possess a lipid moiety. The lipid moiety was hypothesized to anchor the polysaccharide in the *B. fragilis* outer membrane. It was also recently discovered that this "lipidated PSA" was significantly more potent than non-lipidated PSA (referred to herein as "PSA") forms provided in the prior art. The nature of the lipid moiety, however, has not been heretofore determined, and nor has the nature of its association with PSA.

SUMMARY OF THE INVENTION

The invention is based, in part, on the identification and characterization of the lipid moiety that is found conjugated to PSA using certain isolation methods. This disclosure provides the full structural identification and characterization of PSA conjugated to such lipid moiety (referred to herein as "lipidated PSA"). The invention is further premised, in part, on novel isolation methods and the recognition that such methods achieve greater yields of lipidated PSA than was heretofore possible. Significantly, the majority of prior art PSA isolation methods did not yield the lipidated form of the PSA at all. This is likely due, in part, to the use of a relatively stringent acid hydrolysis step late in the isolation process which released the lipid moiety from the lipidated PSA, thereby resulting in non-lipidated PSA.

The disclosure therefore provides, in some aspects, isolated lipidated PSA of a defined chemical structure, as well as compositions comprising isolated lipidated PSA. Such compositions may be further defined by the purity and/or concentration of isolated lipidated PSA contained therein. It has also been discovered that isolated lipidated PSA self assemble into a micelle form. Significantly, lipidated PSA does not adopt such a conformation in vivo, and accordingly such micelle form is non-naturally occurring. Even more significantly, it has been discovered that such micelles are very stable and thus difficult to disrupt. This has led to the finding that the combined use of certain disruptive agents (such as for example detergents and bile salts) and isolated lipidated PSA having a purity or concentration conducive to forming such stable micelles (as provided herein), renders the micelles less stable and makes more lipidated PSA accessible in vivo.

Also provided are synthetic forms of lipidated PSA and compositions thereof comprising one or more PSA polymers (each polymer comprising one or more of the repeating tetrasaccharide units of PSA), and one or more of the lipid or glycolipid components of lipidated PSA. The PSA and lipid or glycolipid components may be conjugated to each other directly or indirectly. Such conjugation may be covalent or non-covalent conjugation. As an example, the invention provides compositions comprising the PSA and lipid or glycolipid components in an unconjugated form together with a substrate such as a nanoparticle. These synthetic forms of lipidated polysaccharides may comprise PSA components (including tetrasaccharide units) and lipid or glycolipid components in ratios that are not found in nature.

The invention further provides methods of isolating lipidated PSA, methods of preparing the aforementioned synthetic forms of lipidated PSA, as well as in vitro and in vivo uses of the isolated and synthetic forms of lipidated PSA provided herein.

Thus, in one aspect, the invention provides an isolated lipidated polysaccharide A (PSA) comprising polysaccharide A (PSA) covalently conjugated to a glycolipid, wherein the glycolipid is di-acylated, tri-acylated, tetra-acylated or penta-acylated. In some embodiments, the glycolipid is tetra-acylated or penta-acylated.

In another aspect, the invention provides an isolated lipidated polysaccharide A (PSA) comprising polysaccharide A (PSA) covalently conjugated to a glycolipid comprising one or more acyl chains ranging in length from 14-17 carbons.

In various embodiments, the glycolipid comprises a disaccharide substituted with the one or more acyl chains. In various embodiments, the glycolipid comprises a diglucosamine.

In another aspect, the invention provides an isolated lipidated polysaccharide A (PSA) comprising polysaccharide A (PSA) covalently conjugated to one or more acyl chains ranging in length from 14-17 carbons.

In various embodiments, the one or more acyl chains range in length from 15-17 carbons.

In various embodiments, the isolated lipidated polysaccharide A (PSA) is substantially free of other components found in a *B. fragilis* capsule. In various embodiments, the isolated lipidated polysaccharide A (PSA) is substantially free of LPS. In various embodiments, the isolated lipidated polysaccharide A (PSA) is substantially free of unconjugated glycolipid. In various embodiments, the isolated lipidated polysaccharide A (PSA) is free of non-lipidated PSA. In various embodiments, the isolated lipidated polysaccharide A (PSA) is in purified form. In various embodiments, the lipidated polysaccharide A (PSA) is isolated from *B. fragilis* cells that overexpress PSA relative to polysaccharide B (PSB).

In various embodiments, the isolated lipidated polysaccharide A (PSA) is provided in a form is free of *B. fragilis* membrane, and thus is not provided as a *B. fragilis* cell or as a *B. fragilis* OMV. In various embodiments, the isolated lipidated polysaccharide A (PSA), including synthetic, non-naturally occurring versions of lipidated polysaccharide A (PSA), may be provided in a liposome or micelle form, and such liposome or micelle form may be non-naturally occurring (e.g., it may lack naturally occurring components and/or it may further comprise non-naturally occurring components such as non-naturally occurring lipids, surfactants, stabilizers, and the like).

In various embodiments, the isolated lipidated polysaccharide A (PSA) is in a micelle form.

In various embodiments, the isolated lipidated polysaccharide A (PSA) is in lyophilized form. Lyophilized forms of lipidated PSA are particularly suitable for long-term storage, ranging from days, weeks, months or even years.

In various embodiments, the isolated lipidated polysaccharide A (PSA) is suitable for administration to a human.

In another aspect, the invention provides any of the foregoing lipidated polysaccharide A (PSA), wherein the PSA component comprises less than 100, less than 90, less than 80, less than 70, less than 60, or less than 50 repeating tetrasaccharide units.

In another aspect, the invention provides any of the foregoing lipidated polysaccharide A (PSA), wherein the PSA component comprises 1-10 repeating tetrasaccharide units.

In another aspect, the invention provides a pharmaceutical composition comprising any of the foregoing lipidated polysaccharide A (PSA), and less than 0.5% (w/w) of free glycolipid.

In another aspect, the invention provides a pharmaceutical composition comprising any of the foregoing lipidated polysaccharide A (PSA), and a pharmaceutically acceptable carrier.

In various embodiments, the composition comprises less than 1% or less than 0.5% free glycolipid (w/w). In various embodiments, the composition further comprises a detergent or a bile salt. In various embodiments, the detergent of bile salt is present at a pharmaceutically acceptable level. In various embodiments, the detergent of bile salt is present at or less than 1%, 0.5% or 0.1%.

In various embodiments, the composition is in lyophilized form.

In various embodiments, the isolated lipidated polysaccharide A (PSA) is provided as a micelle or a liposome.

In another aspect, the invention provides a pharmaceutical composition comprising any of the foregoing lipidated polysaccharide A (PSA), and a detergent or a bile salt.

In another aspect, the invention provides a composition comprising any of the foregoing lipidated polysaccharide (PSA) in a micelle or a liposome.

In another aspect, the invention provides a composition comprising polysaccharide A (PSA) comprising 1 to 50 tetrasaccharide units, and a glycolipid, wherein PSA is covalently conjugated to the glycolipid.

In another aspect, the invention provides a composition comprising a polysaccharide comprising 1 to 50 tetrasaccharide units, each tetrasaccharide unit having a structure of Formula I, and a glycolipid comprising one or more acyl chains ranging in length from 14-17 carbons, wherein the polysaccharide is covalently conjugated to the glycolipid.

In various embodiments, the polysaccharide comprises 1-40 tetrasaccharide units or 1-20 tetrasaccharide units. In various embodiments, the polysaccharide comprises 1-10 tetrasaccharide units or 1-5 tetrasaccharide units.

In various embodiments, the composition is formulated for parenteral or enteral or oral administration to a subject. In various embodiments, the composition is formulated for lipophilic delivery, including for example in a liposome or in an oil-based delivery system. The various compositions provided herein may be formulated as a capsule or other discrete dosage form, including those intended for oral or enteral administration.

In another aspect, the invention provides an isolated glycolipid comprising a diglucosamine covalently conjugated to 2-5 acyl chains, each independently ranging in length from 14-17 carbons. The glycolipid may be any of the glycolipids provided herein, or a combination thereof.

In various embodiments, the diglucosamine is covalently conjugated to 2-5 or 2-4 acyl chains. In various embodiments, the diglucosamine is covalently conjugated to 4 or 5 acyl chains. In various embodiments, the acyl chains range in length from 15-17 carbons. Other embodiments relating to the glycolipids are recited below.

In another aspect, the invention provides a composition comprising polysaccharide A (PSA) and a glycolipid, in or on a substrate, wherein PSA is not covalently conjugated to the glycolipid.

In another aspect, the invention provides a composition comprising a polysaccharide comprising one or more tetrasaccharide units, each tetrasaccharide unit having a structure of Formula I, and a glycolipid comprising one or more acyl chains ranging in length from 14-17 carbons, wherein the polysaccharide and glycolipid are provided in unconjugated to each other, in or on a substrate.

In various embodiments, the substrate is a nanoparticle.

In various embodiments, PSA and the glycolipid are present in a molecular weight ratio of 10:1 to less than 1:1.

In another aspect, the invention provides a composition comprising polysaccharide A (PSA) and a glycolipid, covalently conjugated to each other via a non-ketosidic bond.

In another aspect, the invention provides a composition comprising a polysaccharide comprising one or more tetrasaccharide units, each tetrasaccharide unit having a structure of Formula I, and a glycolipid comprising one or more acyl chains ranging in length from 14-17 carbons, wherein the polysaccharide is covalently conjugated to the glycolipid via a non-ketosidic bond.

In various embodiments, the non-ketosidic bond is an ester, amide or ether bond.

In various embodiments, the glycolipid comprises a disaccharide. In various embodiments, disaccharide is diglucosamine.

In various embodiments, the glycolipid comprises 2-5 acyl chains. In various embodiments, the glycolipid comprises 4 or 5 acyl chains.

In various embodiments, at least one of the one or more acyl chains is unmodified. In various embodiments, at least one of the one or more acyl chains is modified. In various embodiments, at least one of the one or more acyl chains is unmodified and at least one of the one or more acyl chains is modified. In various embodiments, at least one of the one or more acyl chains is modified with a hydroxyl group.

In various embodiments, at least one of the one or more acyl chains is C16:0-OH. In various embodiments, at least one of the one or more acyl chains is C17:0-OH. In various embodiments, at least one of the one or more acyl chains is C14:0. In various embodiments, at least one of the one or more acyl chains is C15:0.

In various embodiments, at least one of the one or more acyl chains is N-substituted on a disaccharide. In various embodiments, at least one of the one or more acyl chains is O-substituted on a disaccharide. In various embodiments, at least one of the one or more acyl chains is N-substituted on a disaccharide and at least one of the one or more acyl chains is O-substituted on a disaccharide.

In various embodiments, the polysaccharide has a molecular weight of about 150 kiloDaltons. In various embodiments, the polysaccharide comprises 1-10 tetrasaccharide units.

In various embodiments, the glycolipid has a structure of Formula II. In various embodiments, the glycolipid has a structure of Formula III.

In various embodiments, polysaccharide and the glycolipid are present in or on a substrate. In various embodiments, the substrate is a film, a matrix or a particle. In various embodiments, the substrate is biodegradable. In various embodiments, the substrate is a nanoparticle.

In various embodiments, the composition further comprises a pharmaceutically acceptable carrier. In various embodiments, the composition is a pharmaceutical composition. In various embodiments, the composition is formulated for parenteral, enteral or oral administration. In various embodiments, the composition is effective in the treatment of an autoimmune disorder. In various embodiments, the composition is substantially free of other components found in a *B. fragilis* capsule and is suitable for administration to a human.

In another aspect, the invention provides a micelle consisting essentially of lipidated PSA. In various embodiments, the lipidated PSA is isolated lipidated PSA.

In another aspect, the invention provides a composition comprising a micelle consisting essentially of lipidated PSA and a detergent or bile salt.

In various embodiments, the detergent or bile salt is present in a pharmaceutically acceptable amount.

In various embodiments, the composition is a pharmaceutical composition.

In another aspect, the invention provides a non-hydrolytic method for isolating lipidated polysaccharide A (PSA) from *B. fragilis*, comprising extracting, into an aqueous phase, capsular complex from *B. fragilis* using a mixture of phenol and water, precipitating a polysaccharide fraction from the aqueous phase using ethanol, and isolating lipidated PSA from the polysaccharide fraction by size exclusion.

In various embodiments, isolating by size exclusion comprises using a chromatographic column comprising a detergent or a bile salt. In various embodiments, the chromatographic column comprises deoxycholate. In various embodiments, the method is performed in the presence of sodium deoxycholate.

In various embodiments, the method is performed at a pH less than about 9.

In various embodiments, the method further comprises dialyzing the isolated lipidated PSA.

In various embodiments, extraction occurs at 60-75° C. In various embodiments, extraction occurs at about 68° C.

In various embodiments, *B. fragilis* is a mutant form of *B. fragilis* that over-expresses PSA relative to PSB.

In various embodiments, the isolated lipidated PSA is substantially free of unconjugated glycolipid.

In another aspect, the invention provides a composition comprising isolated lipidated polysaccharide A produced by any of the foregoing methods.

In various embodiments, the composition is formulated for parenteral, enteral or oral administration to a subject.

In another aspect, the invention provides a method comprising administering, to a subject having or at risk of developing a condition associated with inflammation, an effective amount of any of the foregoing lipidated PSA or any of the foregoing compositions.

In various embodiments, the condition is an autoimmune disease. In various embodiments, the autoimmune disease is multiple sclerosis, Crohn's disease, ulcerative colitis, rheumatoid arthritis, or type I diabetes. In various embodiments, the condition is asthma.

In various embodiments, the condition is a post-surgical adhesion. In various embodiments, the composition is administered prior to, during, and/or after surgery. In various embodiments, the condition is an abscess. In various embodiments, an antibiotic is administered to the subject. In various embodiments, the condition is obesity.

In various embodiments, the composition is parenterally or enterally administered to the subject.

It is to be understood that various foregoing aspects and embodiments overlap. It is intended that the embodiments recited above apply equally to the various aspects recited above.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

It is to be understood that the Figures are not necessarily to scale, emphasis instead being placed upon generally illustrating the various concepts discussed herein.

FIG. 5 is a table listing molecular species of glycolipids derived from lipidated PSA and their proposed acyl chain composition. The table lists 5 different penta-acylated species, 5 different tetra-acylated species, 4 different tri-acylated species, and 2 different di-acylated species. The highlighted species within each grouping (for example, 1632, 1618 and 1604) represent the most abundant species. Of the penta-acylated species, the 1632 and 1618 species are the most prevalent, followed by the 1604 species, followed by the 1646 and 1590 species. Of the tetra-acylated species, the 1378 and 1364 species are the most prevalent, followed by the 1350 species, followed by the 1392 and 1336 species. Of the tri-acylated species, the 1123 and 1109 species are the most prevalent, followed by the 1095 species, followed by the 1081 species. Of the di-acylated species, the 899 and 885 species are about equally prevalent. Of all the species, the abundance of the various groups is as follows (from most to least abundant): tetra-acylated, penta-acylated, tri-acylated and di-acylated. A typical ratio of these glycolipids hydrolyzed from lipidated PSA is approximately di:tri:tetra:penta=trace: 0.5:3:2. The species listed in the Figure are typically observed in a preparation of lipidated PSA isolated using the methods provided herein. Such methods preferably do not include an acid hydrolysis step, and thereby result in a greater proportion of fully lipidated PSA being isolated relative to prior art methods. Such methods also include in some instances sodium deoxycholate or other bile salt.

These various glycolipid species differ from each other in acyl chain lengths.

FIG. 14 provides a table listing various glycolipid species obtained from a lipidated PSA preparation prepared using a non-hydrolytic method (PSA Lot 40). The table demonstrates the complexity of glycolipid component of lipidated PSA. Such complexity is imparted by differences in chain length and hydroxylation.

Figure 15:
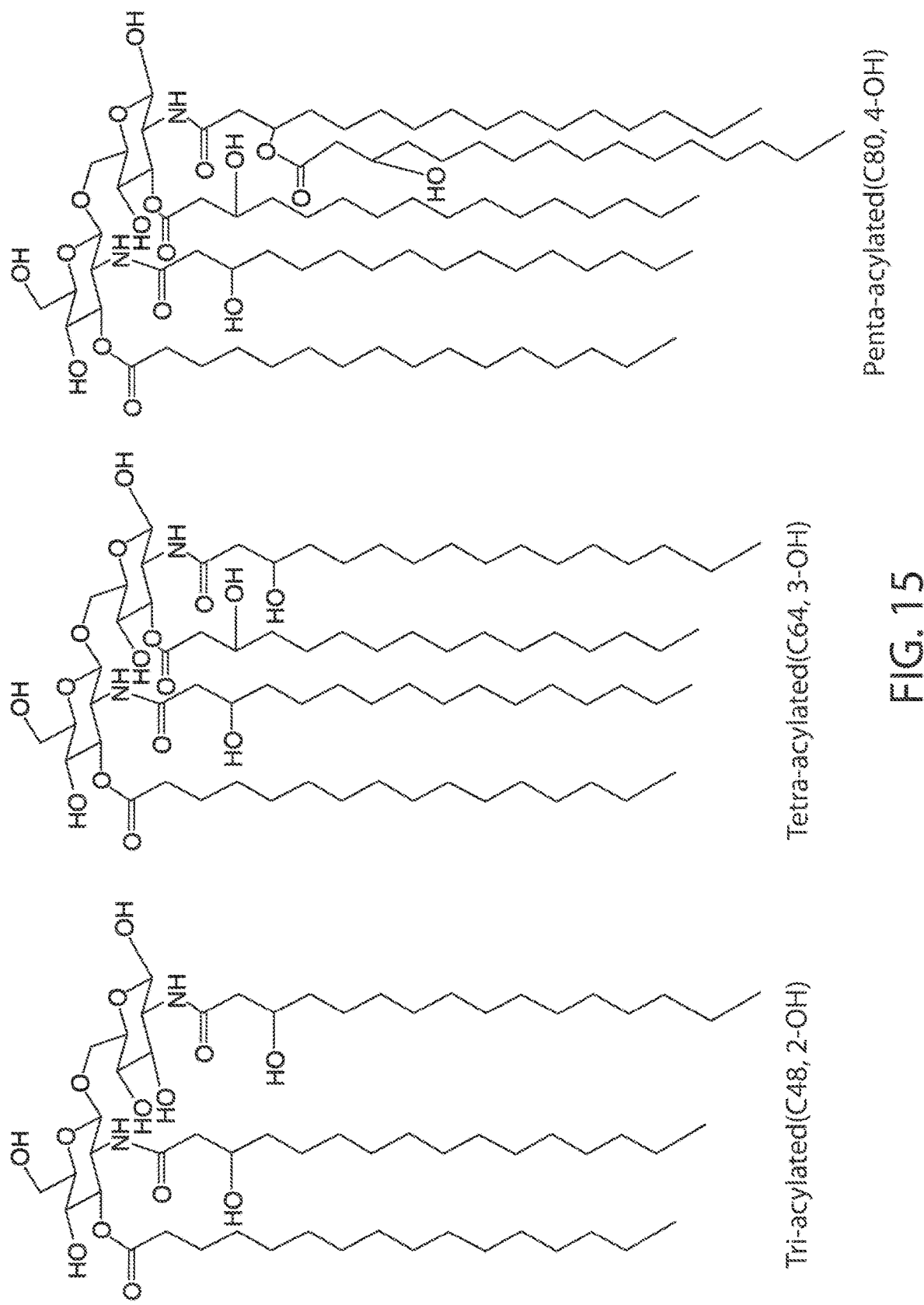

FIG. 15 provides representative structures for glycolipids species obtained from a lipidated PSA preparation prepared using a non-hydrolytic method (PSA Lot 40). Monophosphorylated variants of the illustrated compounds are also provided herein comprising a phosphate group in place of the hydroxyl at the C1 or C4' positions.

Figure 16:
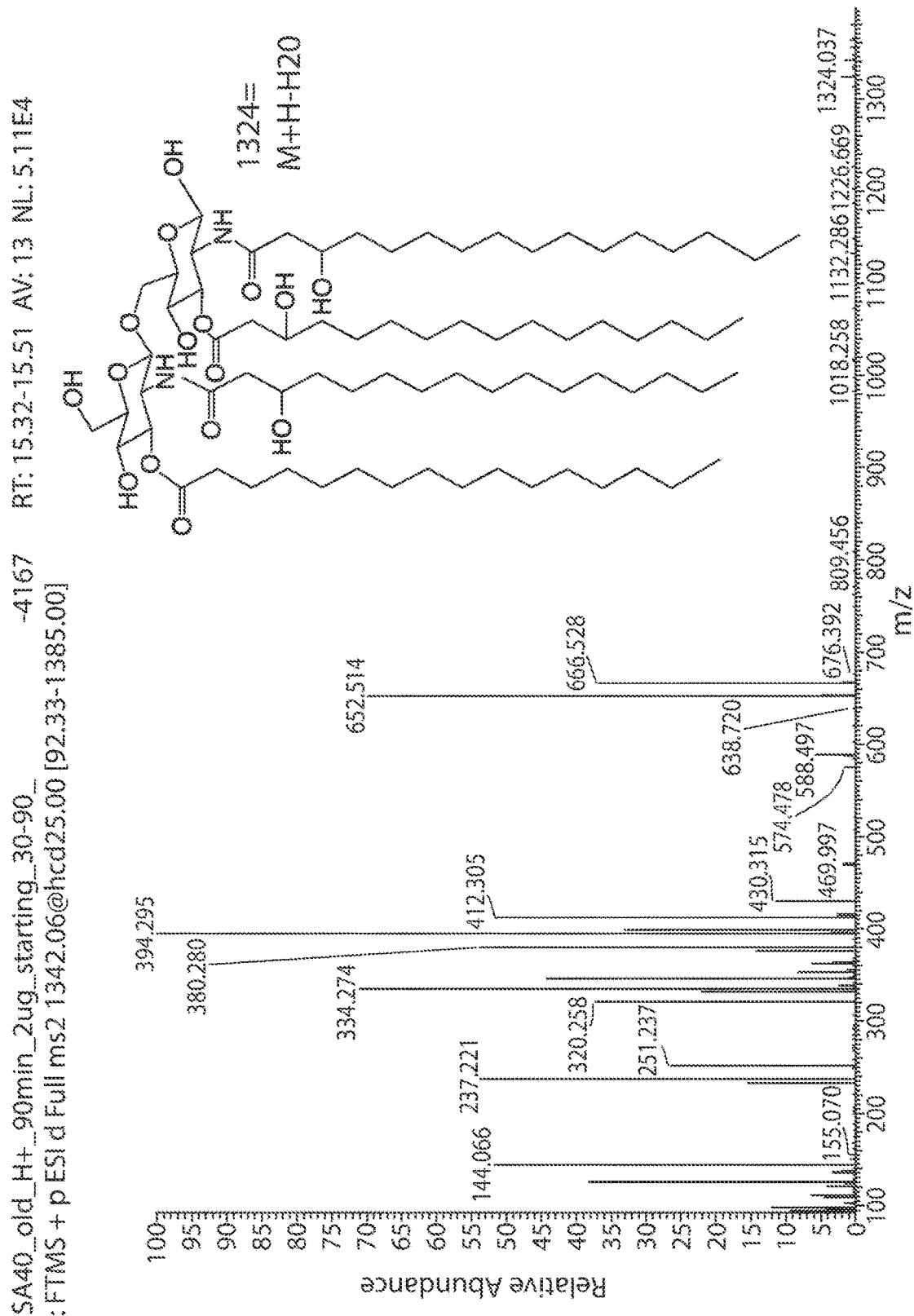

FIG. 16 provides an elution profile and a structure for glycolipid species obtained from a lipidated PSA preparation prepared using a non-hydrolytic method (PSA Lot 40). Monophosphorylated variants of the illustrated compound are also provided herein comprising a phosphate group in place of the hydroxyl at the C1 or C4' positions.

DETAILED DESCRIPTION OF THE INVENTION

Provided herein is the structural identification and characterization of the lipid moieties of lipidated PSA. It has been found in accordance with the invention that these lipid moieties are glycolipids comprised of a diglucosamine substituted with one or more acyl chains. In the naturally occurring form, the glycolipid is conjugated to its neighbouring tetrasaccharide unit through a ketosidic bond, an acid labile bond that is susceptible to acid hydrolysis. Lipidated PSA has been shown to be more immunologically potent than its non-lipidated counterpart, PSA. For example, as demonstated in the Examples, lipidated PSA is better able to induce IL-10 production (and therefore better able to interact with Treg cells) than non-lipidated PSA.

Lipidated PSA

The invention relates in part to the characterization of the lipid moiety of lipidated PSA and the newly recognized glycolipid structure and lipid complexity of lipidated PSA, and the nature of the conjugation of this glycolipid structure to PSA. It has now been discovered that lipidated PSA comprises a glycolipid moiety at the reducing end of its polysaccharide component. This glycolipid comprises a disaccharide substituted with one and typically more than one acyl chains.

Polysaccharide Component

The polysaccharide component of lipidated PSA, referred to herein as PSA, comprises a tetrasaccharide repeating unit shown below. It possesses zwitterionic behavior as conferred by a positive charge on its free amine group and a negative charge on its free carboxyl group (per repeating tetrasaccharide unit). Its naturally occurring state has been reported to comprise over 60 tetrasaccharide repeating units (e.g., up to and including in some instances about 100, or about 200, or about 300 repeated units on average), and it has an average molecular size of about 150 kD (with a range of about 75 kD to 240 kD).

The repeating tetrasaccharide unit of PSA has a structure as follows:

(Formula I)

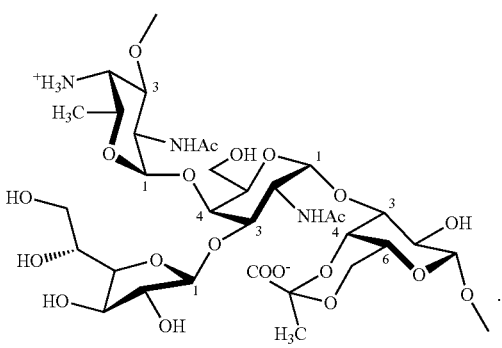

The tetrasaccharide repeating unit may also be expressed as follows:

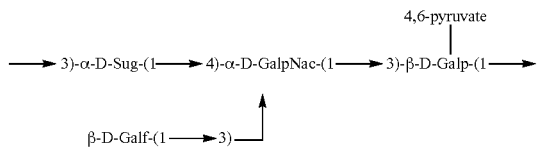

The invention contemplates synthetic forms of lipidated PSA comprising fewer tetrasaccharide units (e.g., 1-60, 1-50, 1-40, 1-30, 1-20, 1-10, 1-9, 1-8, 1-7, 1-6, or 1-5 tetrasaccharide units, or any number of units therebetween as is explicitly recite herein including but not limited to 1, 2, 3, 4, 5, 6, 7, 8, 9 and 10 units, for example). Such shorter variants can be obtained by depolymerizing naturally occurring lipidated PSA or by depolymerizing PSA obtained from lipidated PSA. PSA can be depolymerized using for example chemical means (e.g., using reactive oxygen species or reactive nitrogen species such as but not limited to nitrogen monoxide, as described in Duan and Kasper, Glycobiology, 2011, 21(4):401-409), mechanical means, and/or enzymatic means that are known in the art.

The invention further contemplates synthetic forms of lipidated PSA comprising more than 300 repeating tetrasaccharide units, including without limitation 350, 400, 500, 600, 700, 800, 900 or 1000 units or more.

As described herein, the polysaccharide component may be covalently conjugated to the glycolipid, or in certain synthetic forms it may be unconjugated to the glycolipid. If covalently conjugated, it may be conjugated via a ketosidic bond or other acid labile bond or via a bond such as an ester, an amide, or an ether bond to form a non-naturally occurring lipidated PSA.

Glycolipid Component

Figure 3:
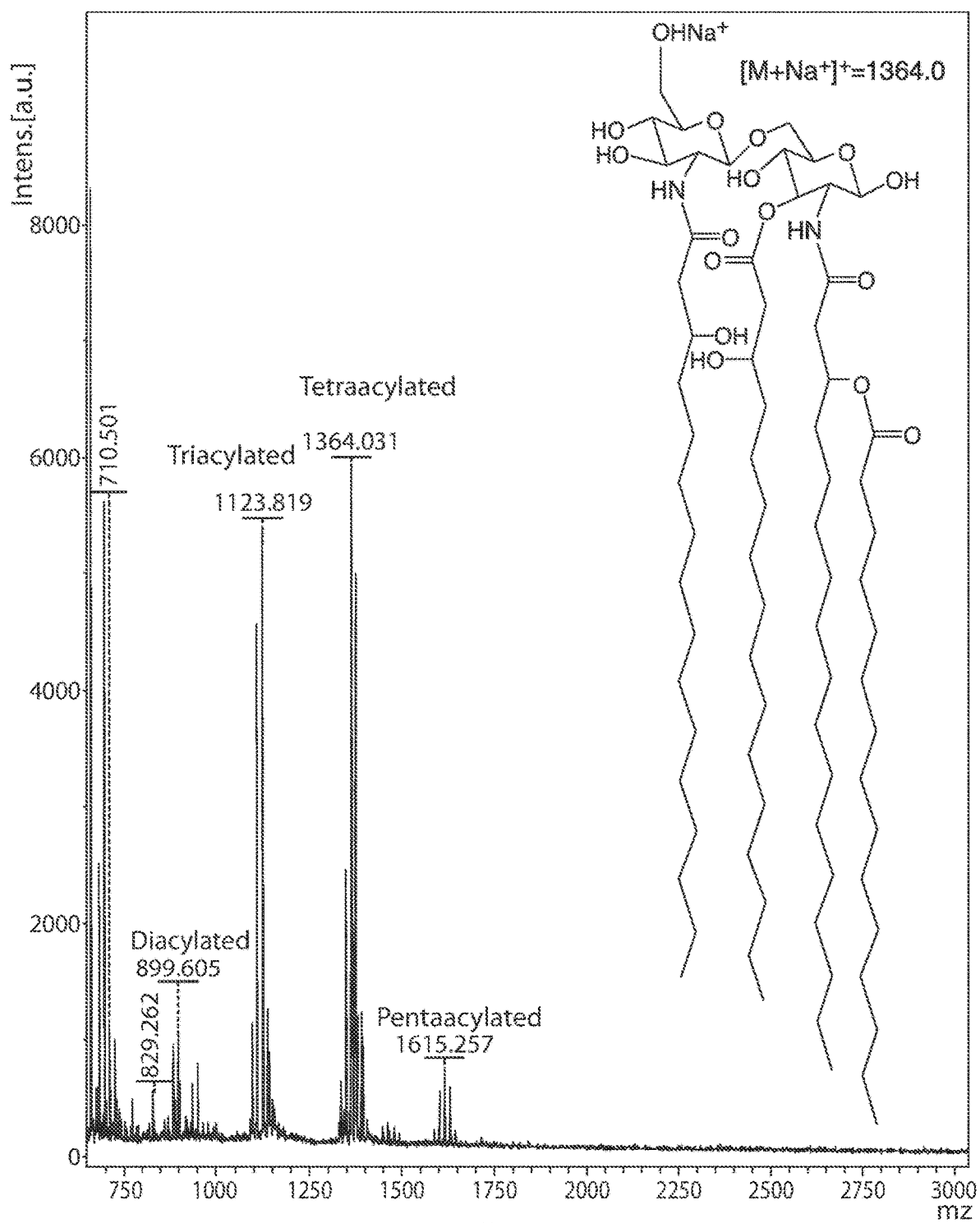
FIG. 3 is a MALDI-MS spectrum of lipid moieties released from lipidated PSA showing peaks for the di-acylated, tri-acylated, tetra-acylated and penta-acylated lipid moieties. The structure on the right is an example of a tetra-acylated glycolipid from lipidated PSA. The structure comprises hydroxyl groups at carbons C1 and C4 (carbons on the right-most substituted glucosamine (or reducing sugar)) and on carbons C3' and C4' (carbons on the left-most substituted glucosamine (or non-reducing sugar)). This disclosure embraces variants thereof that comprise a phosphate group (e.g., —OPO$_3$H) in place of the hydroxyl (—OH) at the C1 or C4' position.

The glycolipid component comprises a diglucosamine substituted with one or more acyl chains. An exemplary diglucosamine in the context of a glycolipid is provided in FIGS. 3 and 6. It is now recognized in accordance with the invention that the diglucosamine is conjugated to the polysaccharide component via a ketosidic bond that is acid-labile and thus susceptible to the stringent hydrolysis steps of the prior art methods.

The diglucosamine, in some instances, may or may not be phosphorylated. In some instances, the diglucosamine is monophosphorylated. Phosphorylation may occur at the C1 position (the reducing end) or at the C4' position of the diglucosamine.

The disaccharide may be conjugated to one or more acyl chains, including two, three, four, five or more acyl chains in some instances via for example ester or amide linkages, and thus may be referred to as "O" substituted (e.g., acylated) or "N" substituted (e.g., acylated) respectively. Each lipidated PSA molecule therefore comprises one, two, three, four, five or more acyl chains. Accordingly, the disaccharides, glycolipid components and ultimately lipidated PSA molecules may be referred to herein as di-acylated, tri-acylated, tetra-acylated or penta-acylated forms, respectively.

The acyl chains of isolated lipidated PSA may range in length from 14 to 17 carbons, in some instances. Such species are thought to represent greater than 95% of naturally occurring total lipidated PSA. The acyl chains may be unmodified or they may be modified. If modified, the acyl chains may be hydroxy-modified. Thus, in some instances, the lipidated PSA may comprise one or more acyl chains characterized as C14:0, C14:0-OH, C15:0, C15:0-OH, C16:0, C16:0-OH, C17:0, and C17:0-OH.

Figure 4:
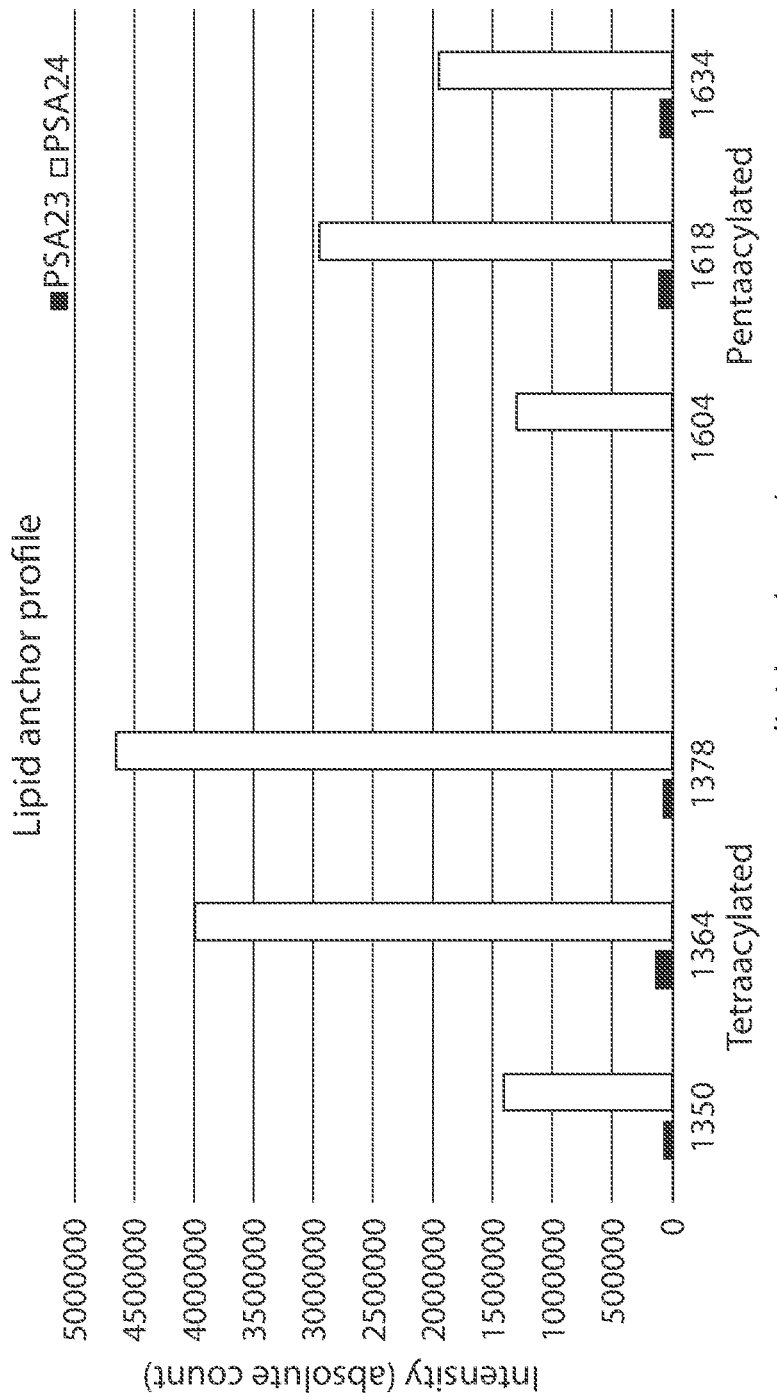
FIG. 4 is a bar graph showing quantitative analysis of lipid moieties conjugated to PSA. Six different lipid moieties are shown, each having a different MS position. The tetra-acylated lipid moieties, having an m/z in the range of about 1350-1378, and the penta-acylated lipid moieties, having an m/z in the range of about 1604-1634, are shown. For each lipid moiety, there are two bars shown: the first corresponds to a material generated using the harsher and later acid hydrolysis step (PSA 23), and the second corresponds to a material generated using the milder and earlier acid hydrolysis step (PSA 24). The Figure shows that the lipid moieties are preserved when the milder and earlier acid hydrolysis step is used. It also shows the relative proportion of the different moieties, with the m/z 1378 moiety being the most prevalent tetra-acylated version and the m/z 1618 moiety being the most prevalent penta-acylated version.

FIGS. 1, 4 and 12-16 illustrate that a single preparation of lipidated PSA may yield a number of differently acylated glycolipids. For example, in FIG. 1A, each of the peaks on the mass spectrometry (MS) spectra represents a different species of glycolipid, wherein the species differ in their acyl chain composition. The Figure illustrates this to be the case for both the tetra-acylated and the penta-acylated glycolipids. FIG. 4 illustrates the absolute amounts of a different tetra-acylated (shown as m/z 1350, 1364 and 1378) and penta-acylated (shown as m/z 1604, 1618 and 1634) glycolipid species. Thus, a bulk preparation of lipidated PSA isolated from *B. fragilis* will yield a heterogeneous mixture of lipidated PSA molecules, potentially comprising without limitation a plurality of di-acylated species and/or a plurality of tri-acylated species and/or a plurality of tetra-acylated species and/or a plurality of penta-acylated species.

FIG. 5 provides a list of glycolipid species and their acyl chain composition. For example, the Table provides penta-acylated species comprising the following combinations of acyl chains:

(1) one chain of C16:0-OH, three chains of C17:0-OH, and one chain of C15:0,
(2) two chains of C16:0-OH, two chains of C17:0-OH, and one chain of C15:0,
(3) three chains of C16:0-OH, one chain of C17:0-OH, and one chain of C15:0,
(4) four chains of C16:0-OH, and one chain of C15:0, and
(5) four chains of C16:0-OH, and one chain of C14:0.

The table similarly provides various species of tetra-acylated, tri-acylated and di-acylated acyl chains.

It will therefore be appreciated the lipidated PSA forms of the invention, whether isolated from *B. fragilis* or synthetic, and whether of conjugated or unconjugated form, may comprise any of the foregoing combinations of acyl chains, without limitation:

(1) C16:0-OH acyl chain(s) only,
(2) C17:0-OH acyl chain(s) only,
(3) C16:0-OH and C17:0-OH chain(s) only,
(4) C16:0-OH and C17:0-OH and C15:0 chain(s) only,
(5) C16:0-OH and C17:0-OH and C14:0 chain(s).

The number of each type of chain may vary, and may include without limitation the following options
(1) 0-4 C16:0-OH chains,
(2) 0-4 C17:0-OH chains,
(3) 0 or 1 C14:0 chains, and
(4) 0 or 1 C15:0 chains.

Similar diversity is apparent in another lipidated PSA preparation obtained using a non-hydrolytic method (PSA Lot 40), as illustrated in FIGS. 12-16.

The disclosure therefore provides compounds each having the following structure:

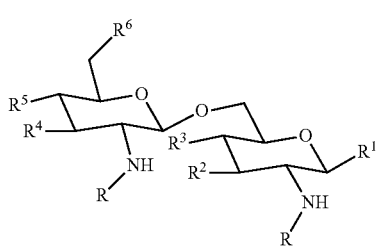

Formula I wherein:
$R^1$ and $R^5$ each independently comprises or is —OH or a phosphate such as —OPO$_3$H$^-$;
$R^2$, $R^3$, and $R^4$ each independently comprises or is —OH or —OR;
$R^6$ is —OH or —OR$^7$;
each instance of R is independently hydrogen or an optionally substituted acyl chain; and
$R^7$ is or comprises a polysaccharide.

The disclosure therefore provides compounds having the following structure:

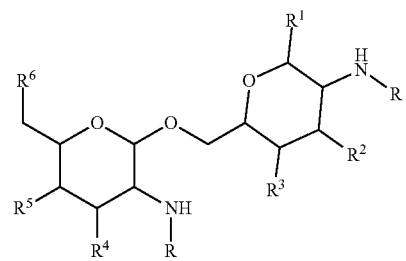

Formula II wherein:
$R^1$ and $R^5$ each independently comprises or is —OH or a phosphate such as —OPO$_3$H$^-$;
$R^2$, $R^3$, and $R^4$ each independently comprises or is —OH or —OR;
$R^6$ is —OH or —OR$^7$;
each instance of R is independently hydrogen or an optionally substituted acyl chain; and
$R^7$ is or comprises a polysaccharide.

In some embodiments, the phosphate is —OPO$_3$H$^-$. In some embodiments, the phosphate is —OPO$_3$H$_2^-$.

In some embodiments, the acyl chains are selected from any of the acyl chains provided herein, including straight and branched acyl chains.

In some embodiments, the polysaccharide is PSA or is a polysaccharide that comprises 1 or more tetrasaccharide repeating units of PSA, as described herein.

In some embodiments, R$_3$ is OH.

In some embodiments, either R1 or R5 is or comprises a phosphate (i.e., only one is or comprises a phosphate).

The foregoing examples are not to be considered limiting, and rather the invention contemplates various combinations, and combinations of the foregoing, to be used in lipidated PSA compositions.

The invention provides defined lipidated PSA mixtures, having known, and thus optionally pre-defined, glycolipid content and composition, as well as known, and thus optionally pre-defined, polysaccharide to glycolipid ratios. Thus, the lipidated PSA of the invention and compositions thereof may be characterized in terms of any of these structural features, thereby further distinguishing these compositions from those of the prior art. For example, based on the teachings provided herein, the invention provides compositions comprising lipidated PSA species that are only or predominantly (e.g., greater than 50%, or at least 55%, at least 60%, at least 65%, at least 70%, at least 75%, at least 80%, at least 85%, at least 90%, or at least 95%) di-acylated, or tri-acylated, or tetra-acylated, or penta-acylated, or some combination thereof including but not limited to tetra- and penta-acylated. Such chemically defined compositions were not heretofore contemplated or possible.

The invention further provides isolated glycolipids obtained from lipidated PSA and compositions thereof for use in vivo and in vitro. Any of the foregoing glycolipids and any combination of the foregoing lipids are contemplated for such use.

Isolated Forms

As described herein, it has been found, in accordance with the invention, that the method of isolation can significantly impact the abundance, impacting yield and purity, of isolated lipidated PSA. For example, it has been found that isolation methods that exclude an acid hydrolysis step yield more intact, fully lipidated PSA species than do methods that include an acid hydrolysis step, even if that acid hydrolysis step occurs earlier in the isolation process. In other words, when the lipidated PSA is harvested from B. fragilis using an acid hydrolysis step, some fraction of the originally lipidated PSA will become delipidated in the process. This can be seen for example by running the preparation on a 16.5% Tris-Tricine SDS-PAGE gel reverse stained with zinc sulphate/imidazole staining, as shown for example in FIG. 10 which compares a lipidated PSA isolated using a mild acid hydrolysis (Lot 28) and lipidated PSA isolated without an acid hydrolysis step (Lot 34). This staining protocol allows one to observe both the polysaccharide and lipid moieties of lipidated PSA in the same gel system. It has been found that the lipidated PSA preparations of the prior art contained a higher degree of released glycolipid than do the lipidated PSA preparations of the instant invention.

The preparations provided herein therefore can be characterized by their content of released or free glycolipids. Such content can be less than 5%, less than 4%, less than 3%, less than 2%, less than 1%, less than 0.5%, less 0.1%, less than 0.05%, less than 0.001%, less than 0.0005%, less than 0.0001% (w/w of released glycolipid to lipidated PSA). In some instances, the compositions or preparations have undetectable levels of released or free glycolipids, as determined for example using the gel electrophoresis methods described herein. In these instances, the lipidated PSA may be considered free or substantially free of released glycolipid. The lipidated PSA may also be considered to be pure (i.e., it is free or substantially free of released glycolipid and any other naturally occurring contaminant). The degree of purity may be at least 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9%, or higher.

Accordingly, the invention provides compositions comprising isolated lipidated PSA, including compositions comprising isolated lipidated PSA at a purity and/or a concentration that has not been heretofore achieved. Also provided are compositions comprising or consisting essentially of particular species of lipidated PSA or particular subsets of species of lipidated PSA. These species may be characterized and thus distinguished from other species and from bulk isolated lipidated PSA in terms of their glycolipid components. The glycolipid components may be characterized by the number, position and type of acyl chains they possess. For example, they may comprise an increased amount, relative to naturally occurring proportion, of di-acylated, tri-acylated, tetra-acylated, or predominantly penta-acylated forms of lipidated PSA. These increased amounts may exceed the naturally occurring representation of the particular species, and thus such amounts will vary depending on the particular species. For example, a composition may comprise at least 5%, 10%, 15%, 20%, or more of a di-acylated lipidated PSA, or it may comprise at least 70%, 75%, 80%, 85%, 90%, 95%, or more of a tetra-acylated and/or penta-acylated lipidated PSA.

The compositions may be defined by their degree of purity, for example with respect to their glycolipid components, or with respect to their content of contaminants such as non-lipidated PSA. The compositions may be defined by their concentration of lipidated PSA, or by their concentration of PSA components and/or glycolipid components, or by their ratio of PSA to glycolipid components.

Synthetic Forms

The invention further provides additional synthetic, non-naturally occuring species of lipidated PSA. In some instances, these non-naturally occurring species are characterized as having a lower tetrasaccharide/glycolipid ratio (or a lower PSA/glycolipid ratio, wherein the PSA is the polymer comprised of one or more repeating tetrasaccharide units) than is observed in isolated forms of lipidated PSA. Such ratio may be a molar ratio or a molecular weight ratio. The invention further provides other compositions comprising polysaccharide (PSA) or tetrasaccharide and glycolipid and/or lipid components obtained or derived from lipidated PSA, in a non-naturally occurring conjugated form. For example, the polysaccharide and glycolipid components may be conjugated to each other via a non-naturally occurring linkage. The linkage may be a non-ketosidic linkage, and may be an ester or an amide or an ether, without limitation. In other compositions, the components, such as the polysaccharide and glycolipid components, may be unconjugated. In still other compositions, a substrate in or on which the polysaccharide (or tetrasaccharide) and glycolipid (or lipid) components, whether conjugated or unconjugated, are present in or on a substrate or delivery vehicle.

All of these various forms of lipidated PSA, including for example those isolated from B. fragilis cells, those made synthetically and having different polysaccharide/glycolipid ratios from isolated forms, those provided as unconjugated polysaccharide and glycolipid components, and the like, are considered to be active agents. Various aspects and embodiments relating and referring to "lipidated PSA" apply equally to these various forms and are not meant to apply solely to an isolated form or to a covalently conjugated form unless otherwise indicated or apparent.

Lipidated PSA Compositions

The invention further provides compositions comprising isolated lipidated PSA. As used herein, with respect to lipidated PSA, the term "isolated" intends that the lipidated PSA is prepared or obtained from B. fragilis, and is physically separated from its natural environment (e.g., a B. fragilis cell, components of the B. fragilis cell, and/or components of the B. fragilis cell capsular complex such as but not limited to PSB).

In some embodiments, the compositions are substantially free of naturally occurring contaminants such as nucleic acids (e.g., DNA and RNA), proteins, and other components of B. fragilis and/or the B. fragilis capsule. Substantially free, as used herein, intends that these contaminants represent about or less than 5%, less than 1%, less than 0.5%, or less than 0.1% (or less) by weight (weight of the contaminant to weight of the lipidated PSA form). In some instances, such contaminants may be undetectable.

Various compositions may or may not contain LPS. LPS may be present in an amount of about 0.5% (w/w of LPS to lipidated PSA components).

Some compositions may comprise at least about 95%, 96%, 97%, 98%, 99%, or more (w/w) of lipidated PSA and less than 5%, less than 4%, less than 3%, less than 2%, less than 1%, less than 0.5%, or less of free, released glycolipid. In some embodiments, the free, released glycolipid is undetectable.

Thus, certain compositions comprising lipidated PSA, whether of isolated or synthetic form, may or may not comprise other components including LPS and/or free, released glycolipid. In some embodiments, the amount of LPS present in such compositions is about 0.5% (w/w) or less. In some embodiments, the amount of released or free glycolipid to lipidated PSA is about 0.5% (w/w) or less. In various other embodiments, the amount of non-lipidated PSA present in such compositions is about 10% (w/w) or less, including 5% or less, or 1% or less. In some embodiments, the compositions are substantially free of non-lipidated PSA.

The presence and amount of these various components and contaminants including lipidated PSA, released (unconjugated) glycolipid, and/or LPS can be determined using a gel system such as that described herein.

Some compositions of lipidated PSA may comprise at least about 50%, 55%, 60%, 65%, 70%, 75%, 80%, 85%, 90%, 95%, 99%, or more of the polysaccharide component (non-lipidated PSA) (weight of polysaccharide to combined weight of polysaccharide and glycolipid). Some compositions of lipidated PSA may comprise about 50%, 45%, 40%, 35%, 30%, 25%, 20%, 15%, 10%, 5%, 1%, or less of the glycolipid component (weight of glycolipid to combined weight of polysaccharide and glycolipid). Some compositions of lipidated PSA may comprise about 99% polysaccharide component (non-lipidated PSA) and about 0.5% glycolipid component. Some compositions of lipidated PSA may comprise about 80% polysaccharide component (non-lipidated PSA) and about 20% glycolipid component. These may be isolated or synthetic forms of lipidated PSA. Accordingly, they may be forms in which the polysaccharide and glycolipid components are conjugated to each other or they may be forms in which these components are not conjugated to each other. Conjugation may be direct or indirect conjugation, and additionally it may be covalent or non-covalent conjugation. It is to be understood that the polysaccharide and glycolipid components are lipidated PSA components (i.e., the polymer formed of one or more tetrasaccharide units of Formula I and the glycolipid described herein and comprising a disaccharide conjugated to one or more acyl chains).

Figure 6A:
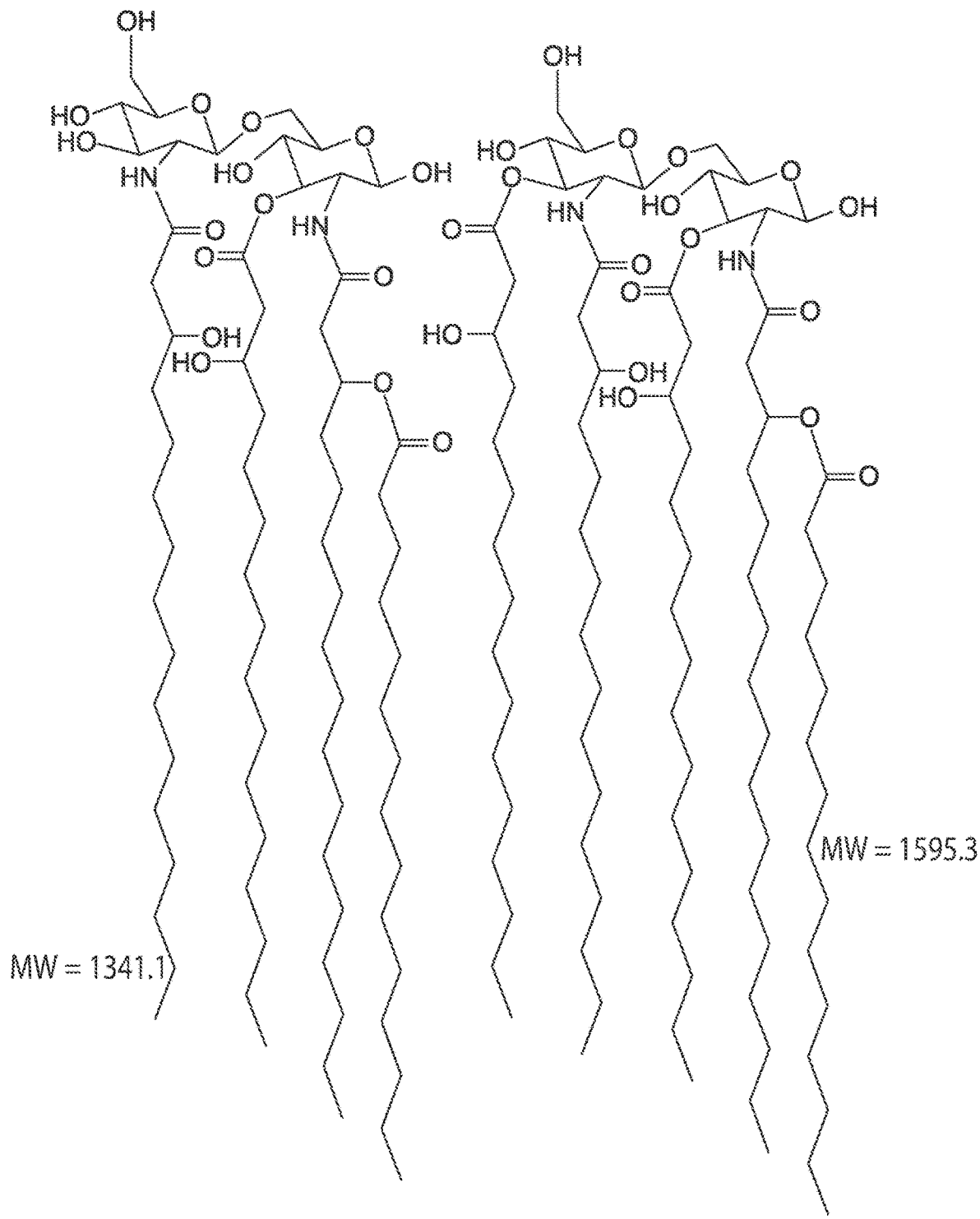
FIG. 6A provides representative structures of glycolipids from lipidated PSA. A representative tetra-acylated diglucosamine having a moleculear weight of about 1341.1 is shown on the left (referred to herein as Formula II), and a representative penta-acylated diglucosamine having a molecular weight of about 1595.3 is shown on the right (referred to herein as Formula III). The tetra-acylated structure at the left comprises hydroxyl groups at the C1, C4, C3' and C4' positions. The penta-acylated structure at the right comprises hydroxyl groups at the C1, C4 and C4' positions. Monophosphorylated variants of these compounds are also provided herein comprising a phosphate group in place of the hydroxyl at the C1 or the C4' position.
Figure 6B:
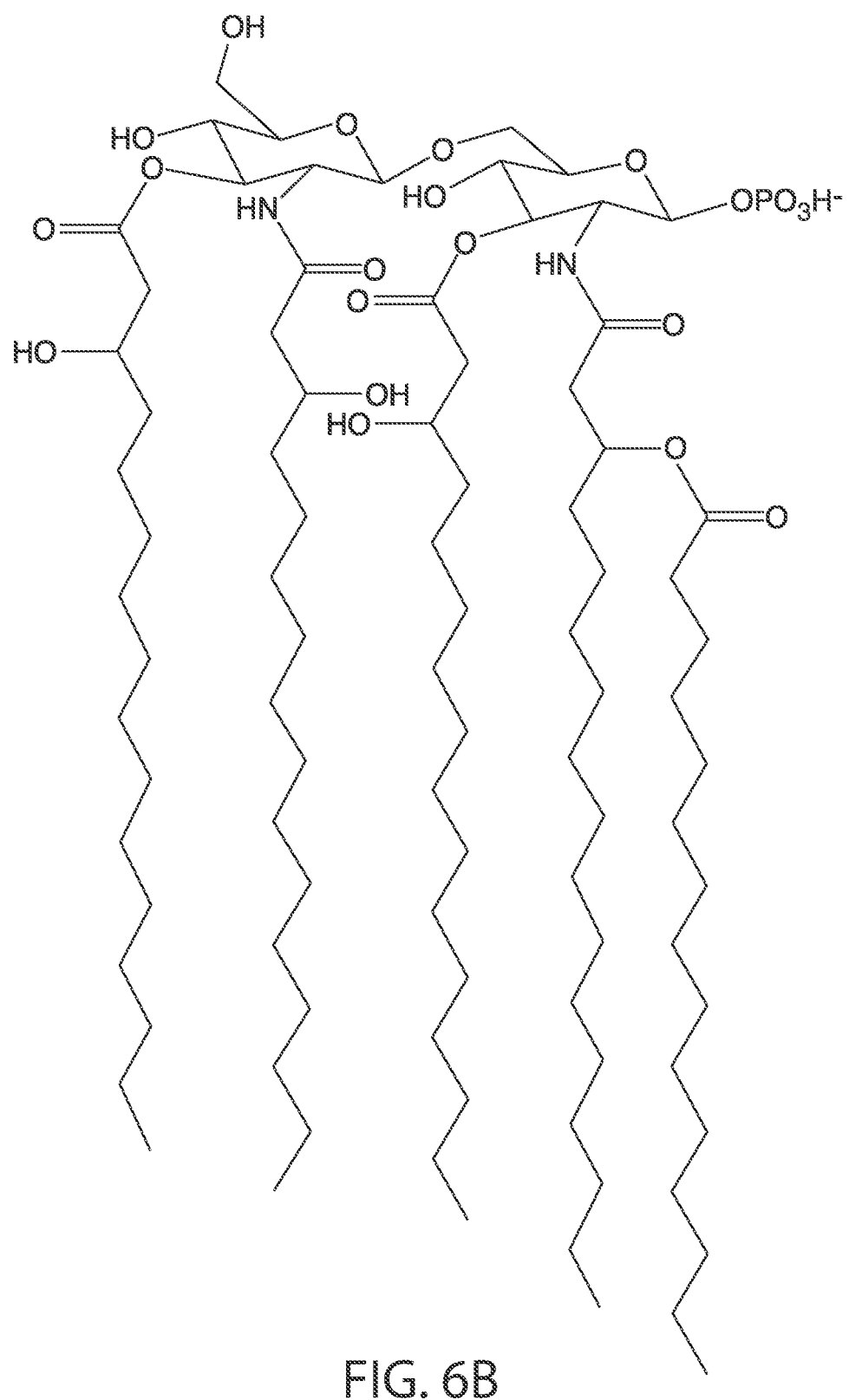
FIG. 6B provides a pentaacylated, monophosphorylated species of glycolipid. The phosphorylation exists at the C1 position.

As an example, in one instance, the composition may comprise a synthetic form of lipidated PSA having 6 tetrasaccharide units and one tetra-acylated glycolipid unit (see for example Formula II in FIG. 6A). The compositions may comprise about 20% glycolipid and 80% polysaccharide (w/w as defined above). Synthetic compositions may be defined by their glycolipid and polysaccharide components, amounts and ratios, whether such components are conjugated or unconjugated to each other. Other compositions and combinations are contemplated and will be readily appreciated by those of ordinary skill in the art.

It is to be understood that the compositions of the invention typically comprise a plurality of lipidated PSA molecules, and that in some instances the plurality may exhibit variation in the degree or nature of lipidation. The invention contemplates compositions have particular proportions of particular species of lipidated PSA and/or particular subsets of lipidated PSA. The proportions may be w/w proportions (e.g., weight of the particular species to weight of all lipidated PSA in the composition). Such proportions may be about or more than 5%, 10%, 15%, 20%, 25%, 30%, 35%, 40%, 45%, 50%, 55%, 60%, 65%, 70%, 75%, 80%, 85%, 90%, 95%, or more of a defined species or subset of species. For example, a particular species may be a lipidated PSA comprising the glycolipid of Formula II or a lipidated PSA comprising the glycolipid of Formula III, or a lipidated PSA comprising any one of the acyl chain combinations listed in FIG. 5. A particular subset of lipidated PSA species may be lipidated PSA comprising tetra-acylated glycolipids, or lipidated PSA comprising penta-acylated glycolipids, or lipidated PSA comprising tetra- or penta-acylated glycolipids. Various subsets are contemplated and will be apparent based on this disclosure.

The invention provides compositions for use in vitro and in vivo. In vitro, the compositions may be used as analytical tools or assay standards. In vivo, the compositions may be used or in experimental models, such as animal models, of human disease or in humans or other subjects in need of immune regulation. When used in vivo, the compositions are pharmaceutically acceptable, intending that they are suitable for administration into a subject. They may or may not be used prophylactically or therapeutically in such subjects.

The lipidated PSA forms may be used as stand-alone active agents or they may be used in combination with other active agent(s). The combined use of agents may be additive or may be supra-additive (e.g., synergistic). The lipidated PSA forms may be formulated together with or separately from the other active agent(s). The lipidated PSA forms may be administered via the same or a different route from the other active agent(s). If not formulated together, the lipidated PSA forms and the other active agent(s) may be administered on the same or substantially the same administration regimen (including being administered substantially simultaneously although not formulated together) or they may be administered according to different regimen. The lipidated PSA forms may be administered acutely and/or chronically.

Isolation and Synthesis Methods

The invention further provides methods of isolating and purifying lipidated PSA from *B. fragilis* as well as methods of making the various synthetic forms of lipidated PSA described herein.

It was recently recognized that prior art methods used to isolate and purify PSA removed the lipid moiety from the polysaccharide, thereby previously yielding only a polysaccharide structure for PSA. See published PCT application WO 2013/009945. However, the nature of the lipid moiety and its particular attachment to PSA was not known until the present invention.

Isolation Methods

In accordance with the invention, it was found that lipidated PSA could be isolated in the absence of a hydrolysis step. Thus provided herein are non-hydrolytic methods for isolating lipidated-PSA from *B. fragilis* strains (i.e., methods that lack a hydrolysis step such as an acid hydrolysis step). It was not previously recognized that lipidated PSA could be isolated from *B. fragilis* strains without a hydrolysis step.

It was also found that the lipidated PSA could be isolated in the presence of a bile salt such as deoxycholate. Previously it was thought that the presence of detergents or bile salts such as sodium deoxycholate were detrimental to the isolation process, resulting in lower yields of the lipidated PSA. Unexpectedly, various methods provided herein which lack a hydrolysis step and optionally which utilize a detergent (such as deoxycholate) provide suitable yields of lipidated PSA and in some instances higher yields of lipidated PSA. Excluding the acid hydrolysis step entirely from the isolation process prevents hydrolysis of the glycolipid from PSA, thereby resulting in a greater proportion of lipidated PSA versus non-lipidated PSA. This is evidenced by the reduced and in most instances undetectable amount of released (unconjugated) glycolipid in such preparations. The released glycolipid can be observed using any of the analysis techniques described herein including gel electrophoresis or mass spectrometry.

In some instances, such methods involve isolating lipidated PSA using the isolation methods described herein, and purifying the isolated lipidated PSA to arrive at purity and/or concentration levels not heretofore achieved. Such purity and/or concentration levels may be apparent by the degree of aggregation of the lipidated PSA (e.g., as micelles), and optionally the effect of disagreggating agents such as deoxycholate to increase the biological activity of such compositions, as demonstrated herein.

Since the lipidated PSA is considered more biologically active than non-lipidated PSA, the isolation methods provided herein yield lipidated PSA having a higher activity per weight than previously described preparations. Such activity may be IL-10 inducing activity, for example.

The method provides general and specific methods for isolating and purifying lipidated PSA from B. fragilis. It is to be understood that these methods may be performed on any strain of B. fragilis provided it produces lipidated PSA. Such strains include naturally occurring strains or non-naturally occurring stains. One example of a non-naturally occurring strains is the delta44 mutant of B. fragilis strain 9343. This mutant strain expresses only PSA, rather than PSA and PSB as found in wild type strains such as 9343.

The methods of isolation generally involve growth of B. fragilis (wild type or mutant strains) under anaerobic conditions, extraction of the polysaccharide capsular complex from B. fragilis, isolation of a polysaccharide fraction, and purification of lipidated PSA from that fraction. The extraction step may be accomplished using a phenol/water extraction, which optionally can be carried out at an elevated temperature (e.g., about 60-80° C.). The aqueous phase, which contains the capsular polysaccharides, is then dialyzed versus water, following which it may be partially lyophilized in order to reduce total volume. The resulting solution is then typically treated with nucleases such as DNase and RNase and proteinases such as pronase in order to further purify the polysaccharide fraction. The polysaccharide fraction is then ethanol precipitated, and the precipitate is collected, washed, and subjected to size exclusion techniques to further isolate the lipidated PSA from other polysaccharides including for example LPS. A typical size exclusion technique is column chromatography. A suitable column is a S-400 size exclusion column. A chromatographic column containing a biological detergent in the form of sodium deoxycholate was used to isolate lipidated PSA, as described in the Examples. Column fractions containing the lipidated PSA are identified and pooled, and the pooled mixture can then be further dialyzed and lyophilized if desired. Additionally, after reconstitution, the mixture may be further dialyzed, ethanol precipitated and/or lyophilized for storage or delayed use. The pH throughout the isolation preferably is 9 or less (e.g., about 4 to about 9 or less), and in most steps is maintained in a neutral range.

The foregoing method may be performed without an acid hydrolysis step. However, it is to be understood that lipidated PSA, and species and subsets of species thereof, may be harvested using methods that include an acid hydrolysis step and/or a size exclusion step without the use of a detergent such as sodium deoxycholate.

If an acid hydrolysis step is used, it is preferably a mild hydrolysis (e.g., at a pH of about 4, or in the range of 4-5) and it is preferably incorporated at an early step in the purification process (e.g., following the first ethanol precipitation). The acid hydrolysis, if used, may be performed using dilute acid (e.g., 1-2% acetic acid) at elevated temperature. The elevated temperature may range from 80-100° C., 85-95° C., and in some instances may be about 90° C. The treatment may last for 1 hour, 2 hours, 3 hours or longer. In some instances, the acid treatment is performed using 2% acetic acid at 90° C. for 3 hours.

The foregoing method may be performed using a detergent or a bile salt such as deoxycholate (e.g., sodium deoxycholate) in the chromatographic column and/or the eluent. Sodium deoxycholate may be present at a strength of less than 5%, less than 4%, less than 3%, less than 2%, or about or less 1%. However, it is to be understood that lipidated PSA may be harvested using methods that include a size exclusion step that does not use a detergent such as deoxycholate.

Thus, an exemplary isolation method comprises extracting, into an aqueous phase, a capsular complex from B. fragilis using a mixture of phenol and water optionally at high temperature, precipitating a polysaccharide fraction from the aqueous phase using ethanol optionally following DNA and/or RNA and/or protein digestion, and isolating lipidated PSA from other polysaccharides by size exclusion, such as for example a chromatographic column containing sodium deoxycholate.

The lipidated PSA forms prepared from B. fragilis once isolated may be further modified. For example, the polysaccharide component may be depolymerized to produce another non-naturally occurring form having fewer tetrasaccharide units than are found in nature. This can be accomplished through mechanical, chemical or enzymatic means. An example of chemical depolymerization involves reactive oxygen species or reactive nitrogen species such as but not limited to nitrogen monoxide, as described in Duan and Kasper, Glycobiology, 2011, 21(4):401-409). Glycosidases can be used for enzymatic depolymerization. Mechanical depolymerization may involve shearing. As an example, the PSA polymer may be shortened by 25%, 50%, 75%, or more, thereby rendering a lipidated PSA that is structurally different from naturally occurring lipidated PSA. Such modification may generate PSA or lipidated PSA having a length of about 50, 40, 30, 20, or to about 1-10 tetrasaccharide units.

Lipidated and non-lipidated versions of PSA can be depolymerized and fractionated according to polysaccharide length using for example liquid chromatography, ion chromatography, or other size-based or ion-based separation techniques.

Isolated forms of lipidated PSA may be formulated alone, in which case they form tight micelle-like structures. Significantly, lipidated PSA does not form such micelle-like structures when present in vivo. Such altered structure is only observed (and thus possible) upon isolation of the lipidated PSA in a relatively pure form. Furthermore, these micelle-like structures are so stable that detergent or other disaggregating agent may be necessary to disrupt them or to render them less stable, thereby making the lipidated PSA contained therein accessible.

In these various non-naturally occurring forms, the acyl chains are situated externally in the micelle-like structure and thus are accessible to target cells and their receptors. Such cells include antigen presenting cells and such receptors include TLRs such as TLR2. See Wang et al. J. Exp. Med 203(13): 2853-63 and Round et al. Science 2011, 332(6032):974-7.

The isolated lipidated PSA may also be fractionated based on the nature of the glycolipid such that resulting compositions comprise non-naturally occurring ratios of di-, tri-, tetra-, and penta-acylated PSA.

Thus, this disclosure contemplates additional non-naturally occurring species of lipidated PSA having fewer tetrasaccharide units compared to naturally occuring lipidated PSA.

Other Methods

The synthetic lipidated PSA forms of the invention may be prepared using naturally occurring or synthetically produced forms of the polysaccharide and glycolipid components. Naturally occurring forms may be prepared by deliberating hydrolyzing (e.g., acid-treating) lipidated PSA thereby cleaving the ketosidic linkage between the polysaccharide and glycolipid. The polysaccharide and glycolipid components may be separated from each other and thereby isolated using liquid chromatography, ion chromatography, gel electrophoresis or other size-based or charge-based separation technique.

The polysaccharide may be further modified by mechanical, chemical and/or enzymatic means. This may serve to reduce the length of the polysaccharide component, if desired. The polysaccharide (PSA) can be depolymerized using for example mechanical and/or enzymatic means known in the art and described herein.

Similarly, the invention contemplates fractionating the naturally occurring glycolipids obtained from lipidated PSA according to their degree of acylation and then recombining particular subsets with the polysaccharide component. For example, the penta-acylated or the tetra-acylated glycolipid subsets may be isolated and recombined with the polysaccharide components. The end-products may comprise the naturally occurring linkage between glycolipid and polysaccharide or they may comprise non-naturally occurring linkages such as esters, amides, ethers or a combination thereof. Polysaccharides and glycolipids can also be conjugated via a bifunctional linker molecule, such as, but not limited to, 2-(Boc-amino)ethyl bromide. Other linker molecules may be used, and are known in the art.

Alternatively, components of lipidated PSA may be synthesized and then combined. For example, the glycolipid may be synthesized and then used with the polysaccharide component isolated from B. fragilis. For example, glycolipid may be synthesized using techniques described in Imoto et al (Tet. Lett. 1984, 25:25, 2667-2670). These techniques may be used to produce both conjugated and unconjugated forms of synthetic lipidated PSA. It is to be understood that for brevity, as used herein, the term "lipidated PSA" embraces synthetic forms that comprise polysaccharide and glycolipid components provided together but in an unconjugated form (e.g., in or on a substrate, as described below).

Synthetic lipidated PSA forms may be provided with, including in and/or on a substrate. The substrate may be a solid or semi-solid and it may take any one of a variety of shapes or forms. The substrate may be biodegradable and itself may be composed of naturally occurring and/or non-naturally occurring components such as but not limited to naturally occurring and/or non-naturally occurring polymers. One example of a suitable substrate is a particle. The particle may be a microparticle (average diameter in the range of 1-999 microns) or a nanoparticle (average diameter in the range of 1-900 nanometers). The particle may be a porous particle or it may be a non-porous particle. Methods for producing such particles having active agents therein or thereon are known in the art. Thus, the invention contemplates the use of any of such methods and any of such particles to prepare certain compositions of lipidated PSA as contemplated herein.

In some instances, the glycolipid or PSA components are conjugated to the surface of the particle.

In some instances, glycolipid and PSA components are provided in a liposome or liposome-like structure. The glycolipid component may be external and the polysaccharide component may be internal to the liposome. The liposome may comprise solely the glycolipid and PSA components from lipidated PSA or it may comprise other components such as but not limited to other lipids. The externally facing lipid component is believed to interact with TLR2 on antigen-presenting cells, thereby facilitating entry into such cells of the liposome and intracellular release of the PSA component.

The liposome or micelle forms of the naturally or non-naturally occurring lipidated PSA will typically comprise the glycolipid component at the surface and available for interaction with cells and particular receptor such as TLR2.

The lipidated PSA may be formulated to target specific cell types, for greater therapeutic efficacy. For example, if the lipidated PSA, whether isolated or synthetic, is provided in the context of a substrate such as a nanoparticle, then the substrate may further comprise moieties that increasing homing or binding of the substrate to immune cells such as antigen-presenting cells (APC) including dendritic cells and B cells.

Examples of non-naturally occurring forms of lipidated PSA include those comprising a non-naturally occurring linkage between the glycolipid and polysaccharide components, those having PSA polymers that are shorter or longer than naturally occurring forms of lipidated PSA, those that are present in a proportion lower or higher than their naturally occurring proportion, or those that have some combination or all of these features.

Methods for Analysis and Characterization of Lipidated PSA

The invention provides methods for detecting the presence of lipidated PSA and in some instances quantitating the amount of lipidated PSA in a sample or a composition.

Structural Characterization

Purity of the isolated fractions may be assessed by proton NMR and/or SDS PAGE gel. Proton NMR profiles may be generated using 600 MHz NMR. Other compositions may be tested for the presence of lipidated PSA in a similar manner.

Figure 1A:
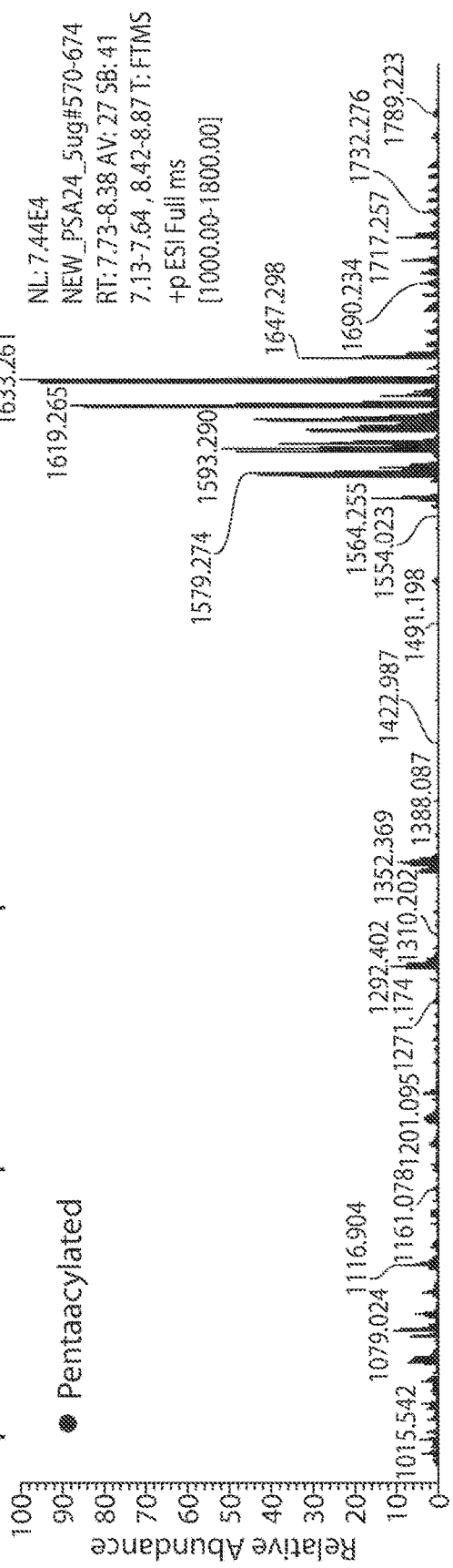
FIG. 1A provides representative mass spectrometry (MS) spectra for tetra-acylated (bottom) and penta-acylated (top) glycolipids released from lipidated PSA.
Figure 1A:
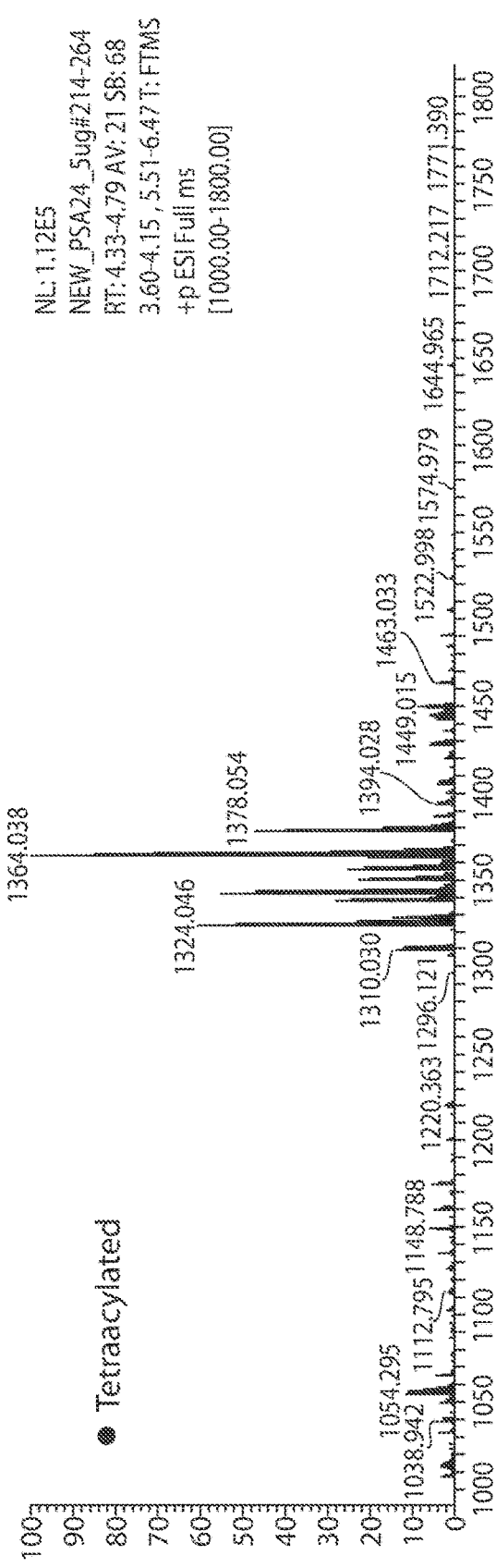
Figure 1B:
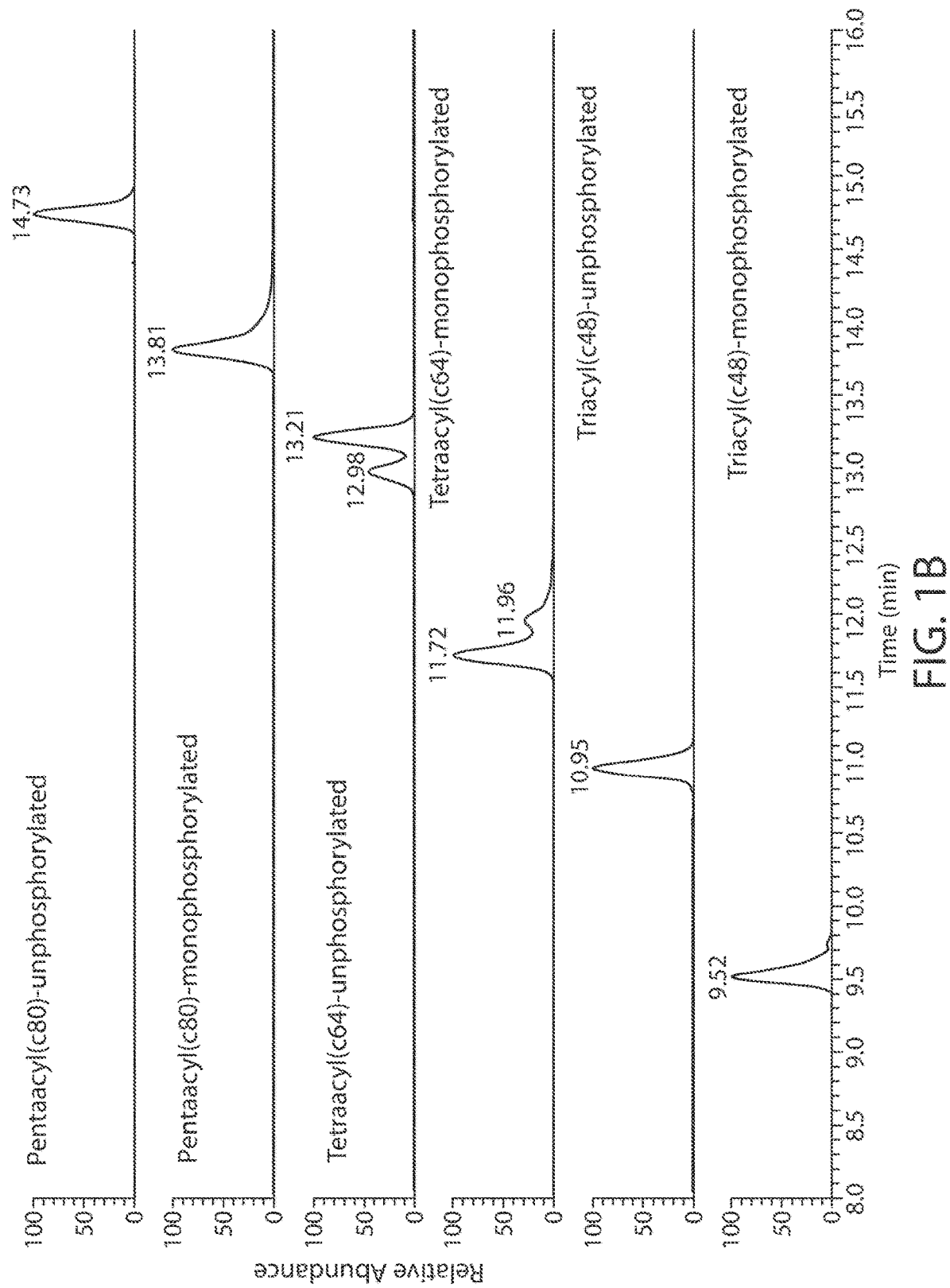
FIG. 1B provides LC-MS/MS profiles for *B. fragilis* PSA glycolipid anchors showing monophosphorylated and unphosphorylated glycolipid species having different numbers of acyl chains. Species with the same number of acyl chains may still differ from each other with respect to total chain length and/or nature (composition) of such acyl chains. In some instances, ~30 total glycolipid species have been identified within a group of species having the same number of acyl chains.
Figure 2A:
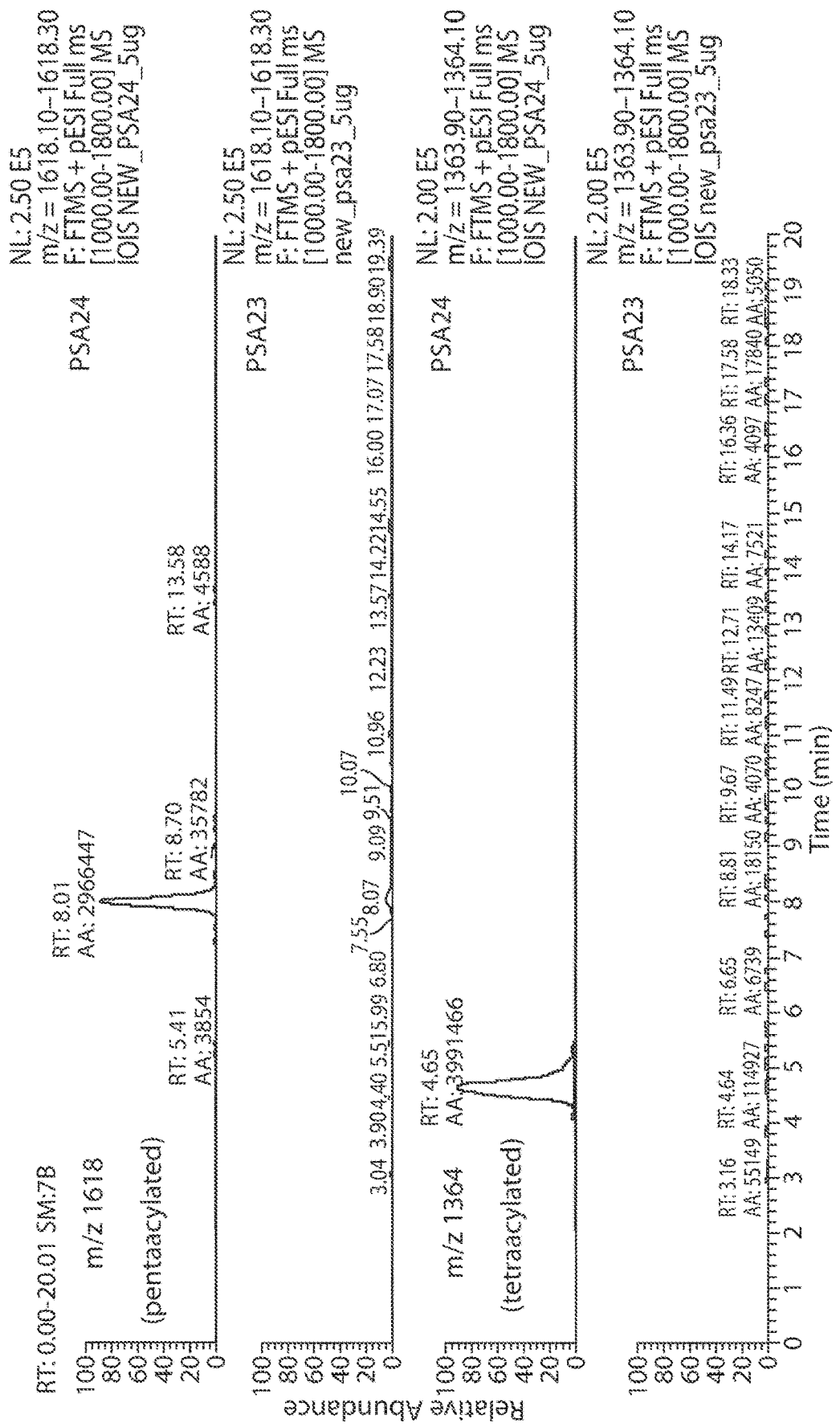
FIG. 2A provides a comparison of the MS spectra for penta-acylated glycolipids (from the top, panels 1 and 2) and tetra-acylated glycolipids (from the top, panels 3 and 4) released from lipidated PSA. The material in panels 1 and 3 was obtained using a mild hydrolysis step earlier in the isolation process. The material in panels 2 and 4 was obtained using a harsher hydrolysis step later in the isolation process. The lipid moieties are detectable in panels 1 and 3 but not detectable in panels 2 and 4, evidencing the detrimental effect of the harsher and later in time acid hydrolysis step on the lipid moieties.
Figure 2B:
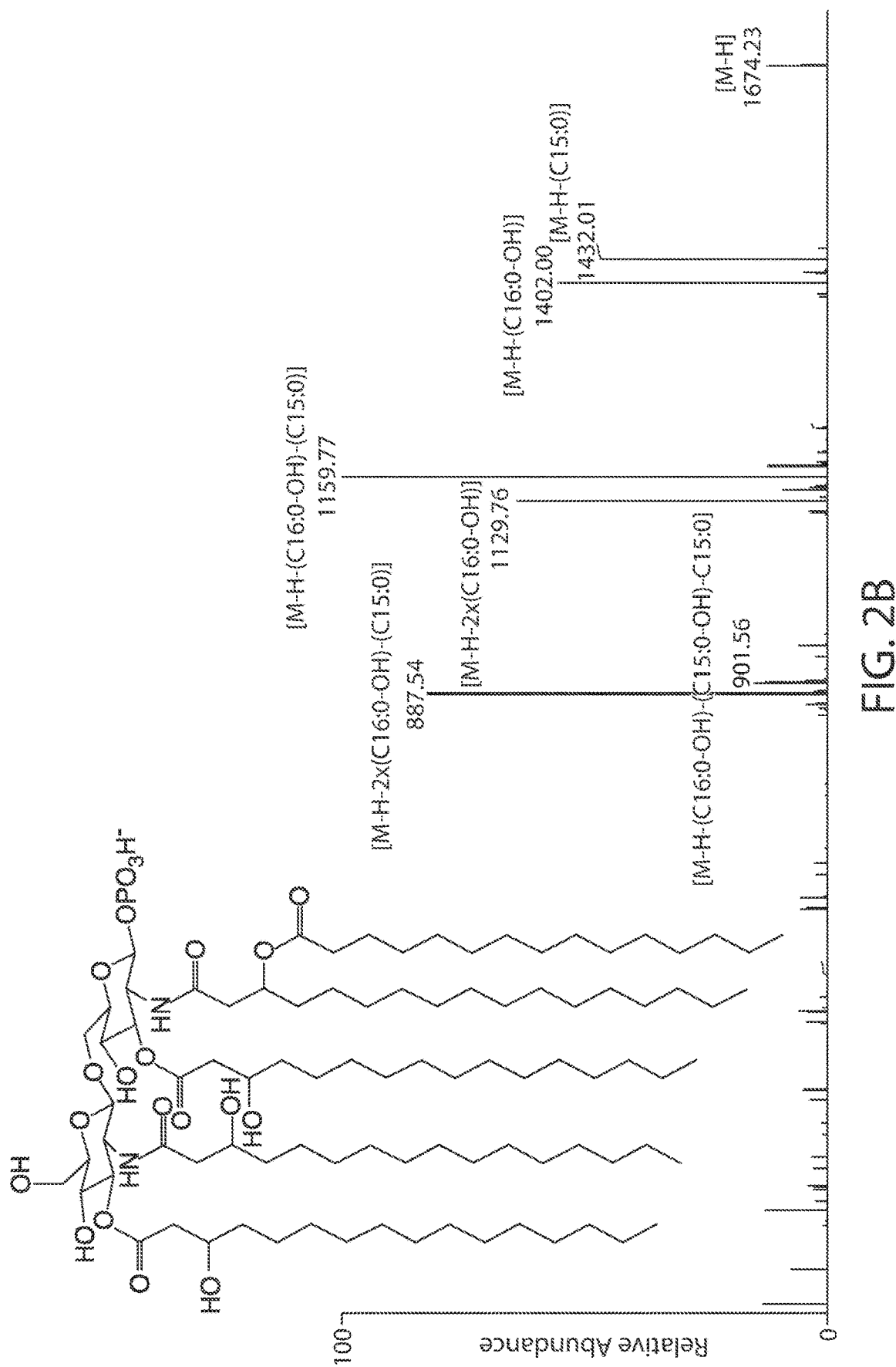
FIG. 2B provides MS/MS assignment of the structure of a species isolated from *B. fragilis*. The species at m/z=1674.2 has been determined to be a pentaacylated and monophosphorylated with saturated or monohydroxylated C15-C17 fatty acids.

These approaches can also be used to characterize the glycolipid component of lipidated PSA. For example, as shown in FIGS. 1 and 2, the tetra-acylated and penta-acylated glycolipids of lipidated PSA can be distinguished from each other using mass spectrometry. Similarly, MADLI-TOF-TOF can be used to detect and distinguish between di-, tri-, tetra- and penta-acylated glycolipids from lipidated PSA. Thus, these approaches can be used to test for the presence of specific glycolipids.

It is also possible to identify the presence of lipidated PSA using an acid treatment time course, whereby the released (unconjugated) lipid moiety can be visualized using a 16.5% Tris-Tricine SDS-PAGE gel reverse stained with zinc sulphate/imidazole staining. This staining protocol allows one to observe both the polysaccharide and lipid moieties of lipidated PSA in the same gel system. As an example, a sample being tested for lipidated PSA content may be treated with 2% acetic acid at 90° C. for various periods of time, followed by neutralization with NaOH and dialysis. One hundred micrograms of the resultant product is then run on a 16.5% Tris-Tricine SDS-PAGE gel and reverse-stained as described above. The reduction in intensity of the lipidated PSA band (the major band above 60 kD which represents lipidated and non-lipidated versions of PSA) with the concomitant emergence of one or more lipid bands at about 5 kD with increasing hydrolysis time evidences the presence of lipidated PSA. LPS bands of about 6 and 8 kD also reduce in intensity with increasing time.

Figure 10:
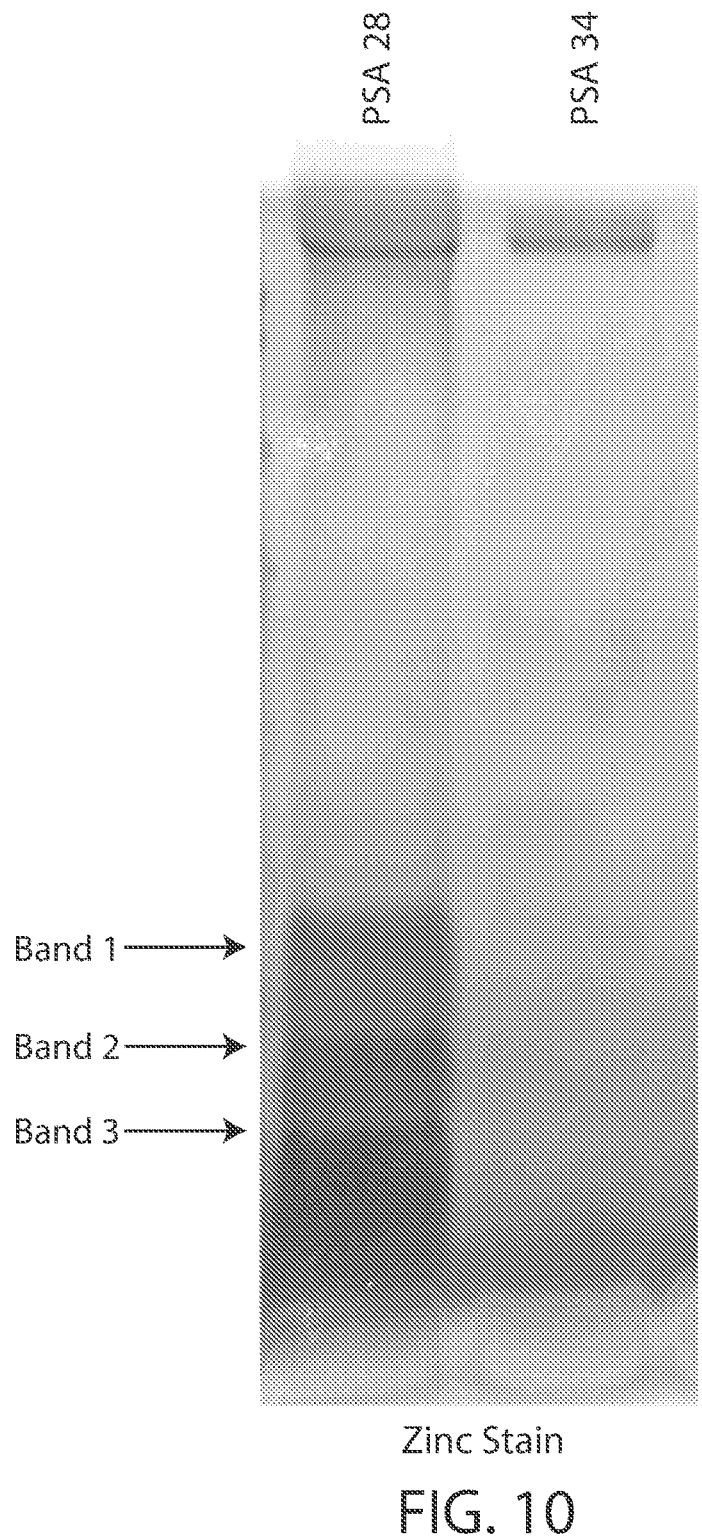
FIG. 10 is a photograph of a zinc sulphate/imidazole stained SDS PAGE gel. Isolated fully lipidated PSA preparations (PSA Lot 34) display much less free lipids as compared to PSA prepared by mild acid treatment (PSA Lot 28).
Figure 11:
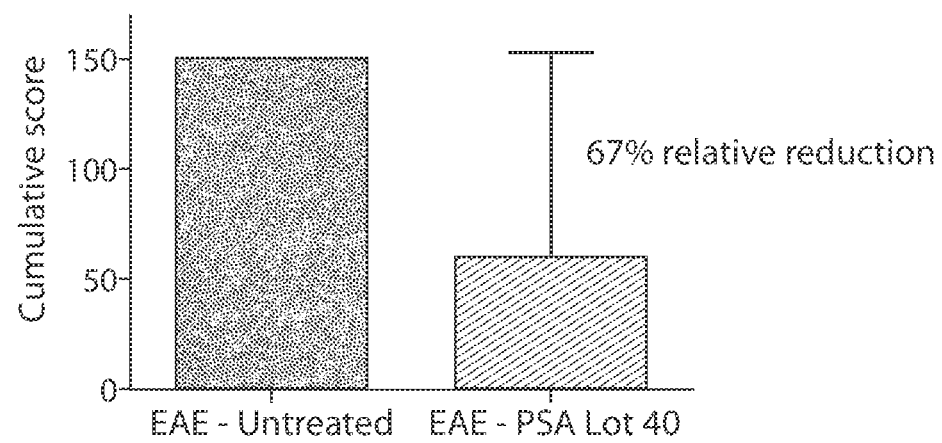
FIG. 11 is a bar graph showing EAE cumulative score of PBS and PSA Lot 40 treated mice. PBS mice, n=8; PSA mice, n=7. PSA treatment: oral gavages every other day (75 microgram dose), starting on day 2.
Figure 12:
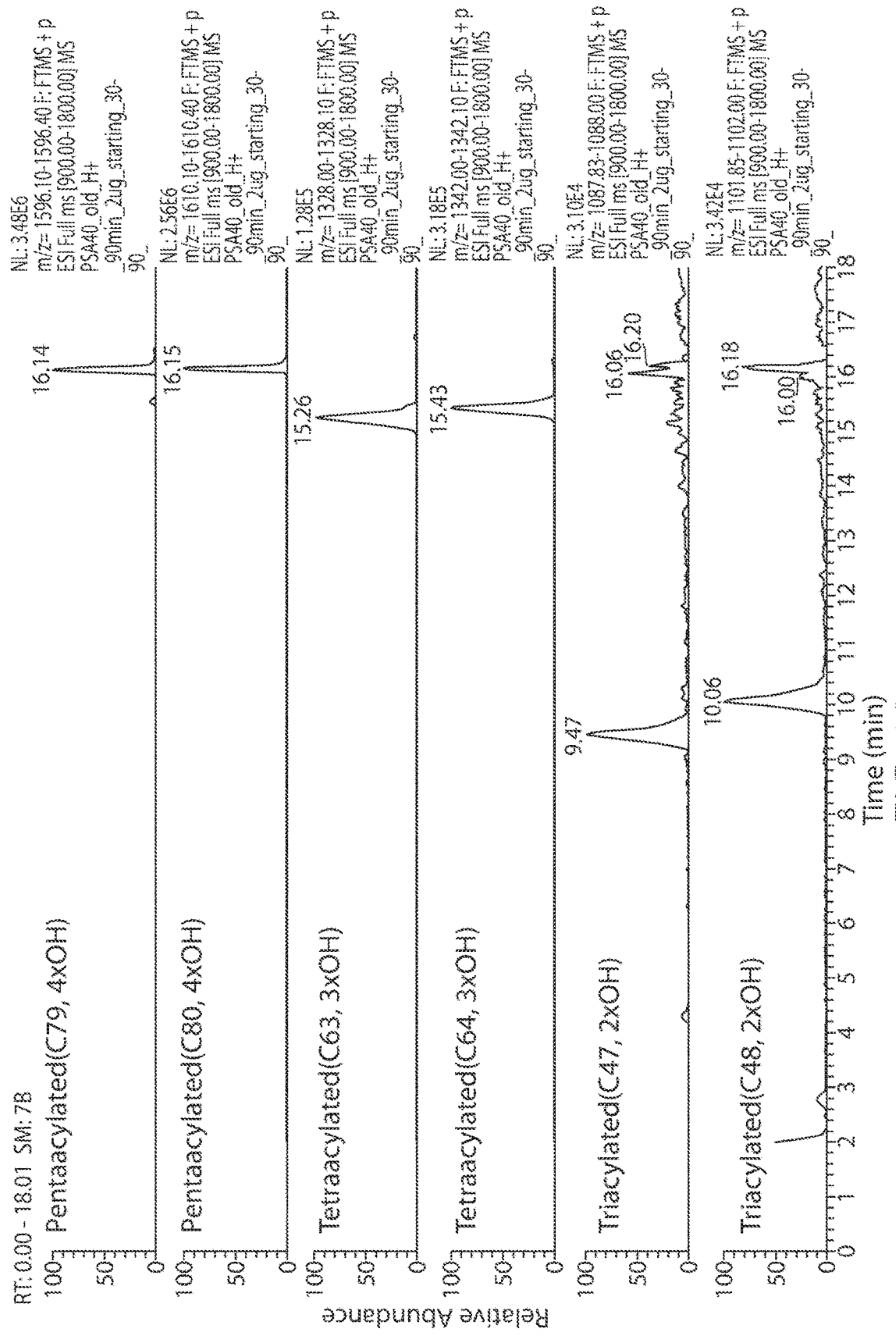
FIG. 12 provides MS spectra for a number of penta-, tetra- and tri-acylated glycolipids obtained from a lipidated PSA preparation prepared using a non-hydrolytic method (PSA Lot 40).
Figure 13:
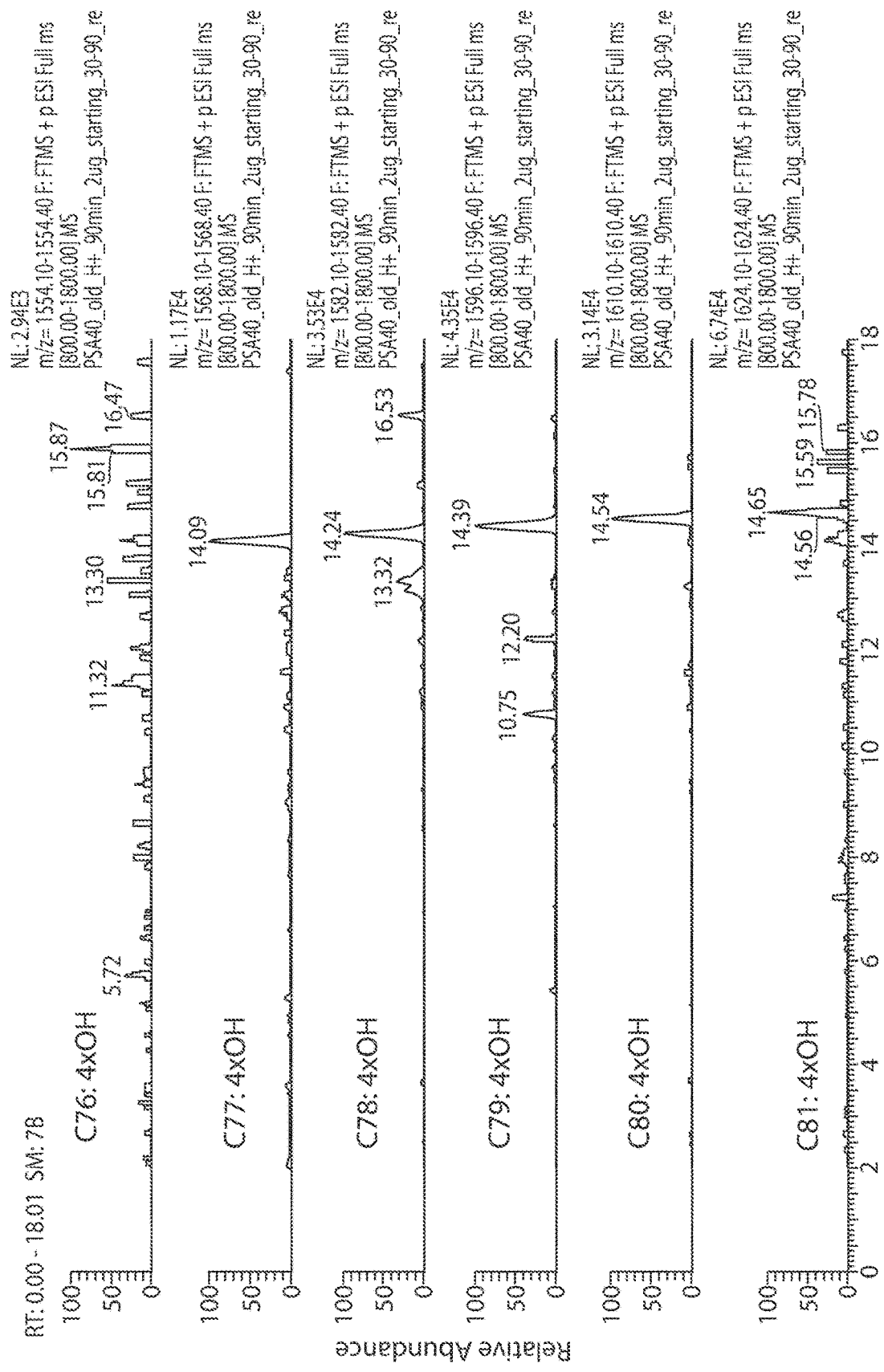
FIG. 13 provides MS spectra for a number of penta-acylated glycolipids obtained from a lipidated PSA preparation prepared using a non-hydrolytic method (PSA Lot 40).

This approach can also be used to test a lipidated PSA preparation for the presence of free, released glycolipid. FIG. 10 illustrates results of an SDS PAGE gel analysis of a preparation prepared with mild acid hydrolysis (PSA Lot 28) and a preparation prepared with no acid hydrolysis step at all (PSA Lot 34). Lot 34, isolated using a non-hydrolytic method, contains no free, released glycolipid, while Lot 28, isolated using a mild hydrolysis, does. It is to be understood that the free, released glycolipid refers to the glycolipid unconjugated to the polysaccharide PSA and such glycolipid may be referred to as being free, released or unconjugated interchangeably.

Functional Characterization

Lipidated PSA has been shown to be more potent than its non-lipidated counterpart (i.e., non-lipidated PSA). The immunological activity of lipidated PSA can be assayed in vitro and in vivo. An example of an in vitro test is the induction of IL-10 production in a splenic dendritic cell (DC) and T cell co-culture. This assay can be performed as follows: (1) splenic DCs are isolated using mouse anti-CD11c microbeads (Miltenyi Biotec cat#130-052-001); (2) CD4$^+$ T cells are isolated using Mouse T cell CD4 Subset Column Kit (R&D systems cat#MCD4C-1000); (3) $2\times10^4$ CD11c$^+$ DCs and $10^5$ CD4$^+$ T cells are mixed and 1 µg/ml anti-CD3 (BD Pharmingen cat#553057) is added; (4) the culture is then stimulated with 100 µg/ml lipidated PSA and the cells are incubated for 5 days; and (5) supernatants are harvested and analyzed by ELISA for the presence of IL-10.

Figure 7:
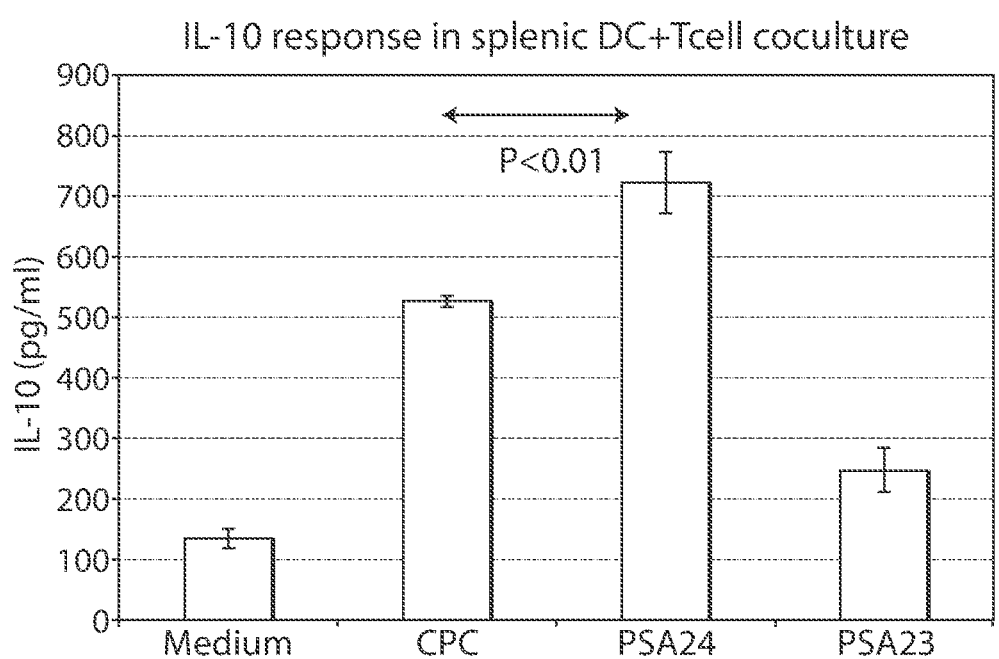
FIG. 7 is a bar graph showing the results of an IL-10 induction assay. Material prepared using the milder and early acid hydrolysis step is identified as PSA24. Material prepared using the harsher and later acid hydrolysis step is identified as PSA 23. CPC represents capsular polysaccharide complex from wild-type B. fragilis NCTC 9373.

FIG. 7 demonstrates, using this co-culture system, that lipidated PSA prepared using the milder and early acid hydrolysis step (shown as PSA 24) is approximately 3 fold more potent than material made using a harsher and later acid hydrolysis step (shown as PSA 23).

Figure 8:
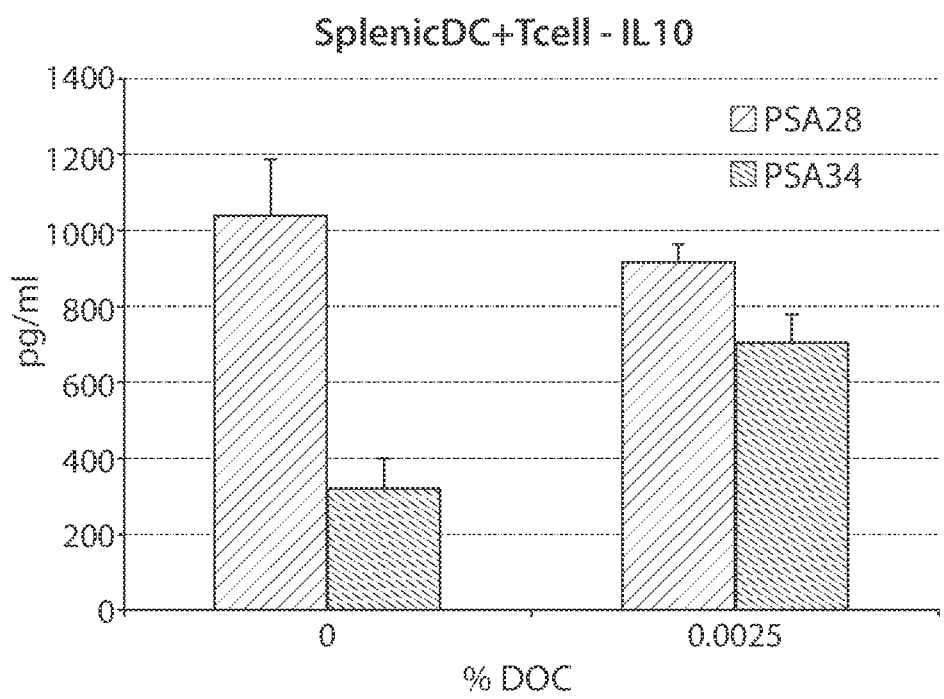
FIG. 8 is a bar graph showing the results of a IL-10 induction assay in splenic DC+Tcell coculture. The Figure uses an isolated form of lipidated PSA that is considered to be more fully lipidated than prior art preparations, intending a higher purity of lipidated PSA as compared to prior art methods. This preparation is referred to herein as "fully lipidated PSA" because it apparently contains no free (or released) glycolipid component. The Figure shows that the isolated fully lipidated PSA preparation (denoted PSA Lot 34) aggregates in the absence of deoxycholate, and such aggregation results in less IL-10 inducing activity. Addition of small amounts of deoxycholate, which disperses the aggregates or renders them less stable, results in a significant increase in the ability of Lot 34 to stimulate IL-10 production by T cells. This observation was not made using PSA Lot 28 which was prepared by mild acid treatment. This suggests that the fully lipidated PSA isolated using the methods provided herein, adopts a different conformation than lipidated PSA isolated using prior art methods.
Figure 9:
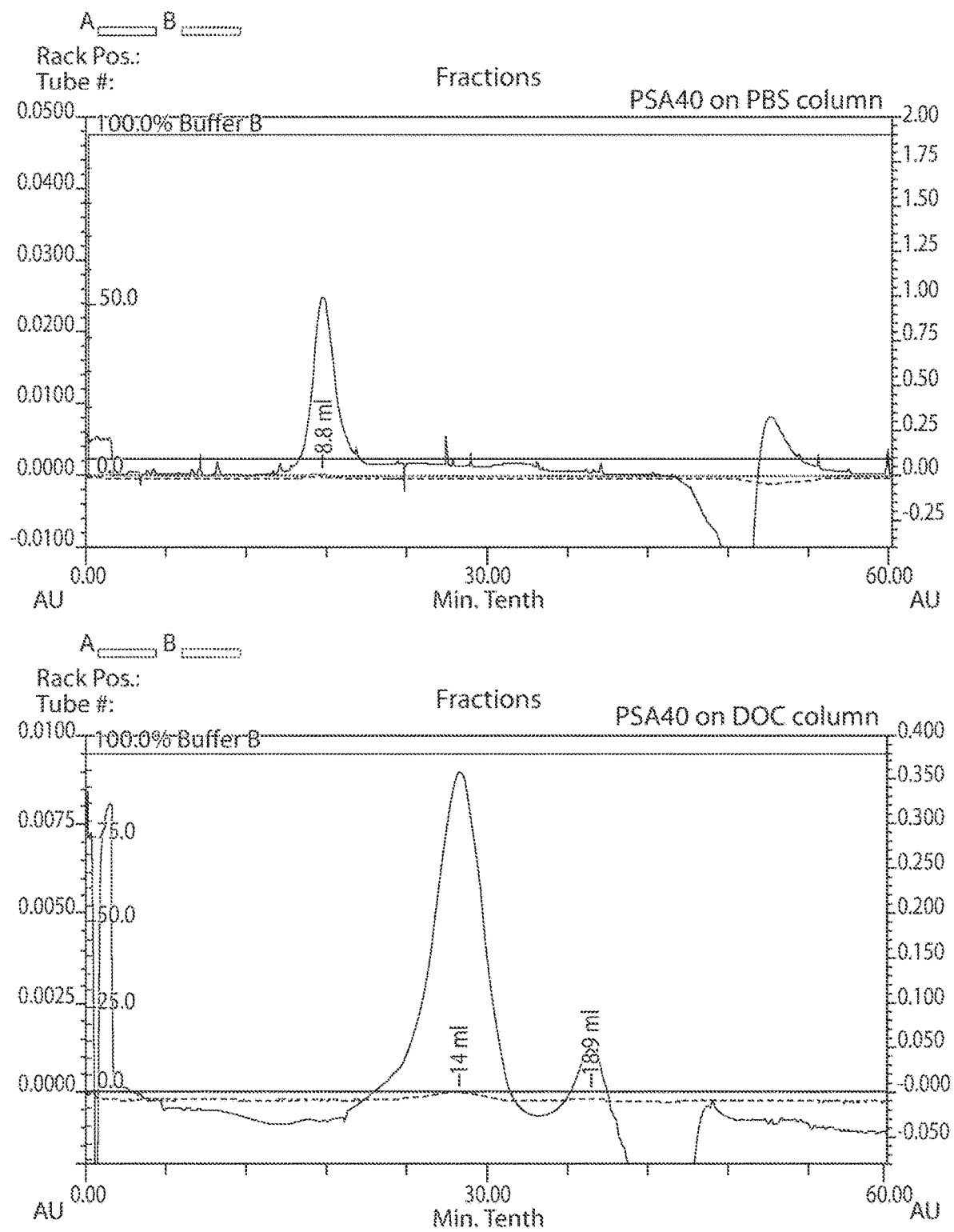
FIG. 9 provides chromatographic elution profiles of fully lipidated PSA Lot 40 using a PBS column (top) and a deoxycholate column (bottom). Monitoring molecular size of fractions by refractive index demonstrates a major reduction in size of Lot 40 when a column equilibrated with deoxycholate is used. This is due to the disruption of micelles formed by isolated, fully lipidated PSA.

FIG. 8 shows the activity in this same assay of a lipidated PSA prepared without an acid hydrolysis step (shown as PSA 34, second bar of each bar pair). The IL-10 inducing activity of this preparation is increased about 2-fold following the addition of deoxycholate (DOC). A similar increase is not observed with a lipidated PSA prepared using a milder acid hydrolysis step (shown as PSA 28, first bar of each bar pair). The increase in activity upon addition of deoxycholate suggests that the lipidated PSA is tightly aggregated and that such aggregated form is less stable, and thus the lipidated PSA is more accessible, in the presence of deoxycholate.

An animal model of multiple sclerosis (EAE) may be used to study the immunological activity of lipidated PSA in vivo. In this model, mice are treated with lipidated PSA (on the order of about 75-100 µg per mouse) or control (saline, PBS) every three days starting 6 days before EAE induction. Mice are challenged subcutaneously with 250 µg of MOG$_{33-55}$ (Peptides International) in 200 µl of complete Freund's adjuvant (Sigma). On days 0 and 2 after challenge, mice receive intraperitoneal injections of 250 ng of *Bordetella pertussis* toxin (List Biological Laboratories). Disease is scored on an established 0 to 5 scale, with 5 being advanced neurological disease. Mice are monitored and scored daily for disease progression.

Methods of Use

Also provided are methods of using the various forms of lipidated PSA in vitro and in vivo. The various forms of lipidated PSA are more potent than the previously described non-lipidated form of PSA. The various forms provided herein can be used as immunomodulators, particularly in view of their enhanced IL-10 inducing activity and Treg maturation activity. These forms are contemplated for use in vitro and in vivo. In vitro uses include use as an analytical tool (e.g., as a marker of the presence of *B. fragilis*) and as an assay standard or control (e.g., as a positive marker of lipidated PSA or a comparator in an in vitro assay such as a IL-10 induction assay). In vivo uses include uses in animal models and also clinically to treat or prevent inflammatory conditions such as but not limited to autoimmune disorders (e.g., multiple sclerosis and inflammatory bowel disease).

The invention further contemplates use of the individual polysaccharide and glycolipid components of lipidated PSA. For example, the glycolipid component may be used as a single agent. As another example, the polysaccharide and glycolipid components may be used together in an unconjugated form.

In vivo uses include but are not limited to those involving human subjects. For example, in vivo uses include administration of the lipidated PSA molecule and compositions thereof to a non-human subject in order to modulate an immune response, for example as a positive control or a comparator.

Also contemplated are methods of modulating immune responses in a subject by administering to such subject the lipidated PSA described herein. The subject may be one having or likely to develop an aberrant immune response. Typically, the aberrant immune response is an enhanced immune response and the lipidated PSA acts to down-regulate the immune response. Enhanced immune responses are typically associated with inflammatory conditions, such as but not limited to autoimmune diseases.

Accordingly, the compositions of the invention, comprising for example isolated or synthetic forms of lipidated PSA, conjugated or unconjugated forms of lipidated PSA, or the glycolipid component of lipidated PSA as a single agent or in combination with a polysaccharide other than PSA, may be used to modulate (and typically down-regulate) immune responses in subjects having or at risk of developing autoimmune diseases. As will be understood by those of ordinary skill in the art, subjects having autoimmune diseases typically experience one or more "events" or recurrences associated with the autoimmune disease. For example, a subject having inflammatory bowel disease may experience temporally isolated attacks of the disease, characterized by the presence of symptoms or increased severity of symptoms. The invention contemplates that the compositions may be used in such subjects to reduce the likelihood of such future recurrences of the disease or to reduce the severity of symptoms associated with the disease (e.g., pain, fever, discomfort, fatigue, etc.). Thus, the compositions may be administered prior to such recurrence, and in this manner may be chronically administered, optionally at a regular frequency. Examples include once a day, once every 2, 3, 4, 5 or 6 days, or once a week, etc. The invention also contemplates that the compositions may be administered to the subject during a recurrence in order to reduce the severity of symptoms or shorten the time of the recurrence.

Thus, as an example, the invention provides a method comprising administering to a subject at risk of a recurrence of a condition associated with inflammation an effective amount of a lipidated PSA in any of the forms provided herein such as but not limited to isolated or synthetic forms of lipidated PSA and/or conjugated or unconjugated forms of lipidated PSA, or an effective amount of the glycolipid component of lipidated PSA as a single agent or in combination with an agent other than PSA. The method may reduce the likelihood of a recurrence of the condition or may reduce the frequency of future recurrences. The method may reduce the severity of symptoms associated with the condition, whether such symptoms are present in the first manifestation, in a recurrence, or chronically.

Autoimmune diseases are known in the art. Examples of autoimmune diseases include but are not limited to multiple sclerosis, inflammatory bowel disease including Crohn's Disease and ulcerative colitis, rheumatoid arthritis, psoriasis, type I diabetes, uveitis, Celiac disease, pernicious anemia, Srojen's syndrome, Hashimoto's thyroiditis, Graves' disease, systemic lupus erythamatosis, acute disseminated encephalomyelitis, Addison's disease, Ankylosing spondylitis, Antiphospholipid antibody syndrome, Guillain-Barre syndrome, idiopathic thrombocytopenic purpura, Goodpasture's syndrome, Myasthenia gravis, Pemphigus, giant cell arteritis, aplastic anemia, autoimmune hepatitis, Kawaski's disease, mixed connective tissue disease, Ord throiditis, polyarthritis, primary biliary sclerosis, Reiter's syndrome, Takaysu's arteritis, vitiligo, warm autoimmune hemolytic anemia, Wegener's granulomatosis, Chagas' disease, chronic obstructive pulmonary disease, and sarcoidosis.

In important embodiments, the autoimmune disease is multiple sclerosis. In other important embodiments, the autoimmune disease is an inflammatory bowel disease including but not limited to ulcerative colitis and Crohn's disease. In other embodiments, the autoimmune disease may be rheumatoid arthritis or type I diabetes.

In some instances, the compositions of the invention may be administered to a subject who has yet to manifest an autoimmune disease (including symptoms thereof) yet is at risk of developing such as disease based on a known genetic or familial predisposition. Such a subject may have one or more family members that are afflicted with the disease.

In some instances, the compositions of the invention are administered to subject having or at risk of developing graft-versus-host disease. Administration may occur prior to, during and/or after transplantation of an organ or tissue (including blood or a blood product) into the subject.

In still other instances, the compositions may be administered to subjects having or at risk of developing a conditions associated with inflammation.

As an example, the composition may be administered to a subject having asthma. As will be understood in the art, subjects having asthma typically experience asthmatic attacks or events characterized by impaired breathing. The invention contemplates that the compositions described herein may be administered acutely (e.g., a single large dose) or chronically (e.g., repeated, smaller doses) to asthmatic subjects. Accordingly, in some instances, the compositions may be administered prior to an asthmatic attack in order to prevent the occurrence of the attack, reduce the frequency of attacks, and/or to lessen the severity of the attack. In some instances, the compositions may be administered during an attack in order to reduce its severity and/or reduce its duration.

Another condition associated with inflammation is a post-surgical adhesion. The invention contemplates administration of the compositions described herein to subjects having or at risk of developing a post-surgical adhesion. The compositions may be administered prior to, during, and/or immediately following surgery, or any combination thereof including but not limited to prior to and during surgery, in order to prevent the occurrence of such adhesions and/or reduce their severity. The compositions may be administered repeatedly following surgery, including for example every day, every two days, every three days, etc. for a week, two weeks, three weeks, a month, or several months post-surgery.

Another condition associated with inflammation is an abscess, including but not limited to an abdominal abscess as may occur upon leakage of intestinal contents into the peritoneum. In these instances, the subjects being treated may also be administered anti-bacterial agents such as antibiotics.

Thus, as another example, a method is provided that comprises administering to a subject having or at risk of developing an abscess an effective amount of any of the lipidated PSA forms described herein or the glycolipid component of lipidated PSA (separate from the polysaccharide component) or compositions thereof. In some embodiments, the subject is also administered an anti-bacterial agent such as an antibiotic. In some embodiments, the lipidated PSA is administered prior to development of an abscess and/or prior to the manifestation of symptoms associated with an abscess. In some embodiments, the lipidated PSA or glycolipid is administered after an abscess has been detected or diagnosed and/or after symptoms associated with an abscess are manifested.

Another condition associated with inflammation is obesity, and accordingly the invention also contemplates administration of the compositions described herein in subjects that are obese. Such subjects are typically defined as having a body mass index (BMI) of 30 or more. In some instances, the compositions may be administered to a subject having a BMI greater than 20 or greater than 25. The compositions are intended to prevent further weight gain and/or induce weight loss in such subjects.

A subject intends any subject that would benefit from administration of a composition of the invention or that could be administered the composition of the invention. In important embodiments, the subject is a human subject. The subject may also be a companion animal such as a dog or cat, agricultural livestock such as horses, cattle, pigs, sheep, etc., laboratory animals such as mice, rats, rabbits, monkeys, etc., or animals such as those maintained in zoos or otherwise in captivity.

A variety of administration routes are available. The particular mode selected will depend, of course, upon the particular condition being treated, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, inhalation (e.g., inhaler or nebulization), or parenteral routes. The term "parenteral" includes subcutaneous, intravenous, intramuscular, intraperitoneal, or infusion.

Formulations

When administered, the active agents of the invention are formulated as pharmaceutically acceptable compositions or preparations. Such compositions or preparations may routinely contain pharmaceutically acceptable carriers, concentrations of salt, buffering agents, preservatives, other immune modulators, and optionally other therapeutic agents. The term "pharmaceutically-acceptable carrier" as used herein, and described more fully below, means one or more compatible solid or liquid filler, diluents or encapsulating substances which are suitable for administration to a human or other animal. The term "carrier" denotes an organic or inorganic ingredient, natural or synthetic, with which the active agent(s) is combined to facilitate administration, long-term storage, stability and the like. The active agents of the present invention may be comingled with the other components of the pharmaceutical compositions, in a manner such that there is no interaction which would substantially impair the desired pharmaceutical efficacy.

The pharmaceutical compositions may be presented in unit dosage form and may be prepared by any of the methods known in the art of pharmacy. All methods include the step of bringing the active agents into association with a carrier which constitutes one or more accessory ingredients. In general, the compositions are prepared by uniformly and intimately bringing the active agent(s) into association with a liquid carrier, a finely divided solid carrier, or both, and then, if necessary, shaping the product. Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

The active agent(s) may be administered per se (neat) or in the form of a pharmaceutically acceptable salt. Pharmaceutically acceptable salts may be used for in vivo applications as well as in vitro applications. Non-pharmaceutically acceptable salts may be used to prepare pharmaceutically acceptable salts thereof and are not excluded from the scope of the invention. Pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Compositions suitable for parenteral administration conveniently comprise a sterile aqueous preparation of the active agent(s), which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal intravenous, etc. administrations may be found in Remington's Pharmaceutical Sciences, Mack Publishing Company, Easton, Pa.

In some embodiments, the lipidated PSA or the glycolipid component is formulated with a detergent such as but not limited to Tween or a bile salt such as but not limited to deoxycholate (e.g., sodium deoxycholate) in order to limit or prevent lipidated PSA aggregation. Such detergent or bile salt may be used at a low concentration such that it is still pharmaceutically acceptable. For example, it may be present at about or less than 0.0001%. 0.0005%, 0.001%. 0.002%, 0.005%, 0.01%, 0.02%, 0.05%, 0.07%, 0.1%, 0.2%, 0.3%, 0.4%, 0.5%. 0.6%, 0.7%, 0.8%, 0.9%, 1%, 2%, 3%, 4%, 5%, or more. FIG. 8 provides a composition comprising about 0.0025% deoxycholate and isolated lipidated PSA generated without acid hydrolysis.

Degradation of the lipidated PSA into glycolipid and polysaccharide components can be determined using mass spec or zinc gels as described herein (e.g., in the latter case, the released lipid is clearly identified as a faster migrating band). This is illustrated in FIG. 10.

The pharmaceutical preparations, as described above, are administered in effective amounts. For therapeutic applications, it is generally that amount sufficient to achieve a medically desirable result. In general, a therapeutically effective amount is that amount necessary to delay the onset of, inhibit the progression of, or halt altogether the particular condition being treated, including reducing the likelihood, frequency and/or severity of a recurrence of the condition. As an example, the effective amount may be that amount which serves to reduce, alleviate, or delay the onset of the symptoms (e.g., pain, fever, etc.) of the disorder being treated or prevented. The effective amount will depend upon the mode of administration, the particular condition being treated and the desired outcome. It will also depend upon the stage of the condition, the severity of the condition, the age and physical condition of the subject being treated, the nature of concurrent therapy (if any), the duration of the treatment, the specific route of administration and like factors within the knowledge and expertise of the medical practitioner. For prophylactic applications, it is that amount sufficient to delay the onset of, inhibit the progression of, or halt altogether the particular condition being prevented, and may be measured by the amount required to prevent the onset of symptoms.

Generally, doses of active agent(s) of the present invention may be from about 0.01 mg/kg per day to 1000 mg/kg per day, preferably from about 0.1 mg/kg to 200 mg/kg and most preferably from about 0.2 mg/kg to about 20 mg/kg, in one or more dose administrations daily, for one or more days. It is expected that doses ranging from 1-500 mg/kg, and preferably doses ranging from 1-100 mg/kg, and even more preferably doses ranging from 1-50 mg/kg, will be suitable. The preferred amount can be determined by one of ordinary skill in the art in accordance with standard practice for determining optimum dosage levels of the agent. It is generally preferred that a maximum dose is the highest safe dose according to sound medical judgment be used.

In some instances, the total daily dose for a human subject may range from about 50-100 micrograms of lipidated PSA or the glycolipid component isolated from the polysaccharide component.

The pharmaceutical preparation may be administered alone or in conjunction with one or more other active agents.

The pharmaceutical preparation may be used or administered in conjunction with active agents that are suitable for autoimmune disorders such as multiple sclerosis, Crohn's disease, ulcerative colitis, asthma, rheumatoid arthritis, and the like.

An example of such agents include anti-inflammatory agents. Examples include steroids and corticosteroids such as cortisone; non-steroidal anti-inflammatory drugs such as aspirin, salsalate, celecoxib, diclofenac, etodolac, ibuprofen, indomethacin, ketoprofen, ketorolac, nabumetone, naproxen, oxaprozin, piroxicam, sulindac, and tolmetin; aminosalicylates such as sulfasalazine and 5-aminosalicylates including mesalamine, balsalazide, and olsalazine; azathioprine; mercaptopurine; cyclosporine; beta interferons; glatiramer acetate; dimethyl fumarate; fingolimod; mitoxantrone; disease-modifying antirheumatic drugs (DMARDs) such as methotrexate, leflunomide, hydroxychloroquine and sulfasalazine.

Another example of such agents include antibodies or antibody fragments. Examples include TNF alpha inhibitors such as infliximab (Remicade), adalimumab (Humira), and golimumab (Simponi); natalizumab (Tysabri), vedolizumab (Entyvio); ustekinumab (Stelara); abatacept (Orencia); anakinra (Kineret); certolizumab (Cimzia), etanercept (Enbrel), rituximab (Rituxan), tocilizumab (Actemra), and tofacitinib (Xeljanz).

The invention contemplates that the combined use of lipidated PSA in the various forms described herein or isolated glycolipid component of lipidated PSA together with standard treatments such as those recited above will allow a lower dose of the standard treatment to be used for the same or better therapeutic effect, and/or will result in reduced incidence and/or severity of side effects associated with such standard treatments.

In one embodiment the pharmaceutical preparation is given in conjunction with one or more anti-bacterial agents including antibiotics selected from the group consisting of penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmnenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin.

The following Examples are included for purposes of illustration and are not intended to limit the scope of the invention.

EXAMPLES

Example 1. Isolation of Lipidated PSA

Briefly, B. fragilis was grown in anaerobic conditions. The capsular complex from B. fragilis was isolated with hot phenol/water extraction. The polysaccharide fraction was precipitated with ethanol after DNAse, RNase and pronase treatments. The precipitate was subjected to size exclusion chromatography in order to separate the lipidated PSA from other polysaccharide constituents. The fractions of interest were analyzed and pooled, then dialyzed and lyophilized. The purity of lipidated PSA was assessed by nuclear magnetic resonance spectroscopy and mass spectroscopy.

The isolation and purification process of lipidated PSA is provided below in greater detail.

The B. fragilis delta44 mutant strain was derived experimentally from strain 9343 and upon further characterization it was found to over-express PSA relative to PSB. Delta44 was plated onto a blood agar plate and grown overnight at 37° C. A swab from a heavily colonized plate was subcultured into a 500 ml starter culture of peptone yeast broth. The starter culture was inoculated into 16 liter culture of the same media and pH was titrated to neutrality with 5M NaOH. An anaerobic gas mix was bubbled into the sealed culture.

After an overnight culture maintained at pH 7, bacteria were checked by Gram stain and subculture. Organisms were collected by centrifugation at 8,000×g for 20 minutes. Bacterial pellets were washed two times with saline yielding approximately one liter of bacterial pellet.

The bacterial pellet was suspended in 68° C. melted crystalline phenol to a final concentration of phenol of about 37% v/v (yielding a phenol/water preparation) and mixed for 30 minutes at 68° C. followed by stirring at 4° C. for 48 hours. The phenol/water preparation was aliquoted into glass bottles which were then centrifuged at 1500 rpm. The upper water layer was harvested. Any residual phenol contained in the harvested aqueous phase was extracted with an equal volume of ethyl ether. The ether phase was then removed using a separatory funnel and any residual ether in the aqueous phase was evaporated, yielding the final aqueous phase from the phenol/water preparation.

The aqueous phase was dialyzed versus water with multiple changes over 5 days at 4° C. and subsequently lyophilized until it was nearly dry (approximately 5 ml water remaining). A solution of 0.05M Tris with magnesium, calcium and sodium azide (total volume 61 ml) was added to the lyophilized product to bring the total volume to about 66 ml.

To the dissolved product was added 10 ml of Tris buffer with DNase (0.07 mg/ml) and RNase (0.33 mg/ml). The entire suspension was filtered through a 0.45 micron filter and the filtrate was stirred at 37° C. The DNase/RNase treatment was repeated by adding fresh enzymes to the mixture, at similar concentrations, and stirred for two hours.

The mixture was then combined with 25 mg pronase in 10 ml Tris/magnesium/calcium solution, and the mixture stirred for 24 hours at 37° C. This step was repeated.

The polysaccharide fraction was precipitated by adding 5 volumes of ethanol at 4° C. to the mixture. The solution was then centrifuged at 12,000×g for 30 minutes to pellet the polysaccharide fraction. The supernatant was removed and the pellet was resuspended in 392 ml type 1 $H_2O$.

The dissolved fraction was then dialyzed against two changes of 16 liters type 1 $H_2O$ at 4° C. The volume was reduced by lyophilization to approximately 50 mls.

Twenty ml aliquots were chromatographed on a 5×200 cm column of S400 suspended in PBS and 1% sodium deoxycholate, and fractions were collected. Fractions were tested by double diffusion in agar with an antibody that reacts with both lipidated and non-lipidated PSA to determine where lipidated PSA eluted. Aliquots were tested for UV absorption at 280 nm and it was determined that lipidated PSA-containing fractions had no UV absorbable material.

Fractions containing lipidated PSA were then pooled, concentrated and dialyzed against type 1 $H_2O$ on a Minitan concentrator (Millipore) with 10,000 mw cutoff membranes until conductivity of 100 ml was less than 50 µS. Lipidated PSA was then lyophilized.

Polysaccharide and glycolipid purity and structure was determined by proton nuclear magnetic resonance spectroscopy on a 600 MHz spectrometer and mass spectroscopy. For MALDI-TOF-TOF and LC-MS analysis, the lipidated PSA sample was resuspended to 10 µg/µL in 2% acetic acid and heated at 90 degrees for 90 minutes. For MALDI-TOF-TOF analysis, samples were mixed 1:1 to 1% matrix (CHCA or DHB) solution and directly loaded to stainless steel MALDI plate. For LC-MS analysis, samples did or did not undergo liquid-liquid extraction (chloroform-water) step, and then were dried and resuspended in 50:50 isopropanol:acetonitrile and injected.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A non-hydrolytic method for isolating lipidated polysaccharide A (PSA) from *Bacteroides fragilis* (*B. fragilis*), comprising
    extracting, into an aqueous phase, capsular complex from *B. fragilis* using a mixture of phenol and water,
    precipitating a polysaccharide fraction from the aqueous phase using ethanol, and
    isolating lipidated PSA from the polysaccharide fraction by size exclusion, wherein a non-hydrolytic method is a method that lacks an acid hydrolysis step.

2. The method of claim 1, wherein isolating by size exclusion comprises using a chromatographic column comprising a detergent or a bile salt.

3. The method of claim 2, wherein the chromatographic column comprises deoxycholate.

4. The method of claim 1, wherein the method is performed at a pH less than about 9.

5. The method of claim 1, further comprising dialyzing the isolated lipidated PSA.

6. The method of claim 1, wherein extraction occurs at 60-75° C.

7. The method of claim 1, wherein extraction occurs at about 68° C.

8. The method of claim 1, wherein the method is performed in the presence of sodium deoxycholate.

9. The method of claim 1, wherein *B. fragilis* is a mutant form of *B. fragilis* that over-expresses PSA relative to PSB.

10. The method of claim 1, wherein the isolated lipidated PSA is substantially free of unconjugated glycolipid.

11. The method of claim 1, wherein the *B. fragilis* is wild-type *B. fragilis*.

12. A non-hydrolytic method for isolating lipidated polysaccharide A (PSA) from *B. fragilis*, comprising
- extracting, into an aqueous phase, capsular complex from *B. fragilis* using a mixture of phenol and water,
- precipitating a polysaccharide fraction from the aqueous phase using ethanol,
- isolating lipidated PSA from the polysaccharide fraction by size exclusion, and
- formulating the isolated lipidated PSA as a pharmaceutical composition, wherein a non-hydrolytic method is a method that lacks an acid hydrolysis step.

\* \* \* \* \*